(12) United States Patent
Viitanen et al.

(10) Patent No.: US 7,629,156 B2
(45) Date of Patent: Dec. 8, 2009

(54) ETHANOL PRODUCTION IN FERMENTATION OF MIXED SUGARS CONTAINING XYLOSE

(75) Inventors: Paul V. Viitanen, West Chester, PA (US); Carol M. Mc Cutchen, Wilmington, DE (US); Xu Li, Newark, DE (US); Mark Emptage, Wilmington, DE (US); Perry G. Caimi, Kennett Square, PA (US); Min Zhang, Lakewood, CO (US); Yat-Chen Chou, Lakewood, CO (US); Mary Ann Franden, Centennial, CO (US)

(73) Assignees: E.I. du Pont de Nemours and Company, Wilmington, DE (US); Alliance For Sustainable Energy, LLC, Golden, CO (US)

(*) Notice: Subject to any disclaimer, the term of this patent is extended or adjusted under 35 U.S.C. 154(b) by 0 days.

(21) Appl. No.: 11/862,522

(22) Filed: Sep. 27, 2007

(65) Prior Publication Data

US 2008/0081358 A1   Apr. 3, 2008

Related U.S. Application Data

(60) Provisional application No. 60/847,997, filed on Sep. 28, 2006.

(51) Int. Cl.
*C12P 7/06* (2006.01)
*C12N 1/20* (2006.01)
*C12N 15/00* (2006.01)
*C07H 21/04* (2006.01)

(52) U.S. Cl. .................. 435/161; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 5,231,020 A | 7/1993 | Jorgensen | |
| 5,514,583 A | 5/1996 | Picataggio et al. | |
| 5,712,133 A | 1/1998 | Picataggio et al. | |
| 5,843,760 A | 12/1998 | Zhang et al. | |
| 6,566,107 B1 | 5/2003 | Zhang | |
| 2003/0162271 A1 | 8/2003 | Zhang et al. | |

FOREIGN PATENT DOCUMENTS

| | | |
|---|---|---|
| CN | 1600850 | 9/2003 |
| WO | 95/28476 | 10/1995 |
| WO | 01/83784 | 11/2001 |
| WO | 2004/037973 A | 5/2004 |
| WO | 2004/081185 A2 | 9/2004 |

OTHER PUBLICATIONS

Mohagheghi et al. Biotechnol Lett. Feb. 2004;26(4):321-5.*
U.S. Appl. No. 60/847,813, filed Sep. 28, 2008, Paul V. Viitanen et al.
U.S. Appl. No. 60/670,437, filed Apr. 12, 2005, James B. Dunson et al.
Zhang et al., Metabolic Engineering of a Pentose Metabolism Pathway in Ethanoloenic *Zymomonas mobilis*, Science, 1995, vol. 267:240-243.
Feldmann et al., Pentose Metabolism in *Zymomonas mobilis* Wild-Type and Recombinant Strains, Appl. Microbiol. Biotechnol., 1992, vol. 38:354-361.
Kim et al., Kinetic and Nuclear Magnetic Resonance Studies of Xylose Metabolism by Recombinant Mobilis ZM4 (pzb), Applied and Environmental Microbiology, 2000, vol. 66:186-193.
Lawford et al., The Effect of Glucose on High-Level Xylose Fermentations by Recombinant *Zymomonas* in Batch and Fed-Batch Fermentations, Appl. Biochem. & Biotech., 1999, vol. 77-79:235-249.
Joachimsthal et al., Characterization of a High-Productivity Recombinant Strain of *Zymomonas mobilis* for Ethanol Production From Glucose/Xylose Mixtures, Appl. Biochem. & Biotechnol., 2000, vol. 84-86:343-356.
Loos et al., Sorbitol Promotes Growth of *Zymomonas mobilis* in Environments With High Concentrations of Sugar: Evidence for a Physiological Function of Glucose-Fructose Oxidoreductase in Osmoprotection, J. Bacteriol., 1994, vol. 176:7688-7693.
Lynd et al., Microbial Cellulose Utilization? Fundamentals and Biotechnology,Microbiol. Mol. Biol. Rev., 2002, vol. 66:506-577.
Crueger et al. Biotechnology: A Textbook of Industrial Microbiology, 1989, 2nd Edition, Sinauer Associates, Inc. (Book Not Included).
Deshpande et al., Ethanol Production From Cellulose by Coupled Saccharification/Fermentation Using *Saccharomyces cerevisiae* and Cellulase Complex From Sclerotium Rolfsii UV-8 Mutant, Appl. Biochem. Biotechnol., 1992, vol. 36:227-234.
Sambrook et al., Molecular Cloning: A Laboratory Manual, 2nd Edition, 1989, Cold Spring Harbor Laboratory (Book Not Included).
Silhavy et al., Experiments With Gene Fusions, 1984, Cold Spring Barbor Laboratory, (Book Not Included).
Ausubel et al., Current Protocols in Molecular Biology, 1987, Greene Publishing Assoc., (Book Not Included).
U.S. Appl. No. 60/847,997, filed Sep. 28, 2006, Paul V. Viitanen et al.
Smith et al., D-Xylose (D-Glucose) Isomerase From Arthrobacter Strain N.R.R.L. B3728, Biochem. J., 1991, vol. 227:255-261.
Danielson, Limitations of Pentose Sugar Conversion in Recombinant *Zymomonas mobilis* and Methods to Address These Limitations, University of Colorado Masters Thesis, 2001, pp. 1-64.

(Continued)

*Primary Examiner*—Christian L Fronda

(57) ABSTRACT

Xylose-utilizing *Z. mobilis* strains were found to have improved ethanol production when grown in medium containing mixed sugars including xylose if sorbitol or mannitol was included in the medium. The effect was seen in concentrations of mixed sugars where no growth lag period occurs, as well as in higher sugars concentrations.

8 Claims, 23 Drawing Sheets

OTHER PUBLICATIONS

Wiegert et al., Export of the Periplasmic NADP-Containing Glucose-Fructose Oxidoreductase of *Zymomonas mobilis*, Arch. Microbiol., 1996, vol. 166:32-41.

Kirk et al., Rapid Ethanol Production From Sucrose Without by-Product Formation, Biotechnol. Letters, 1993, vol. 15:985-990.

Mohagheghi et al., Cellular Biosensing System for Assessing Immunomodulating Effects on the Inducible Nitric Oxide Synthase (iNOS) Cascade, Biotechnol. Lett., 2003, vol. 25:321-325.

Zachariou et al., Glucose-Fructose Oxidoreductase, A New Enzyme Isolated From *Zymomonas mobilis* That is Responsible for Sorbitol Production, Journal of Bacteriology, 1986, vol. 167:863-869.

National Center for Biotechnology Information General Identifier No. 206201, Apr. 27, 1993, H. Inoue et al., Complete Amino Acid Sequence of Rat L-Type Pyruvate Kinase Deduced From the CDNA Sequence, Accession No. M17685.

National Center for Biotechnology Information General Identifier No. 58255, Nov. 14, 2006, R.E Rose, the Nucleotide Sequence of PACYC184, Accession No. X06403.

Kim et al., Nuclear Magnetic Resonance Studies of Acetic Acid Inhibition of REC *Zymomonas* ZM4 (PZB5), Applied Biochemistry and Biotechnology, 2000, vol. 84:357-370.

Sternberg et al., Bacteriophage P1 Site-Specific Recombination I. Recombination Between loxP Sites, J. Mol. Biol., 1981, vol. 150:467-486.

Trinh et al., Site-Specific and Directional Gene Replacement Mediated by Cre Recombinase, Journal of Immunological Methods, 2000, vol. 244:185-193.

Sternberg et al., Bacteriophage P1 cre Gene and Its Regulatory Region Evidence for Multiple Promoters and for Regulation by DNA Methylation, J. Mol. Biol., 1986, vol. 187:197-212.

National Center for Biotechnology Information General Identifier No. 15135, Sep. 12, 1993, N. Sternberg et al., Bacteriophage P1 Cre Gene and its Regulatory Region. Evidence for Multiple Promoters and for Regulation by DNA Methylation, Accession No. X03453.

Mohagheghi et al., Cofermentation of Glucose, Xylose, and Arabinose by Genomic DNA-Integrated Xylose/Arabinose Fermenting Strain of *Zymomonas Mobilis* AX101, Applied Biochemistry and Biotechnology, Apr. 2002, pp. 885-898, vol. 98-100, Clifton, NJ.

Zaldivar et al., Fuel Ethanol Production From Lignocellulose: A Challenge for Metabolic Engineering and Process Integration, Applied Microbiology and Biotechnology, Jul. 2001, pp. 17-34, vol. 56, Springer Verlag.

International Search Report for International Patent Application No. PCT/US2007/020946 Dated June 20, 2008.

International Preliminary Report on Patentability in related PCT/US2007/020946 mailed Apr. 9, 2009.

* cited by examiner

SEQUENCE LISTING

<160> NUMBER OF SEQ ID NOS: 16

<210> SEQ ID NO 1
<211> LENGTH: 44
<212> TYPE: DNA
<213> ORGANISM: artificial equence
<220> FEATURE:
<223> OTHER INFORMATION: primer

<400> SEQUENCE: 1
cagtctagag gccgcctagg ccgttcgatc aacaacccga atcc          44

<210> SEQ ID NO 2
<211> LENGTH: 30
<212> TYPE: DNA
<213> ORGANISM: artificial sequence
<220> FEATURE:
<223> OTHER INFORMATION: primer

<400> SEQUENCE: 2
caatttgtcc gtcatgttta ttctcctaac                          30

<210> SEQ ID NO 3
<211> LENGTH: 30
<212> TYPE: DNA
<213> ORGANISM: artificial sequence
<220> FEATURE:
<223> OTHER INFORMATION: primer

<400> SEQUENCE: 3
gttaggagaa taaacatgac ggacaaattg                          30

<210> SEQ ID NO 4
<211> LENGTH: 29
<212> TYPE: DNA
<213> ORGANISM: artificial sequence
<220> FEATURE:
<223> OTHER INFORMATION: primer

<400> SEQUENCE: 4
ccagatcgtc tagattacag cagatcgcc                           29

<210> SEQ ID NO 5
<211> LENGTH: 44
<212> TYPE: DNA
<213> ORGANISM: artificial sequence
<220> FEATURE:
<223> OTHER INFORMATION: primer

<400> SEQUENCE: 5
cagtctagag gccgcctagg ccgttcgatc aacaacccga atcc          44

<210> SEQ ID NO 6
<211> LENGTH: 29
<212> TYPE: DNA
<213> ORGANISM: artificial sequence
<220> FEATURE:
<223> OTHER INFORMATION: primer

<400> SEQUENCE: 6
ccagatcgtc tagattacag cagatcgcc                               29

<210> SEQ ID NO 7
<211> LENGTH: 73
<212> TYPE: DNA
<213> ORGANISM: artificial sequence
<220> FEATURE:
<223> OTHER INFORMATION: primer

<400> SEQUENCE: 7
cagggccgcc taggccataa cttcgtatag catacattat acgaagttat cctgtgacgg      60
aagatcactt cgc                                                        73

<210> SEQ ID NO 8
<211> LENGTH: 71
<212> TYPE: DNA
<213> ORGANISM: artificial sequence
<220> FEATURE:
<223> OTHER INFORMATION: primer

<400> SEQUENCE: 8
cagggcctag gcggccataa cttcgtataa tgtatgctat acgaagttat cctgaaccga      60
cgaccgggtc g                                                          71

<210> SEQ ID NO 9
<211> LENGTH: 6882
<212> TYPE: DNA
<213> ORGANISM: artificial sequence
<220> FEATURE:
<223> OTHER INFORMATION: plasmid pMODPgaptaltktCm

<400> SEQUENCE: 9
cggccataac ttcgtataat gtatgctata cgaagttatc ctgaaccgac gaccgggtcg      60
aatttgcttt cgaatttctg ccattcatcc gcttattatc acttattcag gcgtagcacc     120
aggcgtttaa gggcaccaat aactgcctta aaaaaattac gccccgccct gccactcatc     180
gcagtactgt tgtaattcat taagcattct gccgacatgg aagccatcac agacggcatg     240
atgaacctga atcgccagcg gcatcagcac cttgtcgcct tgcgtataat atttgcccat     300
ggtgaaaacg ggggcgaaga agttgtccat attggccacg tttaaatcaa aactggtgaa     360
actcacccag ggattggctg agacgaaaaa catattctca ataaaccctt tagggaaata     420
ggccaggttt tcaccgtaac acgccacatc ttgcgaatat atgtgtagaa actgccggaa     480
atcgtcgtgg tattcactcc agagcgatga aaacgtttca gtttgctcat ggaaaacggt     540
gtaacaaggg tgaacactat cccatatcac cagctcaccg tctttcattg ccatacggaa     600
ttccggatga gcattcatca ggcgggcaag aatgtgaata aaggccggat aaaacttgtg     660
cttatttttc tttacggtct ttaaaaaggc cgtaatatcc agctgaacgg tctggttata     720
ggtacattga gcaactgact gaaatgcctc aaaatgttct ttacgatgcc attgggatat     780
atcaacggtg gtatatccag tgatttttt ctccatttta gcttccttag ctcctgaaaa     840
tctcgataac tcaaaaaata cgcccggtag tgatcttatt tcattatggt gaaagttgga     900

-continued

```
acctcttacg tgccgatcaa cgtctcattt tcgccaaaag ttggcccagg gcttcccggt    960
atcaacaggg acaccaggat ttatttattc tgcgaagtga tcttccgtca caggataact   1020
tcgtataatg tatgctatac gaagttatgg cctaggcggc ctctagagtc gacctgcagg   1080
catgcaagct tcagggttga gatgtgtata agagacagct gcattaatga atcggccaac   1140
gcgcggggag aggcggtttg cgtattgggc gctcttccgc ttcctcgctc actgactcgc   1200
tgcgctcggt cgttcggctg cggcgagcgg tatcagctca ctcaaaggcg gtaatacggt   1260
tatccacaga atcaggggat aacgcaggaa agaacatgtg agcaaaaggc cagcaaaagg   1320
ccaggaaccg taaaaaggcc gcgttgctgg cgttttccca taggctccgc cccccctgacg   1380
agcatcacaa aaatcgacgc tcaagtcaga ggtggcgaaa cccgacagga ctataaagat   1440
accaggcgtt tccccctgga agctcccctcg tgcgctctcc tgttccgacc ctgccgctta   1500
ccggatacct gtccgccttt ctcccttcgg gaagcgtggc gctttctcat agctcacgct   1560
gtaggtatct cagttcggtg taggtcgttc gctccaagct gggctgtgtg cacgaacccc   1620
ccgttcagcc cgaccgctgc gccttatccg gtaactatcg tcttgagtcc aacccggtaa   1680
gacacgactt atcgccactg gcagcagcca ctggtaacag gattagcaga gcgaggtatg   1740
taggcggtgc tacagagttc ttgaagtggt ggcctaacta cggctacact agaaggacag   1800
tatttggtat ctgcgctctg ctgaagccag ttaccttcgg aaaaagagtt ggtagctctt   1860
gatccggcaa acaaaccacc gctggtagcg gtggtttttt tgtttgcaag cagcagatta   1920
cgcgcagaaa aaaaggatct caagaagatc ctttgatctt ttctacgggg tctgacgctc   1980
agtggaacga aaactcacgt taagggattt tggtcatgag attatcaaaa aggatcttca   2040
cctagatcct tttaaattaa aaatgaagtt ttaaatcaat ctaaagtata tatgagtaaa   2100
cttggtctga cagttaccaa tgcttaatca gtgaggcacc tatctcagcg atctgtctat   2160
ttcgttcatc catagttgcc tgactccccg tcgtgtagat aactacgata cgggagggct   2220
taccatctgg ccccagtgct gcaatgatac cgcgagaccc acgctcaccg gctccagatt   2280
tatcagcaat aaaccagcca gccggaaggg ccgagcgcag aagtggtcct gcaactttat   2340
ccgcctccat ccagtctatt aattgttgcc gggaagctag agtaagtagt tcgccagtta   2400
atagtttgcg caacgttgtt gccattgcta caggcatcgt ggtgtcacgc tcgtcgtttg   2460
gtatggcttc attcagctcc ggttcccaac gatcaaggcg agttacatga tcccccatgt   2520
tgtgcaaaaa agcggttagc tccttcggtc ctccgatcgt tgtcagaagt aagttggccg   2580
cagtgttatc actcatggtt atggcagcac tgcataattc tcttactgtc atgccatccg   2640
taagatgctt ttctgtgact ggtgagtact caaccaagtc attctgagaa tagtgtatgc   2700
ggcgaccgag ttgctcttgc ccggcgtcaa tacgggataa taccgcgcca catagcagaa   2760
ctttaaaagt gctcatcatt ggaaaacgtt cttcggggcg aaaactctca aggatcttac   2820
cgctgttgag atccagttcg atgtaaccca ctcgtgcacc caactgatct tcagcatctt   2880
ttactttcac cagcgtttct gggtgagcaa aaacaggaag gcaaaatgcc gcaaaaaagg   2940
gaataagggc gacacggaaa tgttgaatac tcatactctt ccttttttcaa tattattgaa   3000
gcatttatca gggttattgt ctcatgagcg gatacatatt tgaatgtatt tagaaaaata   3060
aacaaatagg ggttccgcgc acatttcccc gaaaagtgcc acctgacgtc taagaaacca   3120
ttattatcat gacattaacc tataaaaata ggcgtatcac gagtcgcgcg tttcggtgat   3180
gacggtgaaa acctctgaca catgcagctc ccggagacgg tcacagcttg tctgtaagcg   3240
gatgccggga gcagacaagc ccgtcagggc gcgtcagcgg tgttggcgg gtgtcgggc    3300
```

```
tggcttaact atgcggcatc agagcagatt gtactgagag tgcaccatat gcggtgtgaa    3360
ataccgcaca gatgcgtaag gagaaaatac cgcatcaggc gccattcgcc attcaggctg    3420
cgcaactgtt gggaagggcg atcggtgcgg gcctcttcgc tattacgcca gctgtctctt    3480
atacacatct caaccatcat cgatgaattc gagctcggta cccgggggatc tgcgcaaacg    3540 gacattatca aggtaataaa aaaggtcgcc gaagcgacct tttttacccg aaatgctaat    3600
tacagcagtt cttttgcttt cgcaacaacg ttatcaacag tgaagccgaa ctcttcaaac    3660
agcagctctg ccgagcaga ttcaccgaag gtggtcatac cgacgatagc accgttcagg    3720
ccaacatact tgtaccagta gtcagcaata cccgcttcta cagcaacgcg tgcagtaacc    3780
gctttcggca gtacggattc acggtaagca gcatcctgct tgtcaaatgc gtcggtagac    3840
gacatggaca ccacgcgcgc tttcacgcct tcggcagtca gttttcgta ggcagcaaca    3900 gccagttcaa cttctgaacc ggtagcgatg aaaatcagtt ccggctgacc ggcgcagtct    3960
ttcagcacat aaccaccgcg cgcgatgttt gccagttgct cttcagttcg ttcctgctgc    4020
gccaggttct gacgggagag gatcagtgcg gtcgggccgt cctgacgctc aacaccgtat    4080
ttccacgcga ccgcggattc aacctggtca cacggacgcc atgtagacat gttcggggtt    4140
acgcgcagag aagcgacctg ctcaaccggc tggtgagtcg gcccgtcttc gcccagaccg    4200
atggagtcgt gggtgtaaac catcacctga cgctgtttca tcagcgcagc catacgtacg    4260
gcgttacgtg cgtattccac gaacatcagg aaggtggagg tgtacggcag aagccaccg    4320 tgcagggaga taccgttagc aatcgcggtc ataccgaact cgcgaacacc gtagtggatg    4380
tagttacccg cagcatcttc gttgattgct ttagaaccag accacagggt caggttagac    4440
ggcgccaggt cagcagaacc gccgaggaat tccggcaaca gcggaccgaa cgcttcgata    4500
gcattctgag acgctttacg gctggcgatt ttcgccggat tagcctgcag tttagcgatg    4560
aactctttcg ctttagcgtc gaagtcagac ggcattcgc ctttcatacg gcgggtaaat    4620
tcagcggctt cctgcggata agctttcgcg taagcagcga atttctcgtt ccatgcggat    4680
tctttcgcct ggcctgcttc tttcgcatcc cactgagcat agatttcaga cgggatttcg    4740
aacggcgcat atttccagcc cagttgttcg cgggtcaggg caatttcagc gtcgcccagc    4800
ggcgcaccgt gggagtcgtg ggtaccggct ttgttcgggg aaccgaaacc gatgatggtt    4860
ttgcacatca gcagggaagg tttgtcagtc actgcgcgcg cttcttctac tgcgcgtttg    4920
atagatgccg cgtcatgacc gtcgatgtcg cgaataacgt gccagccgta agcttcgaaa    4980
cgcattgcgg tgtcgtcggt gaaccagcct tcaacgtgac catcgataga aataccgttg    5040
tcatcgtaga atgcaatcag tttacccagc ttcagcgtac ccgccagaga gcaaacttcg    5100
tgggagatgc cttccatcat gcagccgtcg cccatgaagg cgtaggtgta gtggtcgaca    5160
atgtcgtggc ccgacggtt aaactgcgcc gccagcgttt tttctgcaat cgccataccg    5220
actgcgttgg caatacccctg acccagcgga ccggtggtgg tttccacacc cagcggtgta    5280
accccacttt ccgggtgacc cggagttta gagtgcagct gacggaagtt tttcagttct    5340
tccatcggca gatcgtaacc ggtgaggtgc agcaggctgt agatcagcat ggagccgtgg    5400
ccgttggaca gcacgaagcg gtcacggtca gcccaggacg gattctgcgg gttgtgtttc    5460
aggaaatcac gccacaggac ttcggcaatg tcagccatac ccataggggc cccgggtga    5520 ccggatttgg ctttctgtac tgcgtccatg ctcagcgcac gaatagcatt ggcaagctct    5580
ttacgtgagg acatttgac tccagatcgt ctagattaca gcagatcgcc gatcattttt    5640
```

```
tccagttttt cctggtcaat agcaaactta cggatacctt ccgccagttt atctactgcc    5700
attggatcct ggttgtgctg ccacaggaac tcggactcag tgatacgcgc cggacgcgct    5760
ttcacttcgc cggtgtaaga cagtttacgt tcgatagccc cttcgctctc cgccagctct    5820
ttcagcagtg ccggtgcgat ggtcagacgg tcgcagcctg ccagttccag aatttcgccg    5880
atgttacgga agcttgcgcc cataaccacg gtttcataac cgtgctcttt gtagtactgg    5940
tagatttcag atacagaaac cacgcccgga tcttctgccg gagcgtactc tttcttatcg    6000
gtattcgctt tgtaccagtc aagaatacgg ccaacaaacg gcgagatcag gaacacgccc    6060
gcttccgcac aagcacgagc ctgagcgaag gagaacagca gggtcaggtt acagttgatg    6120
ccttcttttt ccagctgttc tgcagcacgg ataccctgcc aggtagaagc cagtttgatc    6180
agaatacgat cgttgctaat accagcatcg ttgtagagtt tgatcaggcg ttttgctttc    6240
gcaattgacg cttcggtgtc ataggaaaga cgcgcatcaa cttcagttga gatacggccc    6300
ggaaccagtt tcaggatttc cagaccaata tttactgcca gtttgtcggt cgcgtccacg    6360
atctgctgcg cgcgatcgtt gctctgctgt ttcgcccagg cgacagcatc atcaatcaac    6420
ttacggtatt ccggaatctg cgctgcgtta agaatgagag aagggttggt tgtggcatcc    6480
tgcggttgat acagcttcat tgccgcgatg tccccagtgt cggccactac ggtggtgtac    6540
tgacgaaggg aggtcaattt gtccgtcatg tttattctcc taacttatta agtagctatt    6600
atattccata gctattttt aacgtgccga cttaccggcg atcgcggcca acaccttgtt    6660
cgtgatgccg actgcggtca agccgaaatg agcatataga tcattcgccg gggccgatgc    6720
accaaaaaca tcaataccat aacgaagacc atttattcca gtataccgtt cccagccaat    6780
tgtcgtccct gcttcgatcg aaacgcgtaa aattgtcgat tgaggctgat cgggcaaaac    6840
atcattacga taggattcgg gttgttgatc gaacggccta gg                      6882

<210> SEQ ID NO 10
<211> LENGTH: 18
<212> TYPE: DNA
<213> ORGANISM: artificial sequence
<220> FEATURE:
<223> OTHER INFORMATION: primer

<400> SEQUENCE: 10
atgacggaca aattgacc                                                  18

<210> SEQ ID NO 11
<211> LENGTH: 28
<212> TYPE: DNA
<213> ORGANISM: artificial sequence
<220> FEATURE:
<223> OTHER INFORMATION: primer

<400> SEQUENCE: 11
agatctgcgc aaacggacat tatcaagg                                       28

<210> SEQ ID NO 12
<211> LENGTH: 7996
<212> TYPE: DNA
<213> ORGANISM: artificial sequence
<220> FEATURE:
<223> OTHER INFORMATION: plasmid pMODPgapxylABCm

<400> SEQUENCE: 12
ggccgcggcc taggcggcca taacttcgta taatgtatgc tatacgaagt tatcctgaac    60
cgacgaccgg gtcgaatttg ctttcgaatt tctgccattc atccgcttat tatcacttat    120
```

```
tcaggcgtag caccaggcgt ttaagggcac caataactgc cttaaaaaaa ttacgccccg    180
ccctgccact catcgcagta ctgttgtaat tcattaagca ttctgccgac atggaagcca    240
tcacagacgg catgatgaac ctgaatcgcc agcggcatca gcaccttgtc gccttgcgta    300
taatatttgc ccatggtgaa acgggggcg aagaagttgt ccatattggc cacgtttaaa     360
tcaaaactgg tgaaactcac ccagggattg gctgagacga aaaacatatt ctcaataaac    420
cctttaggga ataggccag gttttcaccg taacacgcca catcttgcga atatatgtgt     480
agaaactgcc ggaaatcgtc gtggtattca ctccagagcg atgaaaacgt ttcagtttgc    540
tcatggaaaa cggtgtaaca agggtgaaca ctatcccata tcaccagctc accgtctttc    600
attgccatac ggaattccgg atgagcattc atcaggcggg caagaatgtg aataaaggcc    660
ggataaaact tgtgcttatt tttctttacg gtctttaaaa aggccgtaat atccagctga    720 acgtctggt tataggtaca ttgagcaact gactgaaatg cctcaaaatg ttctttacga     780
tgccattggg atatatcaac ggtggtatat ccagtgattt ttttctccat tttagcttcc    840
ttagctcctg aaaatctcga taactcaaaa aatacgcccg gtagtgatct tatttcatta    900
tggtgaaagt tggaacctct tacgtgccga tcaacgtctc attttcgcca aaagttggcc    960
cagggcttcc cggtatcaac agggacacca ggatttattt attctgcgaa gtgatcttcc   1020
gtcacaggat aacttcgtat aatgtatgct atacgaagtt atggcctagg cggcctctag   1080
agtcgacctg caggcatgca agcttcaggg ttgagatgtg tataagagac agctgcatta   1140
atgaatcggc caacgcgcgg ggagaggcgg tttgcgtatt gggcgctctt ccgcttcctc   1200
gctcactgac tcgctgcgct cggtcgttcg gctgcggcga gcggtatcag ctcactcaaa   1260
ggcggtaata cggttatcca cagaatcagg ggataacgca ggaaagaaca tgtgagcaaa   1320
aggccagcaa aaggccagga accgtaaaaa ggccgcgttg ctggcgtttt tccataggct   1380
ccgcccccct gacgagcatc acaaaaatcg acgctcaagt cagaggtggc gaaacccgac   1440
aggactataa agataccagg cgtttccccc tggaagctcc ctcgtgcgct ctcctgttcc   1500
gaccctgccg cttaccggat acctgtccgc ctttctccct tcgggaagcg tggcgctttc   1560
tcatagctca cgctgtaggt atctcagttc ggtgtaggtc gttcgctcca agctgggctg   1620
tgtgcacgaa ccccccgttc agcccgaccg ctgcgcctta ccggtaact atcgtcttga    1680 gtccaacccg gtaagacacg acttatcgcc actggcagca gccactggta acaggattag   1740
cagagcgagg tatgtaggcg gtgctacaga gttcttgaag tggtggccta actacggcta   1800
cactagaagg acagtatttg gtatctgcgc tctgctgaag ccagttacct tcggaaaaag   1860
agttggtagc tcttgatccg gcaaacaaac caccgctggt agcggtggtt tttttgtttg   1920
caagcagcag attacgcgca gaaaaaaagg atctcaagaa gatcctttga tcttttctac   1980
ggggtctgac gctcagtgga acgaaaactc acgttaaggg attttggtca tgagattatc   2040
aaaaaggatc ttcacctaga tccttttaaa ttaaaaatga agttttaaat caatctaaag   2100
tatatatgag taaacttggt ctgacagtta ccaatgctta atcagtgagg cacctatctc   2160
agcgatctgt ctatttcgtt catccatagt tgcctgactc cccgtcgtgt agataactac   2220
gatacgggag ggcttaccat ctggccccag tgctgcaatg ataccgcgag acccacgctc   2280
accggctcca gatttatcag caataaacca gccagccgga agggccgagc gcagaagtgg   2340
tcctgcaact ttatccgcct ccatccagtc tattaattgt tgccgggaag ctagagtaag   2400
tagttcgcca gttaatagtt tgcgcaacgt tgttgccatt gctacaggca tcgtggtgtc   2460
```

-continued

```
acgctcgtcg tttggtatgg cttcattcag ctccggttcc caacgatcaa ggcgagttac    2520
atgatccccc atgttgtgca aaaaagcggt tagctccttc ggtcctccga tcgttgtcag    2580
aagtaagttg gccgcagtgt tatcactcat ggttatggca gcactgcata attctcttac    2640
tgtcatgcca tccgtaagat gcttttctgt gactggtgag tactcaacca agtcattctg    2700
agaatagtgt atgcggcgac cgagttgctc ttgcccggcg tcaatacggg ataataccgc    2760
gccacatagc agaactttaa aagtgctcat cattggaaaa cgttcttcgg ggcgaaaact    2820
ctcaaggatc ttaccgctgt tgagatccag ttcgatgtaa cccactcgtg cacccaactg    2880
atcttcagca tcttttactt tcaccagcgt ttctgggtga gcaaaaacag gaaggcaaaa    2940
tgccgcaaaa aagggaataa gggcgacacg gaaatgttga atactcatac tcttccttttt   3000
tcaatattat tgaagcattt atcagggtta ttgtctcatg agcggataca tatttgaatg    3060
tatttagaaa aataaacaaa taggggttcc gcgcacattt ccccgaaaag tgccacctga    3120
cgtctaagaa accattatta tcatgacatt aacctataaa aataggcgta tcacgagtcg    3180
gcgtttcgg tgatgacggt gaaaacctct gacacatgca gctcccggag acggtcacag     3240
cttgtctgta agcggatgcc gggagcagac aagcccgtca gggcgcgtca gcgggtgttg    3300
gcgggtgtcg ggctggctt aactatgcgg catcagagca gattgtactg agagtgcacc     3360
atatgcggtg tgaaataccg cacagatgcg taaggagaaa ataccgcatc aggcgccatt    3420
cgccattcag gctgcgcaac tgttgggaag ggcgatcggt gcgggcctct cgctattac     3480
gccagctgtc tcttatacac atctcaacca tcatcgatga attcgagctc gcggccgcgt    3540
tcgatcaaca acccgaatcc tatcgtaatg atgttttgcc cgatcagcct caatcgacaa    3600
ttttacgcgt ttcgatcgaa gcagggacga caattggctg gaacggtat actggaataa     3660
atggtcttcg ttatggtatt gatgtttttg gtgcatcggc cccggcgaat gatctatatg    3720
ctcatttcgg cttgaccgca gtcggcatca cgaacaaggt gttggccgcg atcgccggta    3780
agtcggcacg ttaaaaaata gctatggaat ataatagcta cttaataagt taggagaata    3840
aacatgcaag cctatttga ccagctcgat cgcgttcgtt atgaaggctc aaaatcctca     3900
aacccgttag cattccgtca ctacaatccc gacgaactgg tgttgggtaa gcgtatggaa    3960
gagcacttgc gttttgccgc ctgctactgg cacaccttct gctggaacgg ggcggatatg    4020
tttggtgtgg gggcgtttaa tcgtccgtgg cagcagcctg gtgaggcact ggcgttggcg    4080
aagcgtaaag cagatgtcgc atttgagttt ttccacaagt tacatgtgcc attttattgc    4140
ttccacgatg tggatgtttc ccctgagggc gcgtcgttaa aagagtacat caataatttt    4200
gcgcaaatgg ttgatgtcct ggcaggcaag caagaagaga gcggcgtgaa gctgctgtgg    4260
ggaacggcca actgctttac aaaccctcgc tacggcgcgg gtgcggcgac gaacccagat    4320
cctgaagtct tcagctgggc ggcaacgcaa gttgttacag cgatggaagc aacccataaa    4380
ttgggcggtg aaaactatgt cctgtggggc ggtcgtgaag gttacgaaac gctgttaaat    4440
accgacttgc gtcaggagcg tgaacaactg ggccgcttta tgcagatggt ggttgagcat    4500
aaacataaaa tcggtttcca gggcacgttg cttatcgaac cgaaccgcca agaaccgacc    4560
aaacatcaat atgattacga tgccgcgacg gtctatggct tcctgaaaca gtttggtctg    4620
gaaaaagaga ttaaactgaa cattgaagct aaccacgcga cgctggcagg tcactctttc    4680
catcatgaaa tagccaccgc cattgcgctt ggcctgttcg gttctgtcga cgccaaccgt    4740
ggcgatgcgc aactgggctg ggacaccgac cagttcccga acagtgtgga agagaatgcg    4800
ctggtgatgt atgaaattct caaagcaggc ggtttcacca ccggtggtct gaacttcgat    4860
```

```
gccaaagtac gtcgtcaaag tactgataaa tatgatctgt tttacggtca tatcggcgcg    4920
atggatacga tggcactggc gctgaaaatt gcagcgcgca tgattgaaga tggcgagctg    4980
gataaacgca tcgcgcagcg ttattccggc tggaatagcg aattgggcca gcaaatcctg    5040
aaaggccaaa tgtcactggc agatttagcc aaatatgctc aggaacatca tttgtctccg    5100
gtgcatcaga gtggtcgcca ggaacaactg gaaaatctgg taaaccatta tctgttcgac    5160
aaataacggc taactgtgca gtccgttggc ccggttatcg gtagcgatac cgggcatttt    5220
tttaaggaac gatcgatatg tatatcggga tagatcttgg cacctcgggc gtaaaagtta    5280
ttttgctcaa cgagcagggt gaggtggttg ctgcgcaaac ggaaaagctg accgtttcgc    5340
gcccgcatcc actctggtcg gaacaagacc cggaacagtg gtggcaggca actgatcgcg    5400
caatgaaagc tctgggcgat cagcattctc tgcaggacgt taaagcattg ggtattgccg    5460
gccagatgca cggagcaacc ttgctggatg ctcagcaacg ggtgttacgc cctgccattt    5520
tgtggaacga cgggcgctgt gcgcaagagt gcactttgct ggaagcgcga gttccgcaat    5580
cgcgggtgat taccggcaac ctgatgatgc ccggatttac tgcgcctaaa ttgctatggg    5640
ttcagcggca tgagccggag atattccgtc aaatcgacaa agtattatta ccgaaagatt    5700
acttgcgtct gcgtatgacg ggggagtttg ccagcgatat gtctgacgca gctggcacca    5760
tgtggctgga tgtcgcaaag cgtgactgga gtgacgtcat gctgcaggct tgcgacttat    5820
ctcgtgacca gatgcccgca ttatacgaag gcagcgaaat tactggtgct tgttacctg     5880 aagttgcgaa agcgtggggt atggcgacgg tgccagttgt cgcaggcggt ggcgacaatg    5940
cagctggtgc agttggtgtg ggaatggttg atgctaatca ggcaatgtta tcgctgggga    6000
cgtcgggggt ctattttgct gtcagcgaag ggttcttaag caagccagaa agcgccgtac    6060
atagcttttg ccatgcgcta ccgcaacgtt ggcatttaat gtctgtgatg ctgagtgcag    6120
cgtcgtgtct ggattgggcc gcgaaattaa ccggcctgag caatgtccca gctttaatcg    6180
ctgcagctca acaggctgat gaaagtgccg agccagtttg gtttctgcct tatctttccg    6240
gcgagcgtac gccacacaat aatccccagg cgaaggggg tttctttggt ttgactcatc     6300
aacatggccc caatgaactg gcgcgagcag tgctggaagg cgtgggttat gcgctggcag    6360
atggcatgga tgtcgtgcat gcctgcggta ttaaaccgca aagtgttacg ttgattgggg    6420
gcggggcgcg tagtgagtac tggcgtcaga tgctggcgga tatcagcggt cagcagctcg    6480
attaccgtac gggggggggat gtggggccag cactgggcgc agcaaggctg gcgcagatcg    6540
cggcgaatcc agagaaatcg ctcattgaat tgttgccgca actaccgtta aacagtcgc     6600 atctaccaga tgcgcagcgt tatgccgctt atcagccacg acgagaaacg ttccgtcgcc    6660
tctatcagca acttctgcca ttaatggcgt aaacgttatc ccctgcctga ccgggtgggg    6720
gataattcac atctatatat ctcagtaatt aattaatatt tagtatgaat ttattctgaa    6780
aatcatttgt taatggcatt tttcagtttt gtctttcgtt ggttactcgt aatgtatcgc    6840
tggtagatat ggagatcgtt atgaaaacct caaagactgt ggcaaaacta ttatttgttg    6900
tcggggcgct ggtttatctg gttgggctat ggatctcatg cccattgtta agtggaaaag    6960 gctatttct tggcgtgtta atgacagcaa cttttggcaa ctatgcaagc ttgtttggtg     7020
cagtagcggt gcagaaaaat attcgtgatg ccggaataaa cccaccaaaa gaaacacagg    7080
ttacccagga agaatacagc gaataactca cgtaagcccg gtcagtccaa tgtgaccggg    7140
cttttactta actcactaat ctgtttctgt cgattcgttg taccagcata gaaagtaaca    7200
```

-continued

```
aactcgctgc caacgtcgcg caaaagatcc aaataatatc cagtattggc caattttttaa    7260
gctcaattcc ccgggtgcgc agcgcatgga taatcaaggc gtggaatccg tatatacccca   7320
atgaatggcg ggagattaag ccaagtccgc gaatggtacg cgtatccagc gtgttttttaa   7380
ccagagtcaa tagcgcgatt gcgcagataa aaaccatcgg cccacagtaa agataccagg    7440
tatcggcaaa atttccgcgc cactgcaatt catataatgt cccgcgagag ataataaaaa    7500
cccccgtcgc aaacagcgcg gcgttcaccc acgacagtgc tttatgctgt gtgtccatca    7560
tccctatagc gcggcccaac atgccataca gaatgtagta aaaagtatcg ccattgatat    7620
ataagttaat tggcagccat tcaaaaccgt caattttctg cggcactgtg tttgggttag    7680
cgataatgcc aatcaccgcc attagcacca gcaacatttt tccgccgacg ttcttcacct    7740
gaatcagcgt tgaaaccaga taaatcaccg caatcgcgaa gaaaaccac aagtggtaaa     7800
acactggctt ttgcagcagg tttttcagcg ctaactccat attgatggag gtaaacagcg    7860
caatgtagag cagtgcgatt gcgctataaa aaatcagaca taagccgata cgcaagaaat    7920
ggcgcggctg ggcgctgcgt tcgccaaaaa agagatagcc ggaaatcatg aaaaatagcg    7980
gcacgctgac acgagc                                                    7996
```

```
<210> SEQ ID NO 13
<211> LENGTH: 24
<212> TYPE: DNA
<213> ORGANISM: artificial sequence
<220> FEATURE:
<223> OTHER INFORMATION: primer

<400> SEQUENCE: 13
cgatcaacaa cccgaatcct atcg                                             24

<210> SEQ ID NO 14
<211> LENGTH: 26
<212> TYPE: DNA
<213> ORGANISM: artificial sequence
<220> FEATURE:
<223> OTHER INFORMATION: primer

<400> SEQUENCE: 14
gccgttattt gtcgaacaga taatgg                                           26

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
tatgggttca gcggcatgag                                                  20

<210> SEQ ID NO 16
<211> LENGTH: 21
<212> TYPE: DNA
<213> ORGANISM: artificial sequence
<220> FEATURE:
<223> OTHER INFORMATION: primer

<400> SEQUENCE: 16
atgggcatga gatccatagc c                                                21
```

ETHANOL PRODUCTION IN FERMENTATION OF MIXED SUGARS CONTAINING XYLOSE

This application claims the benefit of U.S. Provisional Application No. 60/847,997, filed Sep. 28, 2006, which is incorporated in its entirety as a part hereof for all purposes.

STATEMENT OF GOVERNMENT RIGHTS

This invention was made with United States government support under Contract Nos. 04-03-CA-70224 and DE-FC36-03GO13146 awarded by the Department of Energy. The government has certain rights in this invention.

FIELD OF INVENTION

The invention relates to the fields of microbiology and genetic engineering. More specifically, a method of improving ethanol production during fermentation of xylose-containing mixed sugars was developed.

BACKGROUND

Fuel ethanol produced from renewable resources is one of the long-term solutions to global fossil fuel shortages, rising energy costs, and global warming effects related to increased atmospheric carbon dioxide. Fuel ethanol from renewable resources is produced by fermentation of sugars. Currently in the United States, glucose derived from corn grain is the most abundant sugar source for ethanol production. Due to the demands for corn grain as a feed and food supply, methods of converting various types of cellulosic biomass (including hemicellulose) to fermentable sugars are being developed. Sugar derived from this biomass source is a mixture of hexoses and pentoses, primarily glucose and xylose. As a result of developments in cellulosic biomass processing, these sugars may be released in high concentrations and used in fermentation in high concentrations to produce ethanol, with reduced water consumption and higher throughput. As such, conversion of biomass to ethanol poses great possibility for improving environmental impacts compared to fossil fuel ethanol production. Further, it provides a potentially economically viable alternative to fossil fuel ethanol production.

In addition to improvements in biomass processing, genetic engineering has been used to make improvements in microorganisms that are able to produce ethanol. In order to enhance the utilization of sugars from cellulosic biomass, the ethanologen Zymomonas (i.e., Z. mobilis) has been made capable of utilizing xylose by engineering strains for expression of four enzymes: 1) xylose isomerase, which catalyses the conversion of xylose to xylulose; 2) xylulokinase, which phosphorylates xylulose to form xylulose 5-phosphate; 3) transketolase; and 4) transaldolase (U.S. Pat. Nos. 5,514,583, 6,566,107; Zhang et al. (1995) Science 267:240-243). Though these strains do metabolize xylose, at high xylose concentration the xylose is not fully utilized, so that the theoretical ethanol yield is not achieved. The ethanol yield also is limited due to synthesis of xylitol as a by-product of xylose metabolism (Feldmann et al. (1992) Appl Microbiol Biotechnol 38: 354-361; Kim et al. (2000) Applied and Environmental Microbiology 66:186-193). Xylitol is toxic to cells due to its phosphorylation to xylitol 5-phosphate, which is a compound that accumulates in the cell and inhibits growth. The yield of ethanol is also reduced due to the synthesis of xylitol, since xylose-utilizing recombinant strains of Z. mobilis cannot convert xylitol to ethanol. In addition, xylitol is a potent inhibitor of xylose isomerase, which catalyzes the first step of xylose utilization in the engineered xylose metabolism pathway. Therefore, fermentations in high sugar medium including xylose, with xylose-utilizing Z. mobilis, do not achieve maximal xylose usage and ethanol production.

Complete use of 8% xylose in a sugars mixture with 4% glucose, by xylose utilizing Z. mobilis, took 2-3 days (Lawford and Rousseau (1999) Appl Biochem and Biotech. 77-79: 235-249). Complete use of 65 g/L xylose in a mixture with 65 g/L glucose required 48 hours (Joachimsthal and Rogers (2000) Appl Biochem and Biotechnol 84-86: 343-356), and using higher concentrations of sugars (75 g/L xylose and 75 g/L glucose) resulted in incomplete xylose utilization.

Sorbitol has been added as an osmoprotectant to enhance growth of non-engineered Z. mobilis in high concentrations of glucose (Loos et al. (1994) J Bacteriol 176:7688-7693). Sorbitol was accumulated intracellularly. In addition, sorbitol was shown to be produced by the cells and accumulated when growing on high sucrose. Any effects of sorbitol on production of ethanol by Z. mobilis strains that are engineered to utilize xylose, when grown in the presence of a sugar mixture including xylose, have not been determined previously.

There remains a need to develop fermentation conditions that enhance ethanol production in sugar media including xylose, allowing xylose-utilizing strains to reach their maximal ethanol production capacity with maximal xylose utilization in reduced time.

SUMMARY OF INVENTION

The present invention provides a method for improving the production of ethanol made by fermentation. In the instant method, Zymomonas mobilis cells that have been engineered to express genes involved in xylose utilization are grown in a medium containing mixed sugars, including xylose and at least one additional sugar. The medium also includes sorbitol, mannitol, galactitol, or ribitol (also called adonitol), which results in increased xylose utilization and increased ethanol production. Production of the by-product xylitol is also reduced. In one embodiment of the invention the method comprises:
  a) providing recombinant Zymomonas cells capable of converting xylose to ethanol;
  b) providing a suitable medium comprising (i) a mixed sugar composition comprising xylose and at least one additional sugar, and (ii) at least one sugar alcohol selected from the group consisting of sorbitol, mannitol, galactitol, and ribitol; and
  c) contacting (a) with (b) whereby the Z. mobilis cells produce ethanol.

In certain embodiments the contacting of step (c) above occurs for at least about 24 hours. The contacting above may occur at a temperature of about 25° C. to about 40° C., or about 30° C. to about 37° C. The contacting above may occur at a pH of about 4.5 to about 7.5, or a pH of about 5.0 to about 6.0.

In another embodiment, the contacting occurs by inoculating the cells of (a) into the medium of (b) using an inoculation ratio that is between about 0.01% and about 20% (v/v), or about 0.1% and about 20%.

In one embodiment the xylose and at least one additional sugar are produced from biomass that has been treated and/or saccharified.

In another embodiment the mixed sugar composition comprises at least about 10% xylose, or in an alternate embodiment the mixed sugar composition comprises about 40% to about 60% xylose.

In another embodiment the contacting of (a) and (b) occurs under fermentation conditions without supplying gases.

Another aspect of the invention is the xylose-utilizing *Z. mobilis* strain referred to herein as ZW658, ATCC Deposit No. PTA-7858, deposited Sep. 12, 2006.

BRIEF DESCRIPTION OF THE FIGURES, SEQUENCE DESCRIPTIONS AND BIOLOGICAL DEPOSITS

The invention can be more fully understood from the following detailed description, the figures, and the accompanying sequence descriptions that form a part of this application.

Figure 7:
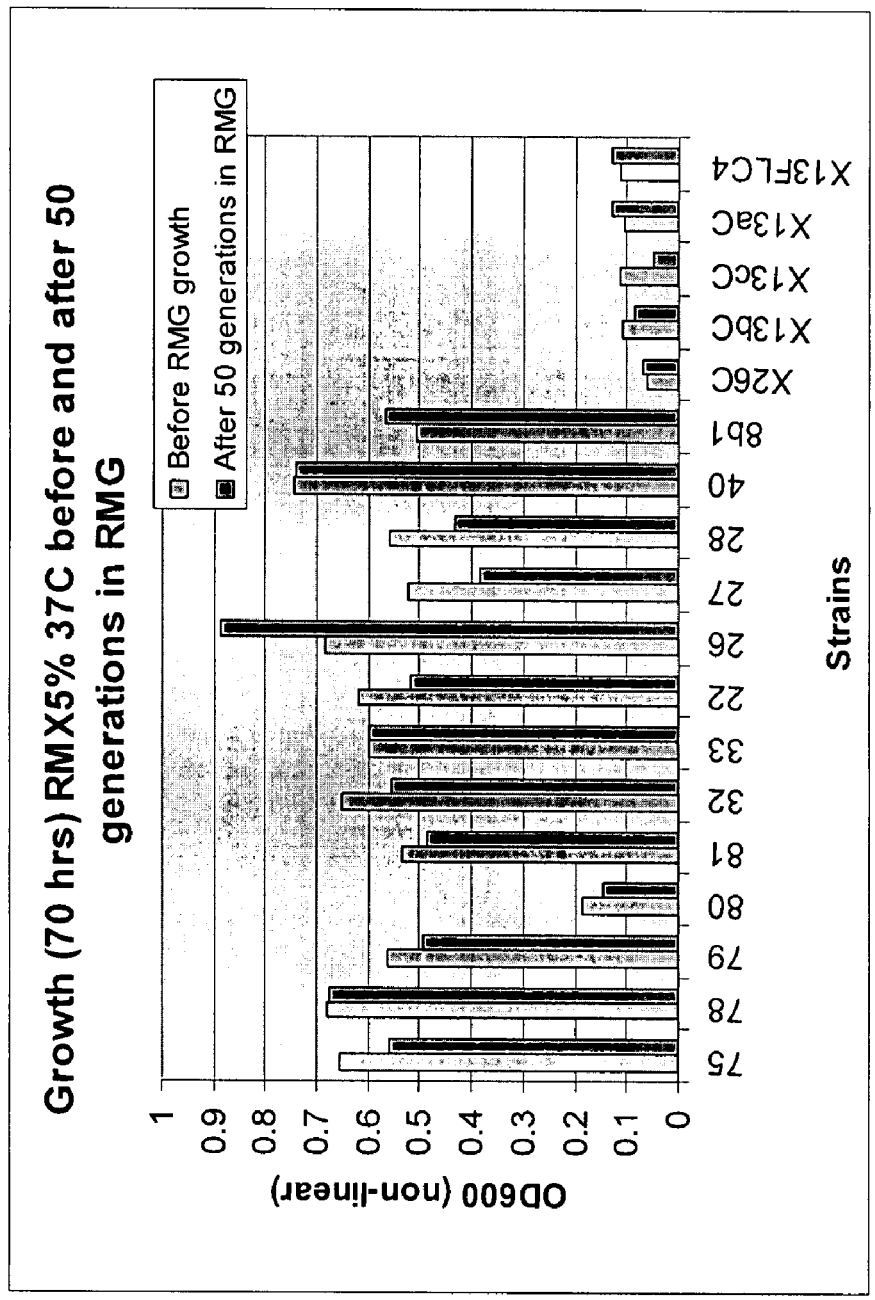

FIG. 7 shows a graph of growth of adapted xylose-utilizing strains at 70 hr on RM (rich medium) with 5% xylose (RMX5%) before and after growing 50 generations in RM with 5% glucose (RMG).

Figure 8:
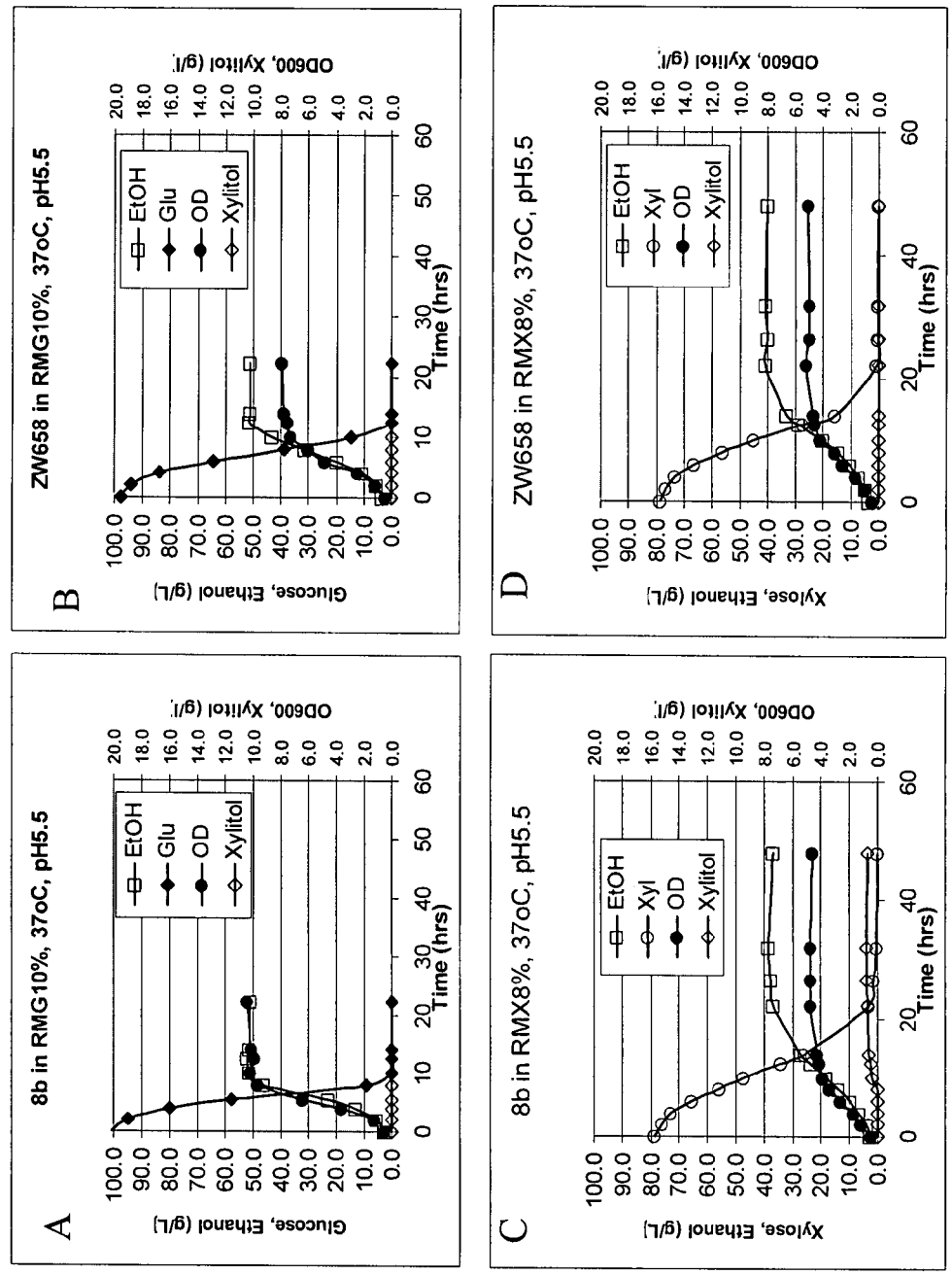

FIG. 8 shows graphs of growth, glucose or xylose utilization, and ethanol and xylitol production for the selected strain, ZW658 in comparison to the control, 8b, in RM+10% glucose (RMG10%) (A, B) and RM+8% xylose (RMX8%) (C, D).

Figure 9:
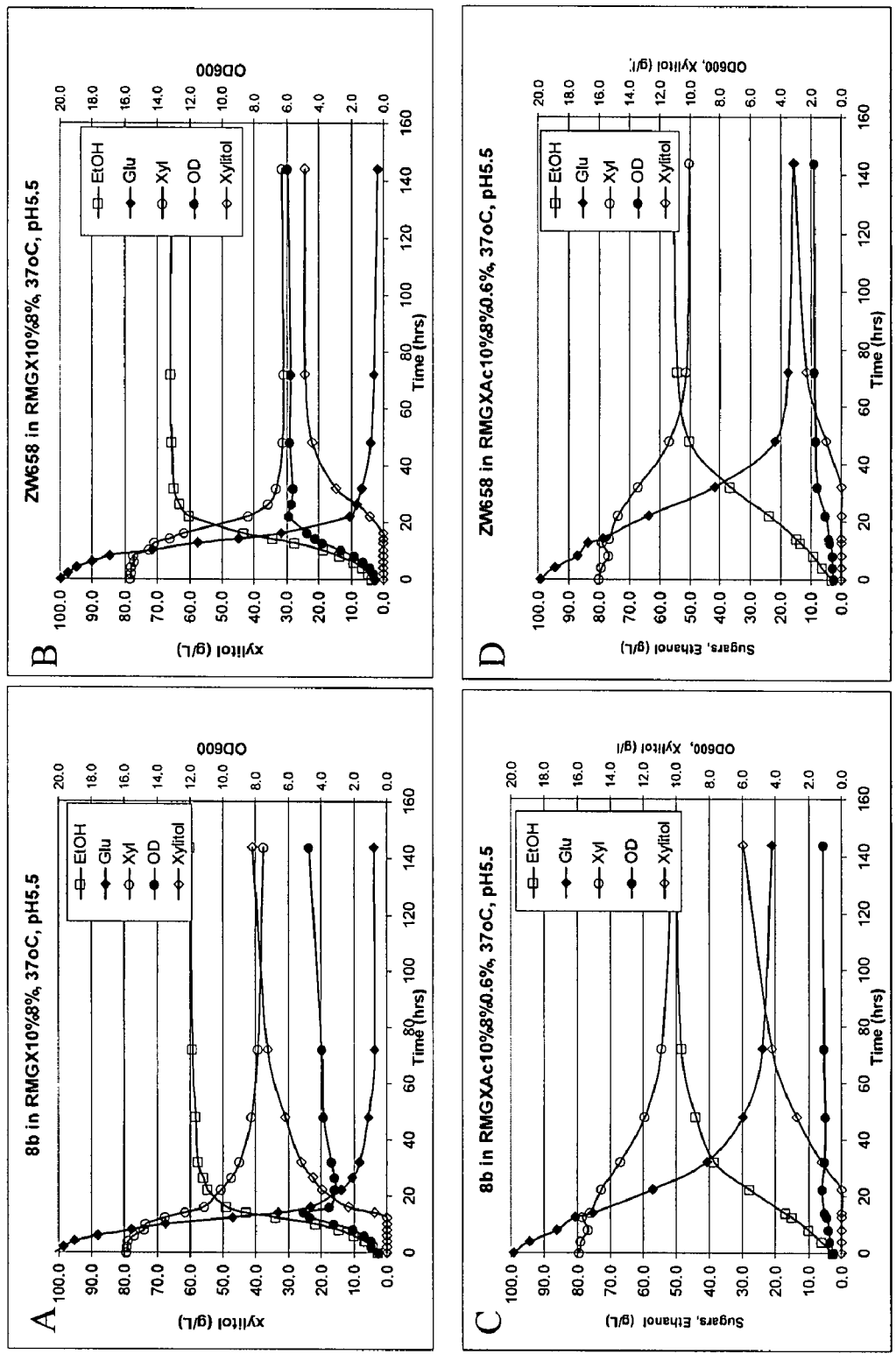

FIG. 9 shows graphs of growth, glucose and xylose utilization, and ethanol and xylitol production for the selected strain, ZW658 in comparison to the control, 8b, in RM+10% glucose and 8% xylose without acetate (A, B) or with 0.6% acetate (C, D).

Figure 10:
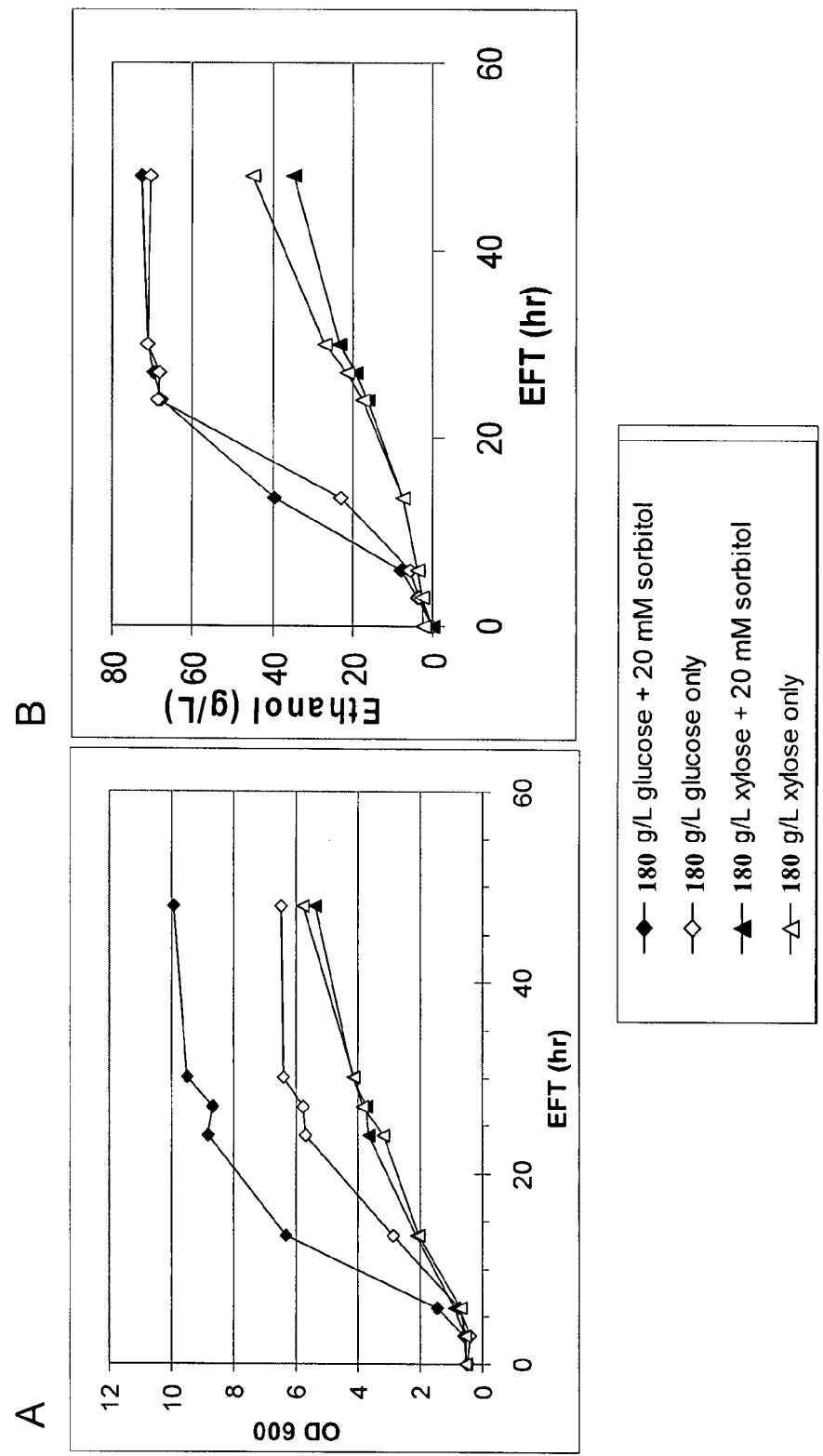

FIG. 10 shows graphs of the effects of sorbitol on growth (A) and ethanol production (B) on xylose-utilizing *Z. mobilis* grown on glucose alone or xylose alone.

Figure 11:
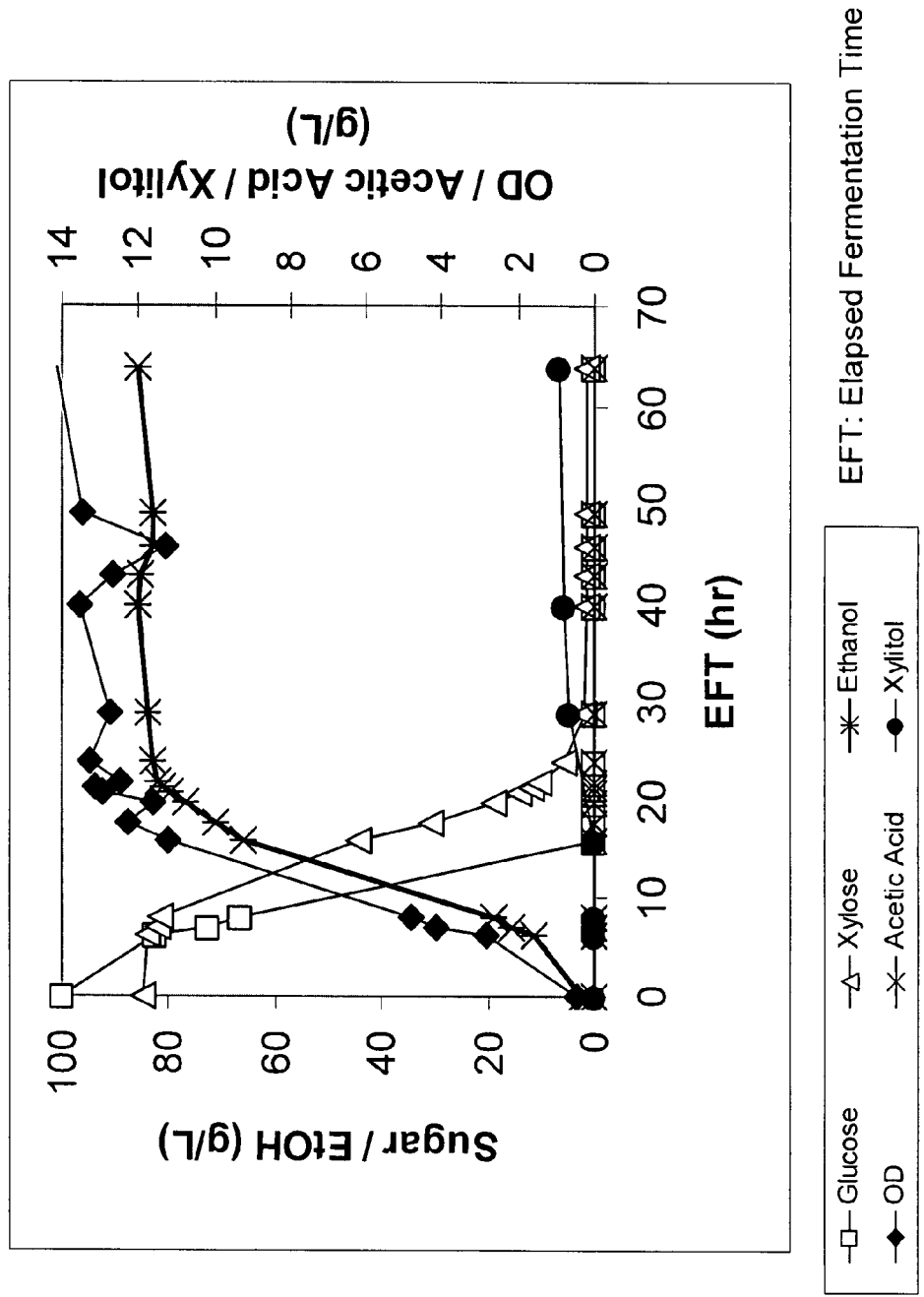

FIG. 11 shows a graph of the growth, glucose utilization, xylose utilization, ethanol production, acetic acid production and xylitol production of xylose-utilizing *Z. mobilis* grown on glucose and xylose mixed sugar in the presence of sorbitol.

Figure 12:
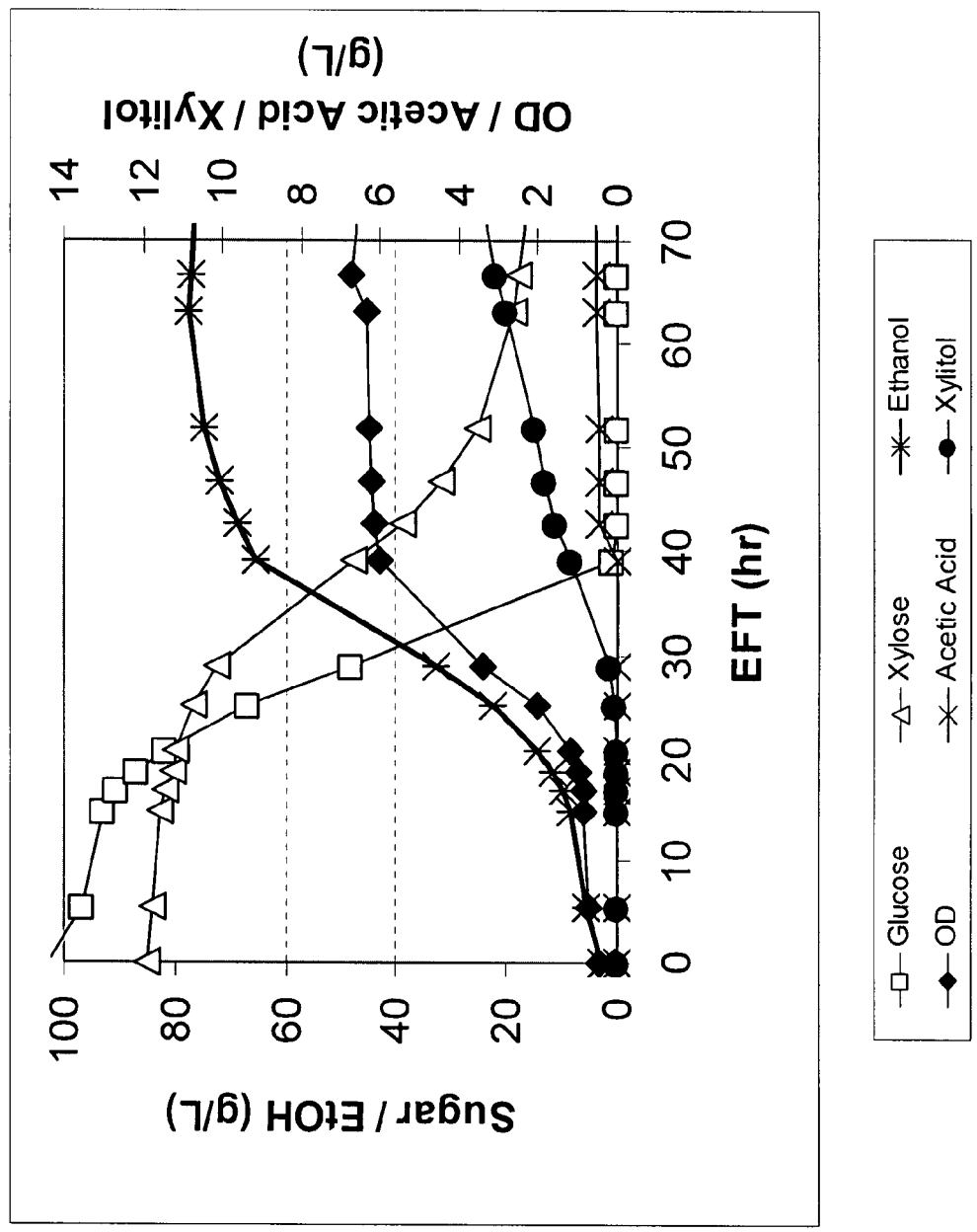

FIG. 12 shows a graph of the growth, glucose utilization, xylose utilization, ethanol production, acetic acid concentration and xylitol production of xylose-utilizing *Z. mobilis* grown on glucose and xylose mixed sugar in the absence of sorbitol.

Figure 13:
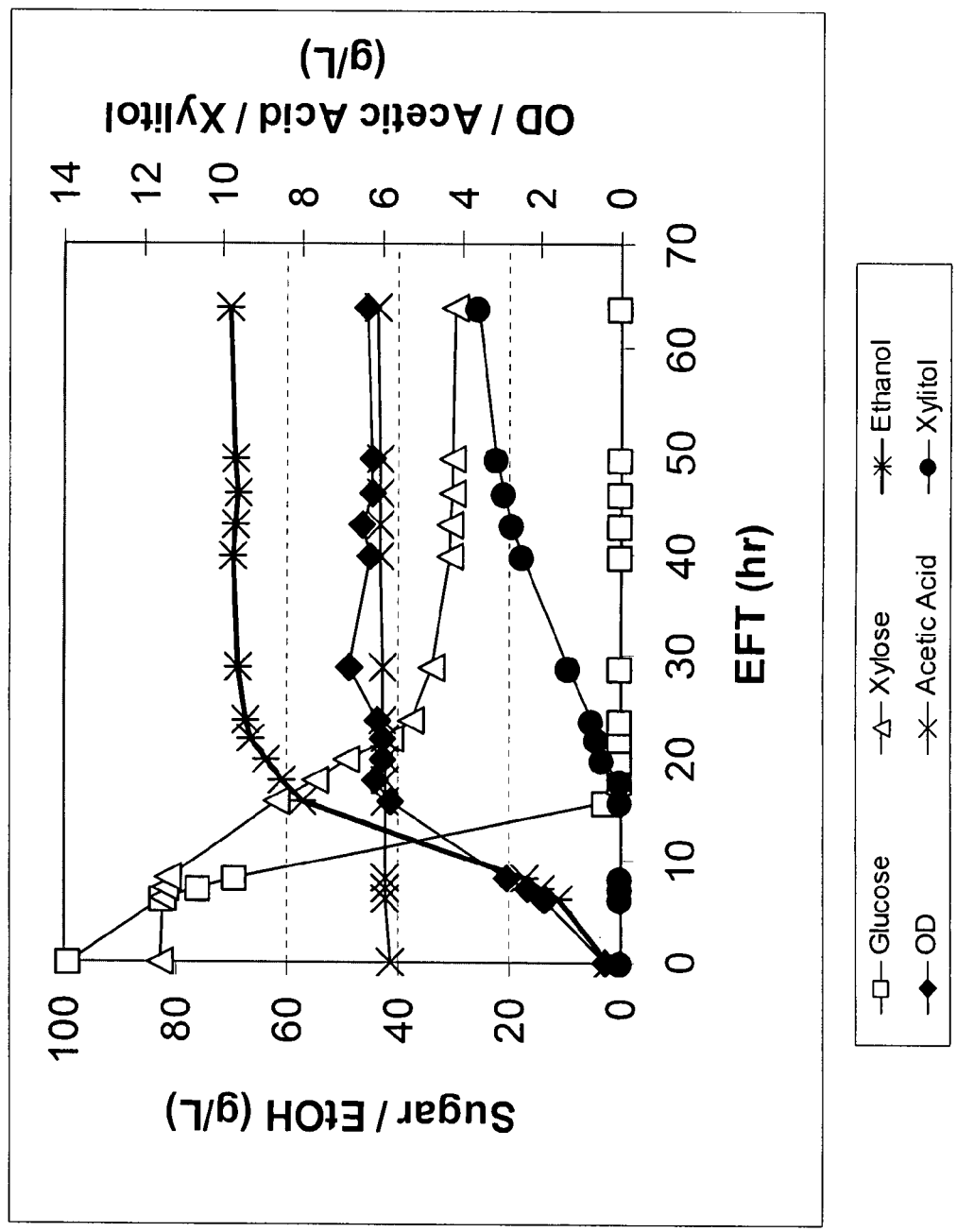

FIG. 13 shows a graph of the growth, glucose utilization, xylose utilization, ethanol production, acetic acid concentration and xylitol production of xylose-utilizing *Z. mobilis* grown on glucose and xylose mixed sugar in the presence of acetate and sorbitol.

Figure 14:
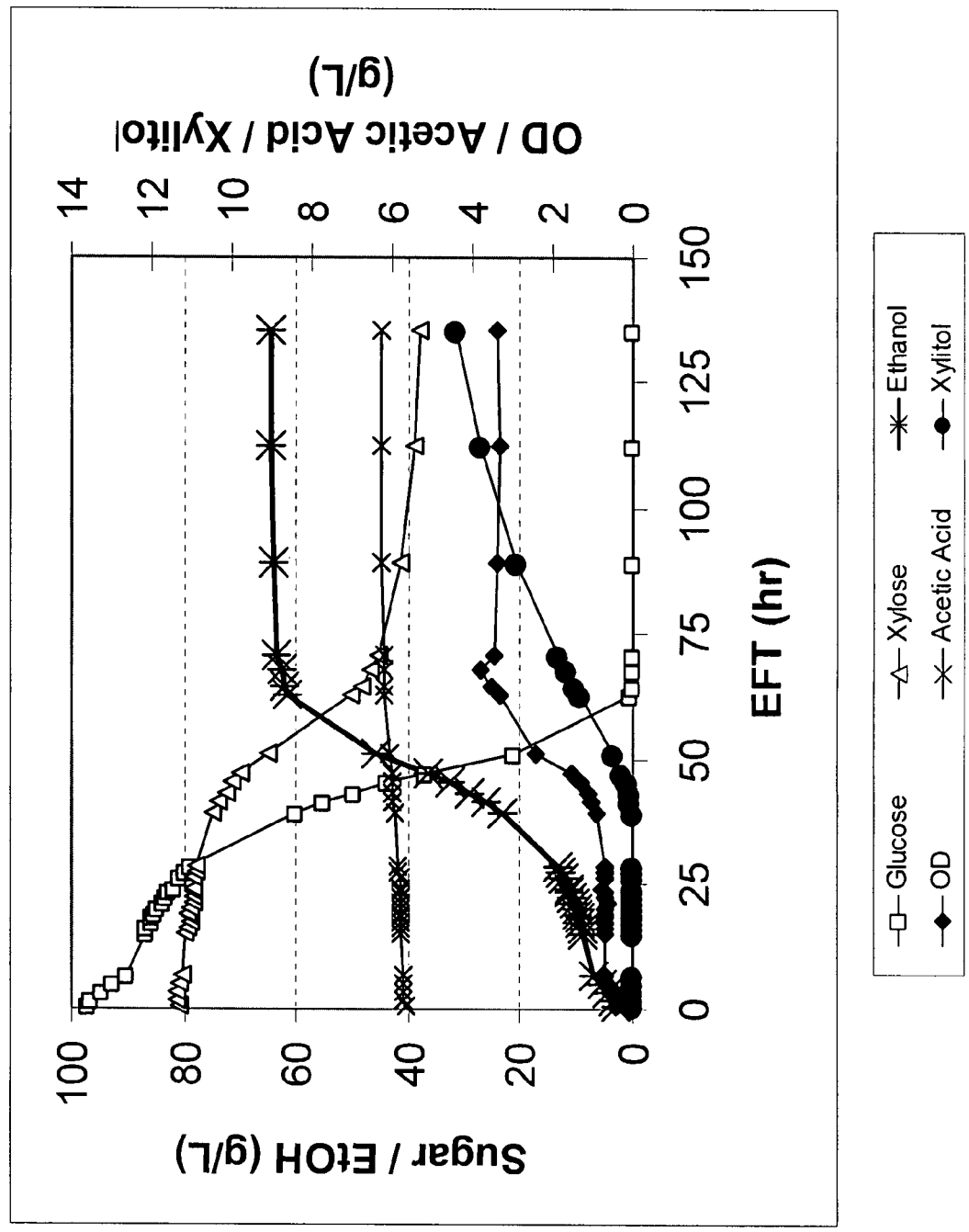

FIG. 14 shows a graph of the growth, glucose utilization, xylose utilization, ethanol production, acetic acid concentration and xylitol production of xylose-utilizing *Z. mobilis* grown on glucose and xylose mixed sugar in the presence of acetate and absence of sorbitol.

Figure 15:
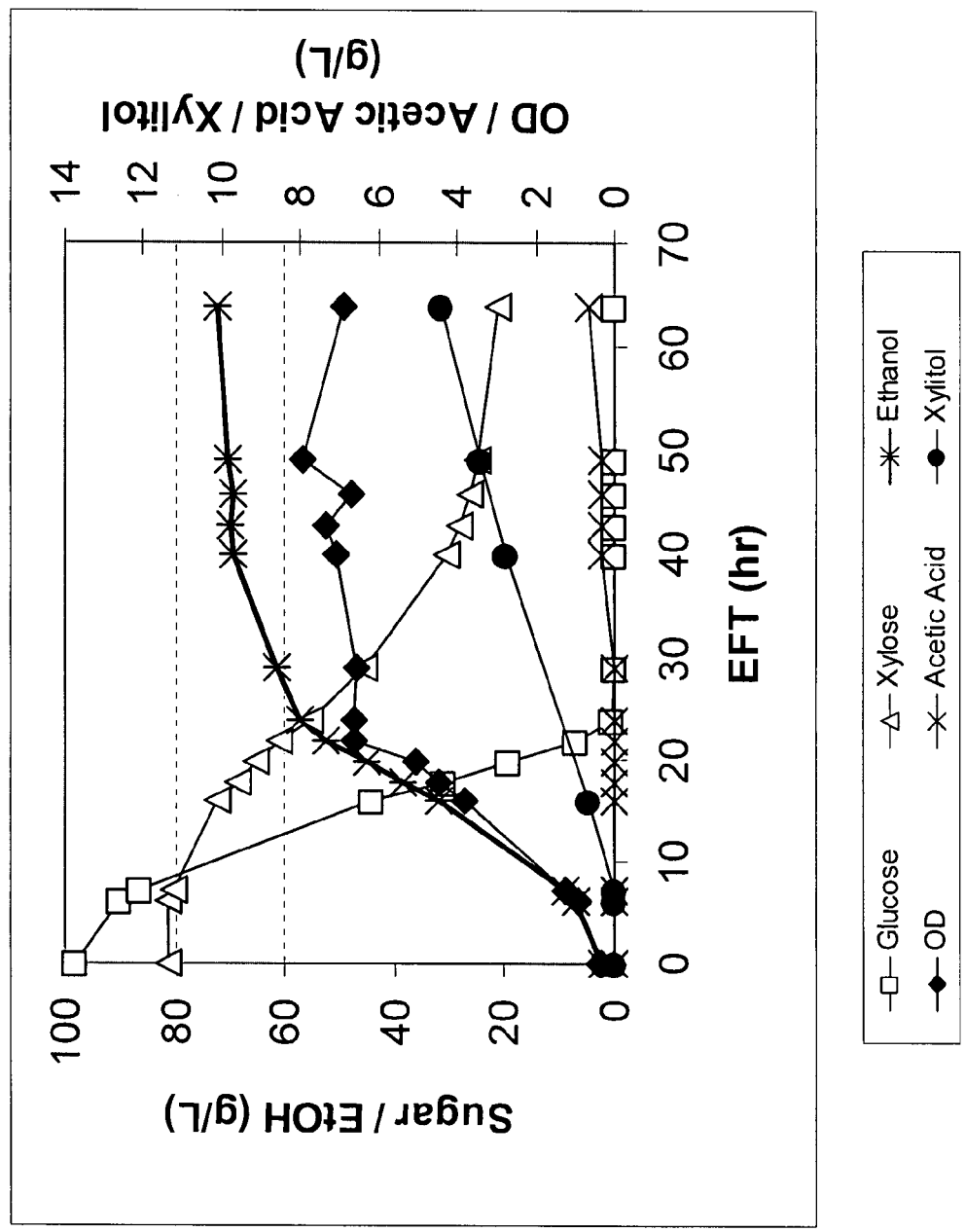

FIG. 15 shows a graph of the growth, glucose utilization, xylose utilization, ethanol production, acetic acid concentration and xylitol production of xylose-utilizing *Z. mobilis* grown on glucose and xylose mixed sugar in the presence of glutamate.

Figure 16:
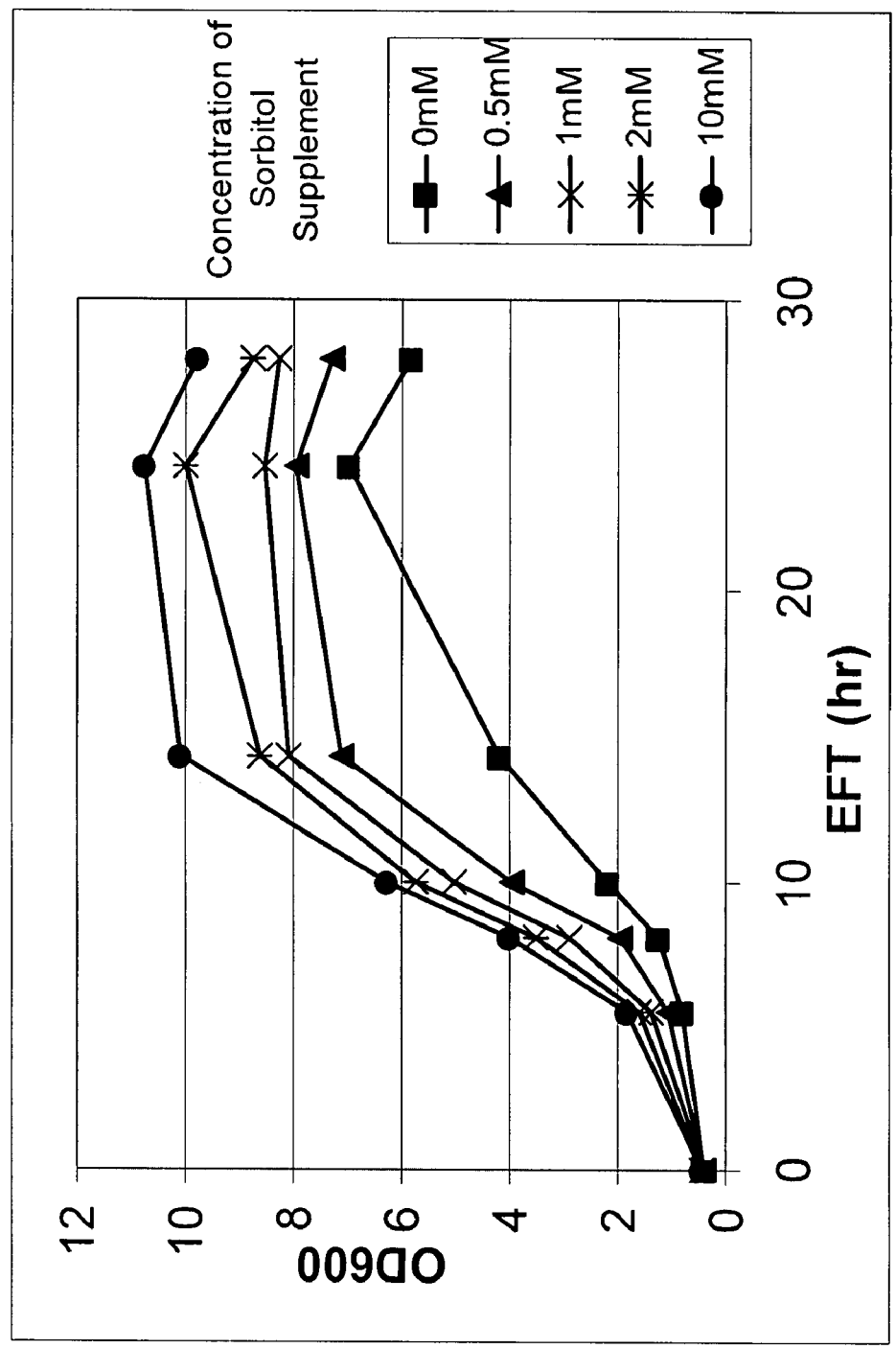

FIG. 16 shows a graph of the growth of xylose-utilizing *Z. mobilis* grown on glucose and xylose mixed sugar in the presence of varying amounts of sorbitol between 0 and 10 mM.

Figure 17:
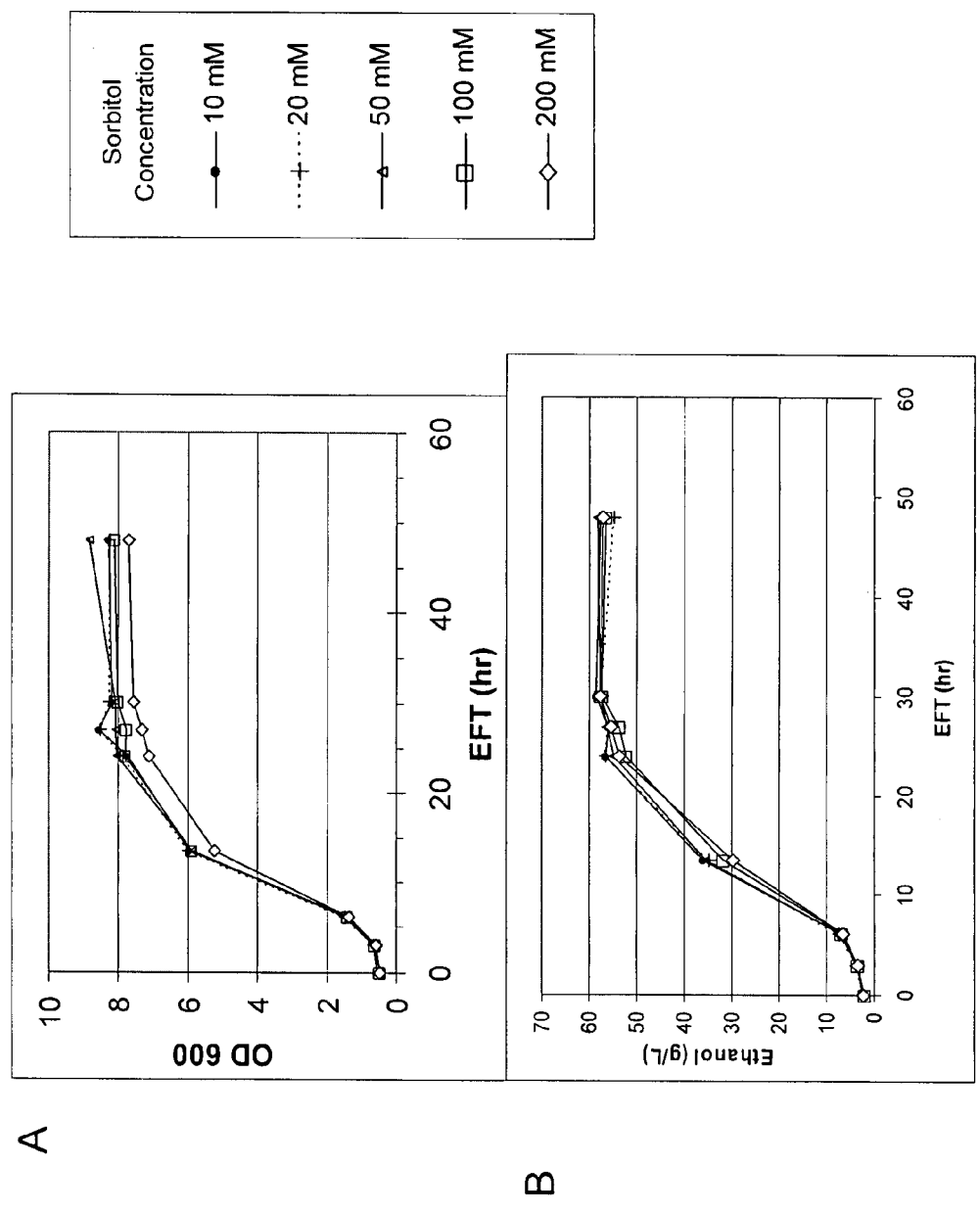

FIG. 17 shows graphs of the growth (A) and ethanol production (B) of xylose-utilizing *Z. mobilis* grown on glucose and xylose mixed sugar in the presence of varying amounts of sorbitol between 10 mM and 200 mM.

Figure 18:
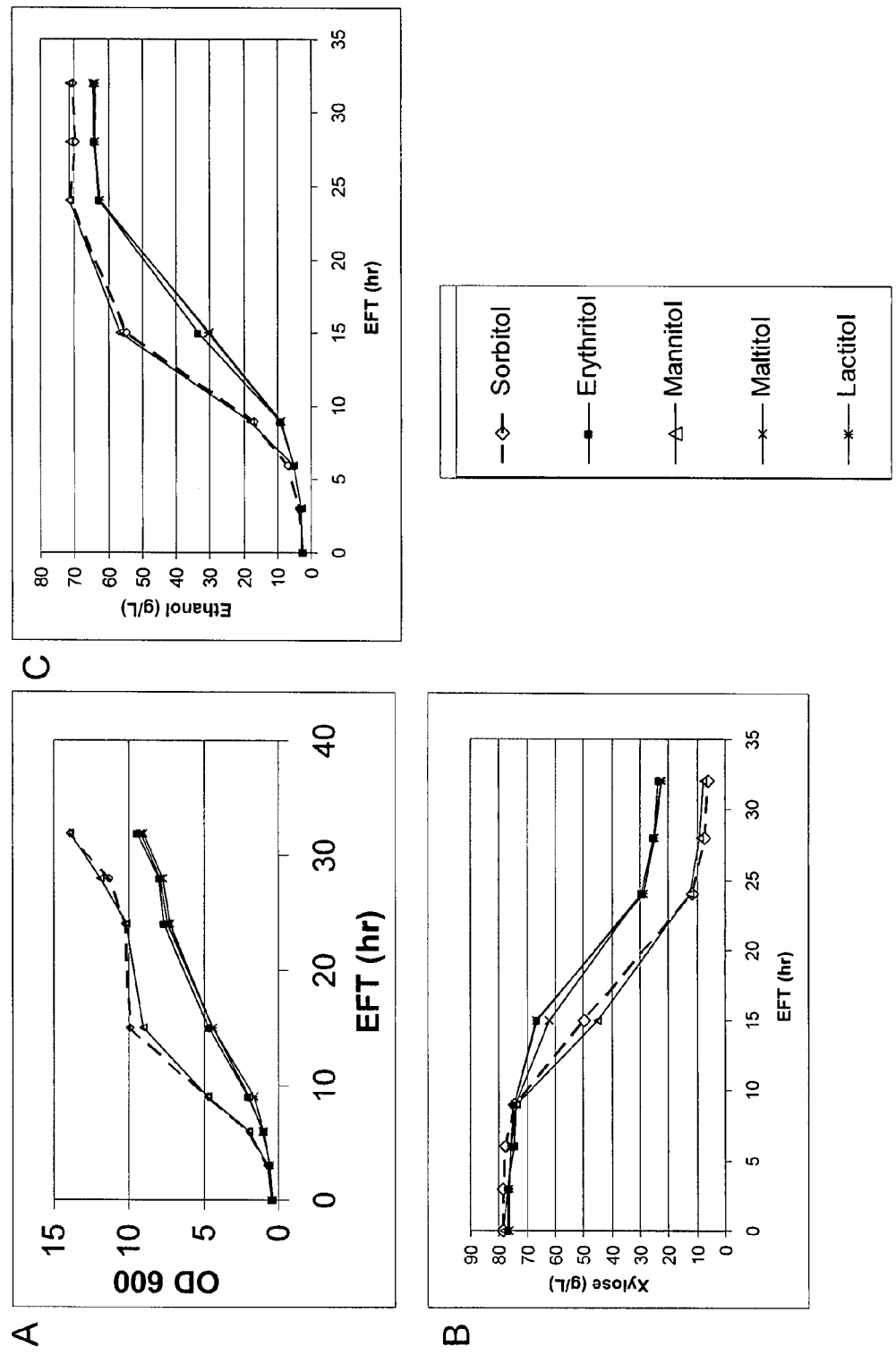

FIG. 18 shows graphs of growth (A), xylose utilization (B), and ethanol production (C) in the presence of different polyols.

Figure 19:
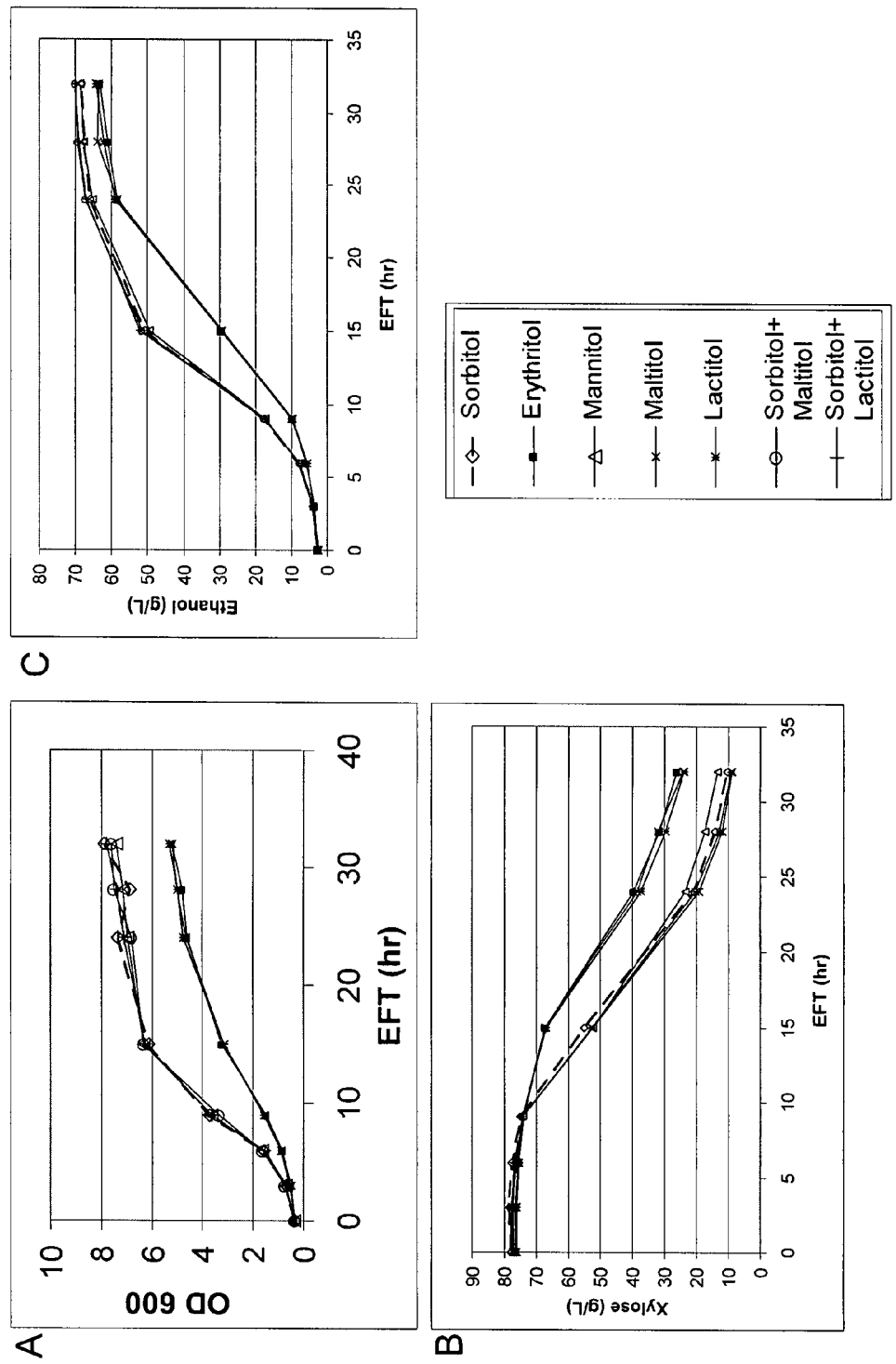

FIG. 19 shows graphs of growth (A), xylose utilization (B), and ethanol production (C) in the presence of acetate and different polyols.

Figure 20:
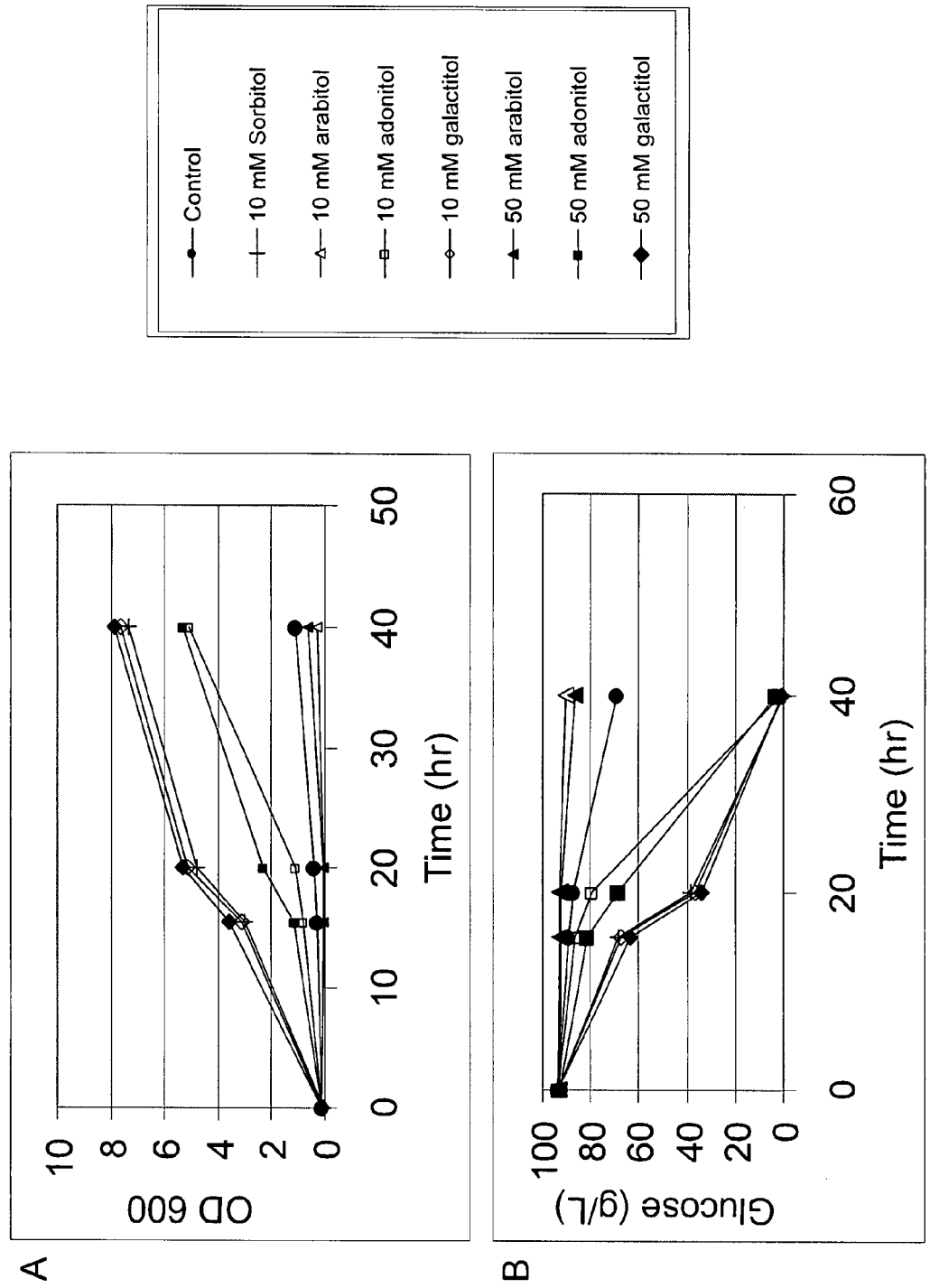

FIG. 20 shows graphs of growth (A) and glucose utilization (B) in the presence of different sugar alcohols.

Figure 21:
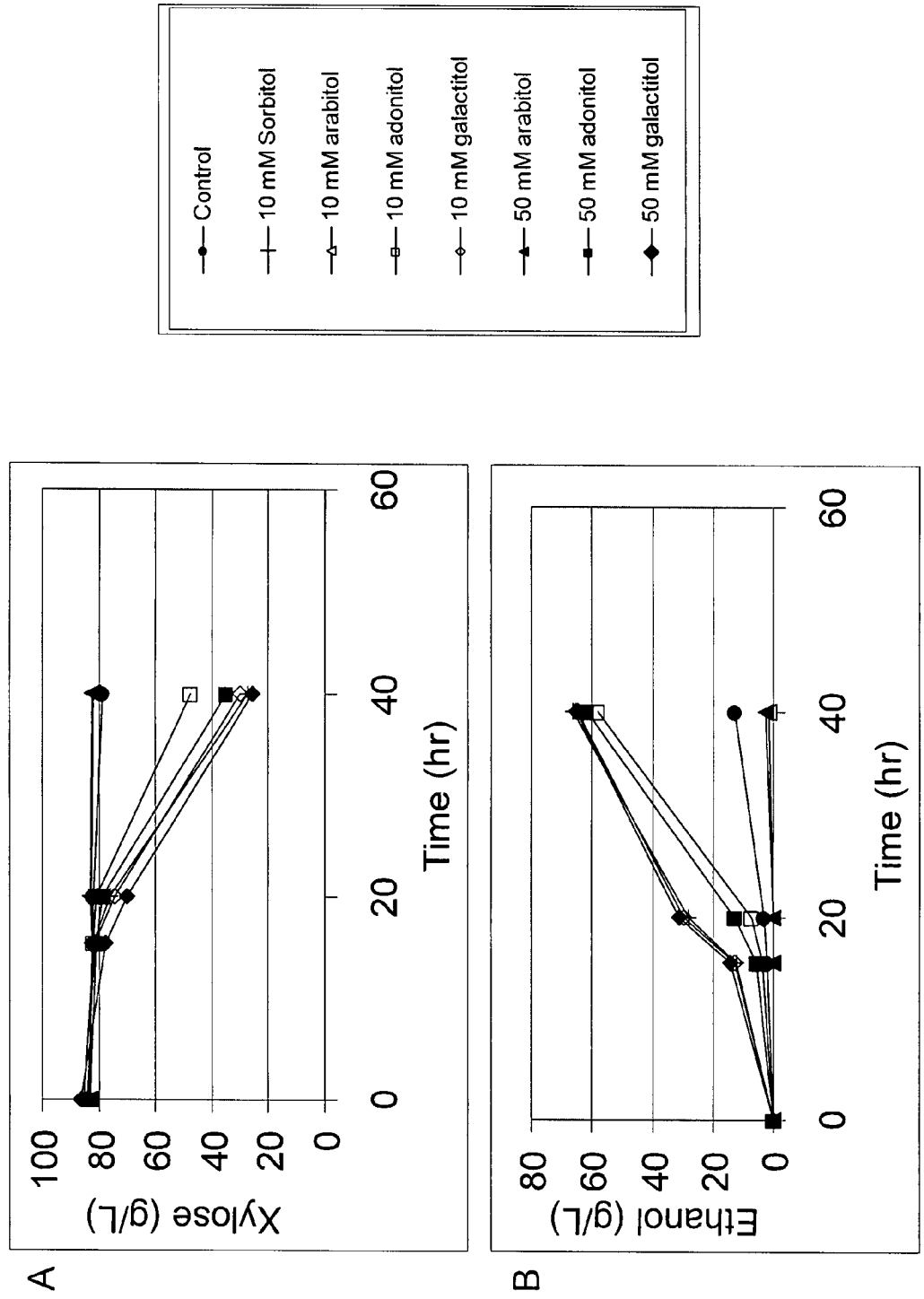

FIG. 21 shows graphs of xylose utilization (A) and ethanol production (B) in the presence of different sugar alcohols.

Figure 22:
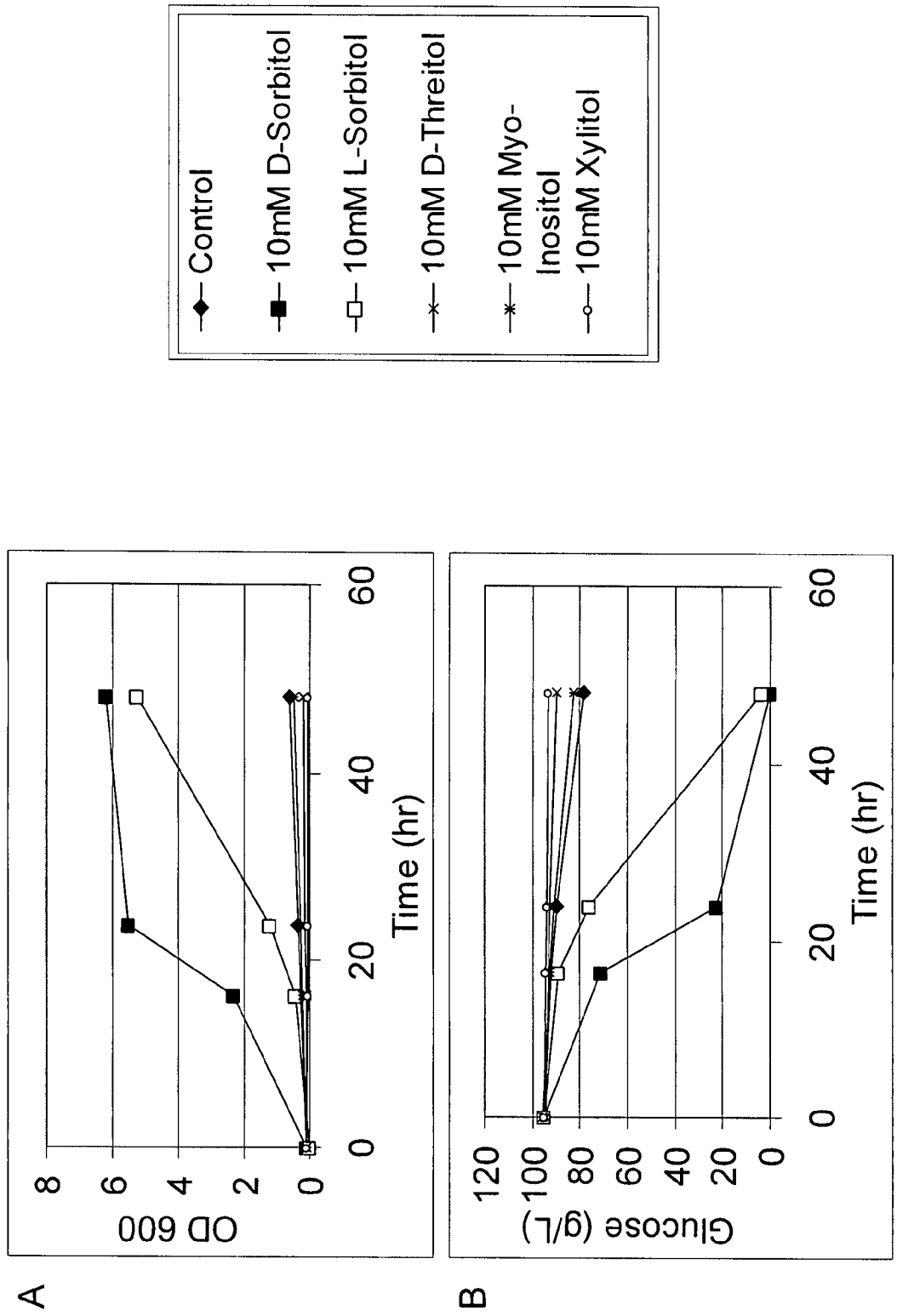

FIG. 22 shows graphs of growth (A) and glucose utilization (B) in the presence of different sugar alcohols.

Figure 23:
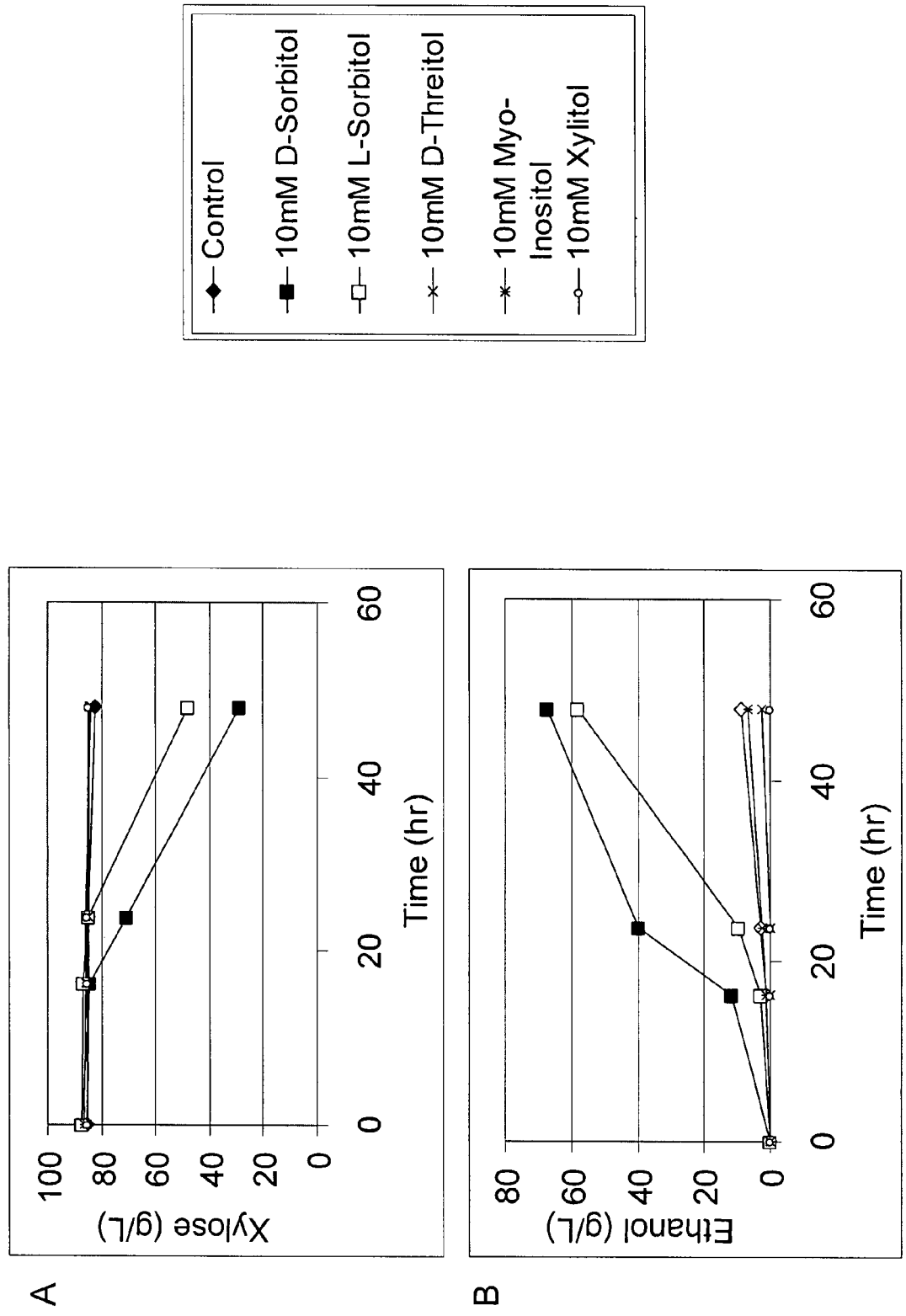

FIG. 23 shows graphs of xylose utilization (A) and ethanol production (B) in the presence of different sugar alcohols.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37C.F.R. §1.822.

A Sequence Listing is provided herewith on Compact Disk. The contents of the Compact Disk containing the Sequence Listing are hereby incorporated by reference in compliance with 37 CFR 1.52(e). The Compact Discs are submitted in duplicate and are identical to one another. The discs are labeled "Copy 1—Sequence Listing" and "Copy 2 Sequence listing" The discs contain the following file: CL3425 seq list.ST25.

SEQ IDs NO:1 and 2 are the nucleotide sequences of primers for amplification of a DNA fragment containing the glyceraldehyde-3-phosphate dehydrogenase gene promoter ($P_{gap}$) from pZB4.

SEQ IDs NO:3 and 4 are the nucleotide sequences of primers for amplification of a DNA fragment containing a tal coding region from pZB4.

SEQ IDs NO:5 and 6 are the nucleotide sequences of primers for amplification of a DNA fragment containing $P_{gap}$-tal from the $P_{gap}$ and tal fragments.

SEQ IDs NO:7 and 8 are the nucleotide sequences of primers for amplification of a DNA fragment containing loxP::Cm from pZB186.

SEQ ID NO:9 is the complete nucleotide sequence for the pMODP$_{gap}$taltktCm plasmid.

SEQ IDs NO:10 and 11 are the nucleotide sequences of primers for amplification of a 3 kb DNA fragment containing tal and tkt coding regions in transformants receiving pMOD-P$_{gap}$taltktCm.

SEQ ID NO:12 is the complete nucleotide sequence for the pMODP$_{gap}$xylABCm plasmid.

SEQ ID NOs:13 and 14 are the nucleotide sequences of primers for amplification of a 1.6 kb PgapxylA DNA fragment from the T2C, T3C, T4C and T5C integrants with pMODP$_{gap}$xylABCm.

SEQ ID NOs:15 and 16 are the nucleotide sequences of primers for amplification of a 1.3 kb xylB DNA fragment from the T2C, T3C, T4C and T5C integrants with pMODP$_{gap}$xylABCm.

Applicants made the following biological deposit under the terms of the Budapest Treaty on the International Recognition of the Deposit of Micro-organisms for the Purposes of Patent Procedure at the American Type Culture Collection (ATCC) 10801 University Boulevard, Manassas, Va. 20110-2209:

| Depositor Identification Reference | International Depository Designation | Date of Deposit |
|---|---|---|
| ZW658 | ATCC # PTA-7858 | Sept. 12, 2006 |

DETAILED DESCRIPTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a method for the production of ethanol using fermentation that involves the addition of sorbitol, mannitol, galactitol, or ribitol to a medium containing mixed sugars including xylose. The medium including sorbitol provides for growth of xylose-utilizing *Zymomonas mobilis* strains, thus increasing the ability of such strains to produce of ethanol from the mixed sugars.

In this disclosure, a number of terms are used. The following definitions are provided:

RM is rich medium.
RMG5% is RM+5% glucose.
RMG10% is RM+10% glucose.
RMX8% is RM+8% xylose.
RMX2% is RM+2% xylose.
RMX5% is RM+5% xylose.
RMGX10%8% is RM+10% glucose and 8% xylose.
RMGX5%8% is RM+5% glucose and 8% xylose.

The term "fermentable sugar" refers to oligosaccharides and monosaccharides that can be used as a carbon source by a microorganism in a fermentation process.

As used herein "suitable medium" refers to a medium that supports growth of *Z. mobilis* under various conditions. The suitable medium includes xylose and at least one additional sugar, and one or more sugar alcohol that may be sorbitol, mannitol, galactitol, ribitol or mixtures thereof. In addition, if a sufficient concentration of the sugar alcohol is not present in the medium, the medium is one that while supporting growth, does not provide for optimal xylose utilization.

The term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "saccharification" refers to the production of fermentable sugars from polysaccharides.

The term "pretreated biomass" means biomass that has been subjected to pretreatment prior to saccharification.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

"Biomass hydrolysate" refers to the product resulting from saccharification of biomass. The biomass may also be pretreated prior to saccharification.

"Gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "genetic construct" refers to a nucleic acid fragment that encodes for expression of one or more specific proteins. In the gene construct the gene may be native, chimeric, or foreign in nature. Typically a genetic construct will comprise a "coding sequence". A "coding sequence" refers to a DNA sequence that codes for a specific amino acid sequence.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of sense (mRNA) or antisense RNA derived from a gene. Expression may also refer to translation of mRNA into a polypeptide.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

Xylose-utilizing *Zymomonas* Strain

Any strain of *Z. mobilis* that has been engineered for xylose metabolism may be used in fermentations to produce ethanol according to the present method. Typically four genes are introduced into *Z mobilis* for expression of four enzymes involved in xylose metabolism as described in U.S. Pat. No. 5,514,583, which is herein incorporated by reference. These include genes encoding xylose isomerase, which catalyses the conversion of xylose to xylulose, and xylulokinase, which phosphorylates xylulose to form xylulose 5-phosphate. In addition, transketolase and transaldolase, two enzymes of the pentose phosphate pathway, convert xylulose 5-phosphate to intermediates that couple pentose metabolism to the glycolytic Entner-Douderoff pathway permitting the metabolism of xylose to ethanol. DNA fragments with sequences encoding these enzymes may be obtained from any of numerous microorganisms that are able to metabolize xylose, such as enteric bacteria, and some yeasts and fungi. The coding regions of these genes are operably linked to promoters that are expressed in *Z. mobilis* cells, such as the promoter of *Z. mobilis* glyceraldehyde-3-phosphate dehydrogenase or *Z. mobilis* enolase, and other regulatory elements. These chimeric genes are typically constructed in vectors that are transformed into *Z. mobilis* cells to engineer a xylose utilizing strain. Xylose utilizing *Z. mobilis* strains that are known and new strains of *Z. mobilis* that are engineered for xylose utilization may be used in the present method. Xylose utilizing *Z. mobilis* strains include *Z. mobilis* ZM4(pZB5) (Joachimsthal and Rogers, supra), *Z. mobilis* CP4:pZB5 (Lawford et al., supra), *Z. mobilis* 8b (US 20030162271), ZW658 (described herein; ATCC # PTA-7858), and ZW800, ZW801-4 and ZW801-6 (described in co-owned and co-pending U.S. patent application 60/847,813, which is herein incorporated by reference). Particularly useful are the strains *Z. mobilis* 8b, ZW658, ZW800, ZW801-4 and ZW801-6.

The xylose-utilizing *Z. mobilis* strain ZW658 was found to have distinct properties as compared to the *Z. mobilis* 8b strain, as shown in Example 2 herein. Under the same fermentation conditions ZW658 shows reduced xylitol production, increased xylose utilization, and increased ethanol production as compared to 8b. These properties are evident following the adaptation process, which did not include mutagenesis as in the case of the 8b strain adaptation.

The xylose-utilizing *Z. mobilis* strain ZW800 has an additional genetic modification that inactivates the gene encoding glucose-fructose oxidoreductase (GFOR) and results in reduced xylitol synthesis, Specifically, ZW800 has an insertion of a selection marker into the GFOR coding region that disrupts expression of the encoded protein, as described in detail in co-owned and co-pending U.S. patent application 60/847,813, which is herein incorporated by reference. The GFOR knockout mutant produced reduced amounts of xylitol when grown on xylose-containing sugar mixtures, consumed more xylose, and produced higher concentrations and yields of ethanol when grown in high sugar mixtures in the presence of sorbitol than the parent strain that expressed GFOR. Described also in U.S. patent application 60/847,813 are strains ZW801-4 and ZW801-6 which were derived from ZW800 and have had the selection marker removed by Cre/lox mediated excision, resulting in a deletion and lox site footprint addition within the GFOR coding region that disrupts the GFOR coding region. Strains ZW801-4 and ZW801-6 have the same properties described above for ZW800.

*Z. mobilis* strains that are additionally engineered to utilize sugars other than xylose, which it does not naturally use, may be used in the present method. An example is a strain of *Z. mobilis* engineered for arabinose utilization as described in U.S. Pat. No. 5,843,760, which is herein incorporated by reference.

Mixed Sugars

In the present method, cells of xylose-utilizing *Z. mobilis* strains are grown in medium containing mixed sugars. The mixed sugars referred to herein include xylose, which the *Z. mobilis* cells have been engineered to utilize, and at least one additional sugar. Any sugar that may provide an energy source for metabolism of the *Z. mobilis* cells, or any sugar that is present in a mixture containing xylose may be included. It is desirable to grow xylose-utilizing *Z. mobilis* cells on sugars that are produced from biomass saccharification. Typically biomass is pretreated, for example as described in Patent Application WO2004/081185 and in co-owned and co-pending U.S. application 60/670,437, and then treated with saccharification enzymes as reviewed in Lynd, L. R., et al. (Microbiol. Mol. Biol. Rev. (2002) 66:506-577). Biomass saccharification produces sugars that may typically include a mixture of xylose with glucose, fructose, sucrose, galactose, mannose, and/or arabinose.

The mixed sugars may be used in a high concentration in medium for growth of the *Z mobilis* cells. This allows the direct use of biomass saccharification sugars, or use with little dilution, thereby reducing fermentation volumes, which is desirable for commercial scale ethanol production. High sugars concentrations are used so that greater concentrations of ethanol may be produced. The mixed sugar concentration is typically at least about 120 g/L and up to about 300 g/L. In this range of mixed sugars concentration, a sugar alcohol may be added to the growth medium to provide the beneficial effect that is described below. Particularly useful is a mixed sugar concentration that is between about 150 g/L and about 235 g/L.

The ratio of different sugars may vary in the mixture, with xylose typically at least about 10% of the total amount of sugars. Preferably xylose is between about 40% and about 60%. Fructose is present in sugars produced by saccharification of some biomass such as sugar cane bagasse, and may replace a portion of xylose or glucose, such that xylose remains at least about 10% of the sugar mixture. In addition, arabinose is derived from hemicellulose and thus is a typical component of mixed sugars derived from saccharified biomass containing hemicellulose.

Improved Ethanol Production

In the present method, the production of ethanol by xylose-utilizing *Z. mobilis* is improved by including a sugar alcohol from the family of 6-carbon sugars, selected from sorbitol (including D-sorbitol or L-sorbitol), mannitol, galactitol, and a mixture thereof, in a medium containing mixed sugars including xylose. In addition to these effective sugar alcohols, the 5-carbon sugar alcohol ribitol (also called adonitol) is also effective and may be used. While addition of sorbitol to medium containing only xylose as the sugar had no effect on ethanol production, as demonstrated in Example 3 herein, it was surprisingly found that sorbitol had a beneficial effect on ethanol production by xylose-utilizing *Z. mobilis* when xylose was included in a mixed sugar composition in the medium. Applicants found that in the presence of sorbitol, ethanol production was increased significantly in the mixed sugar medium that included xylose. In one embodiment, the mixed sugar comprises xylose and one or more other sugars. In one embodiment the one or more other mixed sugar is glucose.

In general, production of ethanol varies depending on fermentation conditions used, including the composition of the medium. A medium composition that supports growth may not provide for optimal xylose utilization in xylose-utilizing *Z. mobilis* due to the presence of high sugars concentration, inhibitors, or other factors. Addition of sorbitol, or any of the other sugar alcohols listed above, to such a medium renders it a suitable medium in the present method. For example, media may include inhibitors such as acetate, as is present in saccharified biomass, which affect ethanol production levels. Addition of sorbitol to mixed sugar medium containing acetate was shown herein to improve ethanol production by xylose-utilizing *Z. mobilis*. In the presence of sorbitol, or other designated sugar alcohol, ethanol production may be increased by at least about 5%, though the exact amount varies depending upon the composition of the suitable medium in use. Comparisons are made at stationary phase of the fermentation culture, when maximal ethanol production is reached.

The increase in ethanol production in the presence of sorbitol or other designated sugar alcohol, may occur when xylose-utilizing *Z. mobilis* is grown in media containing mixed sugars at concentrations where no growth lag occurs. The concentration of mixed sugars in media that support growth with no lag varies depending on other components in the medium, such as inhibitors. For example, an obvious lag period typically does not occur when xylose-utilizing *Z. mobilis* is grown in media without acetate containing mixed sugars at concentrations below about 165 g/L. With no lag in growth occurring, the *Z. mobilis* cells are not characterized as undergoing osmotic stress, since the typical feature of osmotic stress is the growth lag. Thus, it is surprising that sorbitol or other sugar alcohol described herein increases ethanol production under the no-lag condition with mixed sugars, which is distinguished from the osmotic effect of sorbitol on wild type *Z. mobilis* growth observed by Loos et al, (supra) in high concentrations of glucose. At higher concentrations of mixed sugars, where typically a growth lag does occur, the same effect of sorbitol or other sugar alcohol described herein on ethanol production, characterized for no-lag conditions, continues to occur.

In the present method where sorbitol or other sugar alcohol described herein is included in the medium with mixed sugars, forming a suitable medium, xylose-utilizing *Z. mobilis* also showed increased utilization of xylose. As with ethanol production described above, in general xylose utilization varies depending on fermentation conditions, including the composition of the medium. For example, media may include inhibitors such as acetate, as is present in saccharified biomass, which can affect xylose utilization. Addition of sorbitol to the mixed sugar medium containing acetate improved xylose utilization by xylose-utilizing *Z. mobilis*. In the presence of sorbitol or other sugar alcohol described herein, xylose utilization may be increased by at least about 5% over the level of xylose utilized under the same conditions without sorbitol or other sugar alcohol described herein though the exact amount varies depending upon the composition of the suitable medium in use. For example, in Examples 4 and 5 herein, in the absence of acetate in the medium, 85 g/L of xylose, in a sugars mixture with 100 g/L glucose, was completely utilized within about 30 hours in the presence of sorbitol, while without sorbitol in the medium, about 20% of the xylose remained when the culture reached stationary phase at about 60 hours. Comparisons are made at stationary phase of the fermentation culture, when maximal xylose utilization is reached.

In addition, in accordance with the discovery herein, when xylose-utilizing *Z. mobilis* is grown on medium containing mixed sugars under conditions where xylitol is produced with no sorbitol present, the amount of xylitol produced is decreased when sorbitol is included in the medium. Reduction in xylitol production is at least about 6% in the presence of sorbitol, though the exact amount varies depending upon the composition of the suitable medium in use. For example, in Examples 4 and 5 herein, xylitol was reduced with addition of sorbitol by about 3-fold.

Without wishing to be bound by theory, it is thought that reduced xylitol production allows increased xylose utilization. The increased xylose utilization, along with the reduction in carbon flow to the by-product xylitol, together allow increased ethanol production. Therefore, the reduced xylitol production, increased xylose utilization, and increased ethanol production are all manifestations of improved performance of xylose-utilizing *Z. mobilis* grown on the suitable medium described herein as containing mixed sugars, including xylose, and sorbitol or other sugar alcohol as described above.

Sugar alcohols such as erythritol, maltitol, and lactitol, as well as the frequently used osmoprotectant glutamate, do not increase ethanol production nor do they increase xylose utilization by xylose-utilizing *Z. mobilis* grown on suitable medium containing mixed sugars. Glutamate does act as a typical osmoprotectant, eliminating the lag period for initial growth when the xylose-utilizing *Z. mobilis* is grown under conditions where a lag occurs. However, in the presence of glutamate, xylitol production is not reduced, xylose utilization is not enhanced, and ethanol production is not improved. Thus, a compound that does act as an osmoprotectant does not improve performance as do sorbitol and mannitol, galactitol, or ribitol. This finding indicates that these sugar alcohols are performance enhancers for xylose-utilizing *Z. mobilis*.

Sorbitol, mannitol, galactitol, ribitol or mixtures thereof may be added in an amount that is between about 0.5 mM and about 200 mM. In addition, these sugar alcohols may be used together in any ratio in a total amount that is between about 0.5 mM and about 200 mM. Particularly useful is an amount that is between about 2 mM and about 100 mM, with 5 mM to 20 mM preferred.

For production of ethanol, recombinant xylose-utilizing *Z. mobilis* is brought in contact with a suitable medium that contains a mixed sugar including xylose, and either sorbitol, other designated sugar alcohol, or a mixture thereof. The xylose-utilizing *Z. mobilis* is typically inoculated into the suitable medium. An inoculation ratio that is between about 0.01% and about 20% (v/v) is desirable for initiating a fermentation culture. Typically, an inoculation ratio that is between about 0.1% and about 20% (v/v) is used, while more typically the ratio is between about 1% and about 20% (v/v). The *Z. mobilis* grows in the medium where fermentation occurs and ethanol is produced. The fermentation is run without supplying air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. Typically, if inhibitors are present in the medium, a longer fermentation period is required. The contacting, and continuing fermentation, are typically at temperatures that are between about 25° C. and about 40° C., at a pH of about 4.5 to about 7.5. More suitable is contacting, and continuing fermentation, at temperatures between about 30° C. and about 37° C. More suitable is contacting, and continuing fermentation, at pH of about 5.0 and 6.0.

Fermentation for Ethanol Production

In the present method xylose-utilizing *Z. mobilis* may be grown in a suitable medium containing mixed sugars including xylose in laboratory scale fermenters, and in scaled-up fermentation where commercial quantities of ethanol are produced. Where commercial production of ethanol is desired, a variety of culture methodologies may be applied. For example, large-scale production from xylose-utilizing *Z. mobilis* may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: *A Textbook of Industrial Microbiology*, Crueger, Crueger, and Brock, Second Edition (1989) Sinauer Associates, Inc., Sunderland, MA, or Deshpande, Mukund V., *Appl. Biochem. Biotechnol.* 36, 227, (1992), herein incorporated by reference.

Commercial production of ethanol may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for ethanol production is a fermentation regime as follows. The desired xylose-utilizing *Z. mobilis* strain is grown in shake flasks in semi-complex medium at about 30° C. to about 37° C. with shaking at about 150 rpm in orbital shakers and then transferred to a 1-10 L seed fermentor containing similar medium. The seed culture is grown in the seed fermentor anaerobically until $OD_{600}$ is between 3 and 6, when it is transferred to the production fermentor where the fermentation parameters are optimized for ethanol production. Typical inoculum volumes transferred from the seed tank to the production tank range from about 2% to about 20% v/v. Typical fermentation medium contains minimal medium components such as potassium phosphate (1.0-10.0 g/l), ammonium sulfate (0-2.0 g/l), magnesium sulfate (0-5.0 g/l), a complex nitrogen source such as yeast extract or soy based products (0-10 g/l). A final concentration of about 5-20 mM sorbitol or designated sugar alcohol is present in the medium. Mixed sugars including xylose and at least one additional sugar such as glucose (or sucrose), providing a carbon source, are continually added to the fermentation vessel on depletion of the initial batched carbon source (50-200 g/l) to maximize ethanol rate and titer. Carbon source feed rates are adjusted dynamically to ensure that the culture is not accumulating glucose in excess, which could lead to build up of toxic byproducts such as acetic acid. In order to maximize yield of ethanol produced from substrate utilized, biomass growth is restricted by the amount of phosphate that is either batched initially or that is fed during the course of the fermentation. The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-37° C. In order to minimize foaming, antifoam agents (any class-silicone based, organic based etc) are added to the vessel as needed. An antibiotic, for which there is an antibiotic resistant marker in the strain, such as kanamycin, may be used optionally to minimize contamination.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used here are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" means milliliter(s), "μL" means microliter(s), "μg" means microgram(s), "ng" means nanogram(s), "mM" means millimolar, "μM" means micromolar, "nm" means nanometer(s), "μmol" means micromole(s), "pmol" means picomole(s), "Cm" means chloramphenicol, "Cm$^r$" means chloramphenicol resistant, "Cm$^s$" means chloramphenicol sensitive, "Sp$^r$" means spectinomycin resistance, "Sp$^s$" means spectinomycin sensitive, "XI" is xylose isomerase, "XK" is xylulokinase, "TAL" is transaldolase, "TKT" is transketolase, "EFT" means elapsed fermentation time, "RM" means rich medium containing 10 g/L yeast extract plus 2 g/L KH2PO4, "MM" means mating medium containing 10 g/L yeast extract, 5 g/L tryptone, 2.5 g/L (NH$_4$)$_2$SO$_4$ and 0.2 g/L KH$_2$PO4.

Measurement of Optical Density (OD)

Approximately 1 ml of well mixed sample was obtained from flask or fermentor. First the sample absorbance was measured directly with a spectrophotometer (Amersham Biosciences Ultrospec 3300pro, GE Healthcare, Piscataway, N.J., USA). If the reading was lower than 0.6 unit, no dilution was needed. If the reading was higher than 0.6 unit, the sample was diluted with culture medium until the actual reading was in the range of 0.1 to 0.6 unit. The original OD was calculated from the dilution ratio and the actual reading.

Enzyme Assays

Preparation of Cell-Free Extracts of *Zymomonas* for Enzymatic Assays

Cells were grown in 50 ml of RM+2% glucose at 30° C. overnight to an OD$_{600}$ of 1.0-1.2. Cells were harvested by centrifugation at 4500 rpm for 10 min at 4° C. The supernatant was discarded and the cell pellet washed with 25 ml ice-cold sonication buffer. (10 mM Tris, pH 7.6, 10 mM MgCl$_2$), followed by centrifugation at 4500 rpm for 10 min. The pellet was resuspended in 2.0-2.5 ml sonication buffer plus 1 mM dithiothreitol. A 500 μl aliquot was centrifuged for 1 min in an eppendorf centrifuge at 4° C. Most of supernatant was discarded, leaving ~10-20 μl behind to keep the pellet from drying out. The cells were frozen and stored at –80° C. until assayed. Prior to assay, the cells were thawed and resuspended with 500 μl of sonication buffer+1 mM DTT. The mix was sonicated 2× for 45 seconds at 62% duty cycle and an output control of 2 using a Branson sonifier 450, letting samples cool ~3-5 min between sonications. Samples were centrifuged at 14,000 rpm for 60 min in a Beckman microfuge at 4° C. The supernatant was transferred to a new tube and kept at 4° C. The Pierce BCA assay was used for determining protein concentrations.

Figure 1:
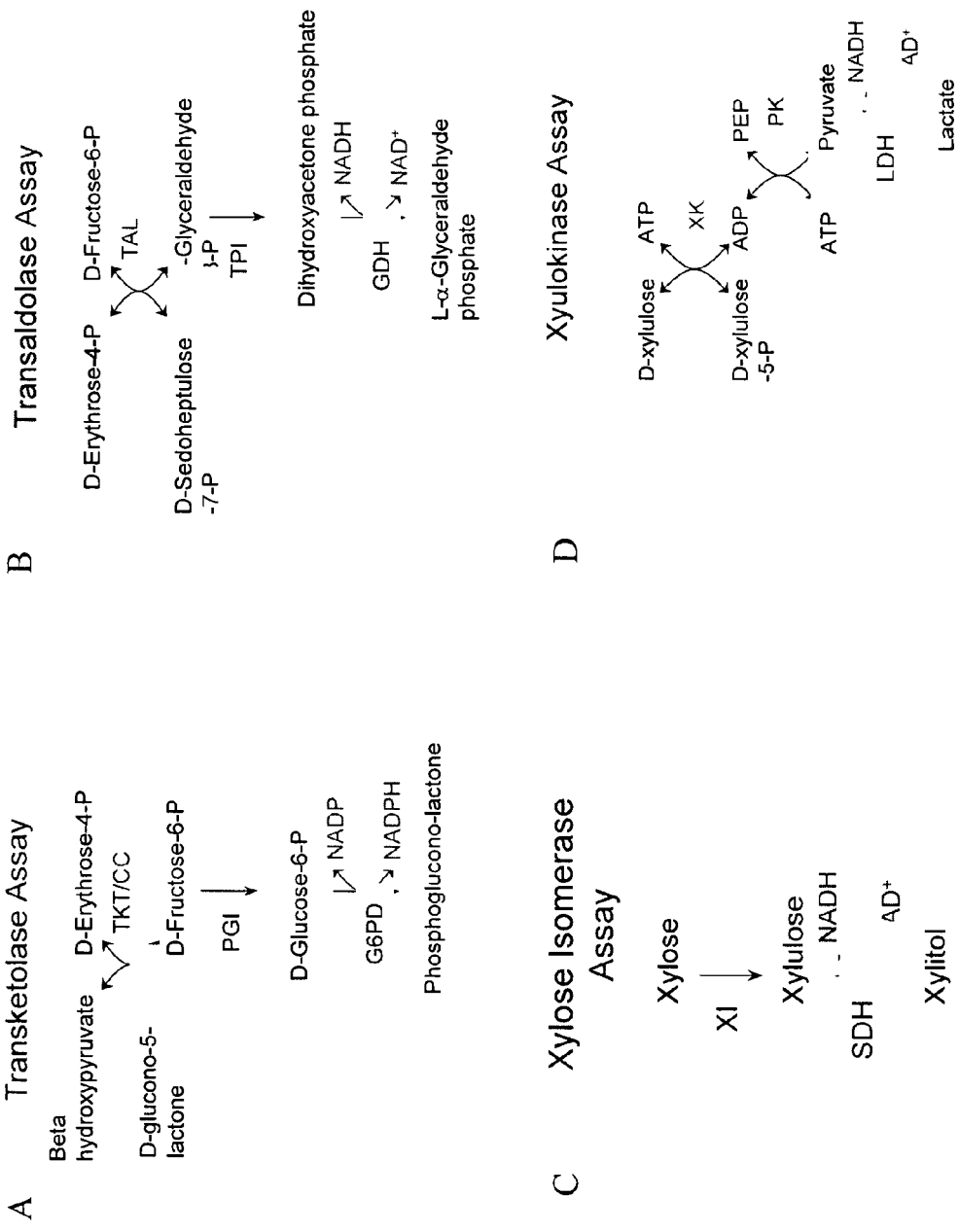
FIG. 1 shows the strategies for enzyme assays of transketolase (A), transaldolase (B), xylose isomerase (C), and xyulokinase (D).

The transketolase (TKT) assay was usually performed first since this enzyme is more labile than the others. A diagram of the TKT assay is shown in FIG. 1A. In a microplate assay, 20 μl of cell free extract was added to each well in a reaction mix, at 30° C., that included the following final concentrations of components: 0.37 mM NADP, 50 mM Tris HCl pH 7.5, 8.4 mM Mg Cl$_2$, 0.1 mM TPP ((thiamine pyrophosphate chloride), 0.6 mM E4P (erythrose-4-phosphate), 4 mM BHP (betahydroxypyruvate), 4 U/ml PGI (phosphoglucose isomerase), and 4 U/ml G6PD (glucose-6-phosphate dehydrogenase). The A$_{340}$ was read on a plate reader for 3-5 min. TKT activity was calculated as follows:

1 unit corresponds to the formation of 1 μmol of D-fructose 6-phosphate/min at 30° C.

$U$ (μmole/min)=slope (dA$_{340}$/min)*volume of reaction (μL)/6220/0.55 cm (moles of NADP→NADPH is 6220 A$_{340}$ per mole per L in a 1 cm cuvette)

(pathlength of 200 μl per well in microplate=0.55 cm)

Specific Activity (μmole/min-mg)=μmole/min/protein concentration (mg)

The basis of the transaldolase (TAL) assay is shown in FIG. 1B. In a microplate assay, 20 μl of cell free extract was added to each well in a reaction mix, at 30° C., that included the following final concentrations of components: 0.38 mM NADH, 87 mM thiethanolamine, 17 mM EDTA, 33 mM F6P (fructose-6-phosphate), 1.2 mM E4P (erythrose-4-phosphate), 2.0 U/ml GDH (Glycerol-3-phosphate dehydrogenase), and 20 U/ml TPI (Triose phosphate isomerase). The plate was incubated for 5 min., then the A$_{340}$ was read for 3-5 min. TAL activity was calculated as follows:

1 unit corresponds to the formation of 1 µmol of D-glyceraldehyde per minute at 30° C.

$U$ (µmole/min)=slope (dA$_{340}$/min)*volume of reaction (µL)/6220/0.55 cm (moles of NADH→NAD is 6220 A$_{340}$ per mole per L in a 1 cm cuvette)
(pathlength of 200 µl per well in microplate=0.55 cm)
Specific Activity (µmole/min-mg)=µmole/min/protein The basis of the xylose isomerase (XI) assay is shown in FIG. 1C.

In a microplate assay, 20 µl of cell free extract was added to each well in a reaction mix, at 30° C., that included the following final concentrations of components: 0.256 mM NADH, 50 mM xylose, 10 mM MgSO$_4$, 10 mM thiethanolamine, and 1 U/ml SDH (sorbitol dehydrogenase). The A$_{340}$ was read on a plate reader for 3-5 min. XI activity was calculated as follows:

1 unit of XI corresponds to the formation of 1 µmole of D-xylulose per minute at 30° C.

$U$ (µmole/min)=slope (dA$_{340}$/min)*volume of reaction (µL)/6220/0.55 cm (moles of NADHP→NAD is 6220 A$_{340}$ per mole per L in a 1 cm cuvette)
(pathlength of 200 µl per well in microplate=0.55 cm)
Specific Activity (µmole/min-mg)=µmole/min/protein concentration (mg)

The basis of the xylulokinase (XK) assay is shown in FIG. 1D. In a microplate assay, 20 µl of cell free extract was added to each well in a reaction mix, at 30° C., that included the following final concentrations of components: 0.2 mM NADH, 50 mM Tris HCl pH 7.5, 2.0 mm MgCl$_2$-6H$_2$O, 2.0 M ATP 0.2 M PEP (phosphoenolpyruvate), 8.5 mM D-xylulose, 5 U/ml PK (pyruvate kinase), and 5 U/ml LDH (lactate dehydrognase). The A$_{340}$ was read on a plate reader for 3-5 min. XI activity was calculated as follows:

1 unit corresponds to the formation of 1 µmol of D-xylulose-5-phosphate per minute at 30° C.

$U$ (µmole/min)=slope (dA$_{340}$/min)*volume of reaction (µL)/6220/0.55 cm (moles of NADH→NAD is 6220 A$_{340}$ per mole per L in a 1 cm cuvette)
(pathlength of 200 µl per well in microplate=0.55 cm)

Specific Activity (µmole/min-mg)=µmole/min/protein concentration (mg)

HPLC Method

The analysis of sugars, acetate, ethanol, and other by-products was done with an Agilent 1100 series HPLC and Agilent ChemStation software for LC 3D. The column was BioRad Aminex HPX-87H(HPLC Organic Analysis Column 125-0140) with BioRad Micro-Guard Cartridge Cation-H (125-0129). The operating conditions were:

| | |
|---|---|
| Flow | 0.6 ml/min |
| Solvent | 0.01N H$_2$SO$_4$ |
| Stop Time | 25 min |
| Injection Volume | 5 µl |
| Auto Sampler | Temp Control @ 10° C. or 4° C. |
| Column Temp | 55° C. |
| Detector | Refractive Index (40° C.) with External Standard Calibration Curves |

Seed Cultivation

Glycerol stock of seed frozen at −80° C. was thawed, then inoculated into sterile culture tubes with mixture of 60 g/L glucose, 20 g/L xylose, 10 g/L yeast extract (YE), 10 g/L KH$_2$PO$_4$, 2 g/L (NH$_4$)$_2$SO$_4$, and 1 g/L MgSO$_4$. Initial pH was adjusted to 5.5 with 4 N KOH. This revival culture was grown statically overnight at 37° C. It was transferred into shake flasks with 75 g/L glucose, 25 g/L xylose, 10 g/L yeast extract (YE), 10 g/L KH$_2$PO$_4$, 2 g/L (NH$_4$)$_2$SO$_4$, and 1 g/L MgSO$_4$. Initial pH was adjusted to 5.5 with 4 N KOH. Growth was monitored by measuring OD$_{600}$. When the OD reached approximately 5, a certain volume of the seed was withdrawn into a sterile syringe for inoculation.

Example 1

Construction of ZW658, a Xylose-fermenting *Zymomonas mobilis* Strain

ZW658 was constructed by integrating two operons, P$_{gap}$xylAB and P$_{gap}$taltkt, containing four xylose-utilizing genes encoding xylose isomerase, xylulokinase, transaldolase and transketolase, into the genome of ZW1 (ATCC #31821) via sequential transposition events, and followed by adaptation on selective media containing xylose. Previously, a xylose-fermenting *Zymomonas mobilis* strain called 8b was constructed, as described in United States Patent Application 20030162271, by integrating the two operons P$_{gap}$xylAxylB and P$_{eno}$taltkt, along with selectable antibiotic markers, into the genome of *Zymomonas mobilis* 5C via a combination of homologous recombination and transposon approaches followed by adaptation and NTG mutagenesis. In the preparation of ZW658, transposition (Epicentre's EZ::Tn in vitro transposition system) was used, as opposed to site specific homologous recombination, because this approach offers the advantages of multiple choices of integration sites and relatively high insertion frequency. The four genes encoding the xylose utilization enzymes were arranged and cloned as two separate operons: P$_{gap}$xylAB and P$_{gap}$taltkt for the integration. An antibiotic resistance marker, a chloramphenicol resistance (Cm$^r$) gene flanked by two P1 phage Cre-recombinase recognition sequences (loxP), was attached to each operon for the selection of integrants. The integration of the two operons was accomplished in a two-step, sequential manner: P$_{gap}$taltkt followed by P$_{gap}$xylAB. Cm resistance selection was used in both integration events, since it was removed by expressing a Cre recombinase on a plasmid followed by curing of the plasmid after each integration. This process allowed the use of the same antibiotic marker for selection multiple times. More importantly, it allowed the removal of the antibiotic marker introduced for selection of the integration of the operons. This process eliminated the negative impact of antibiotic resistance gene(s) on the fermentation strain for commercial use.

Construction of pMODP$_{gap}$taltktCm for Transposition

Figure 2:
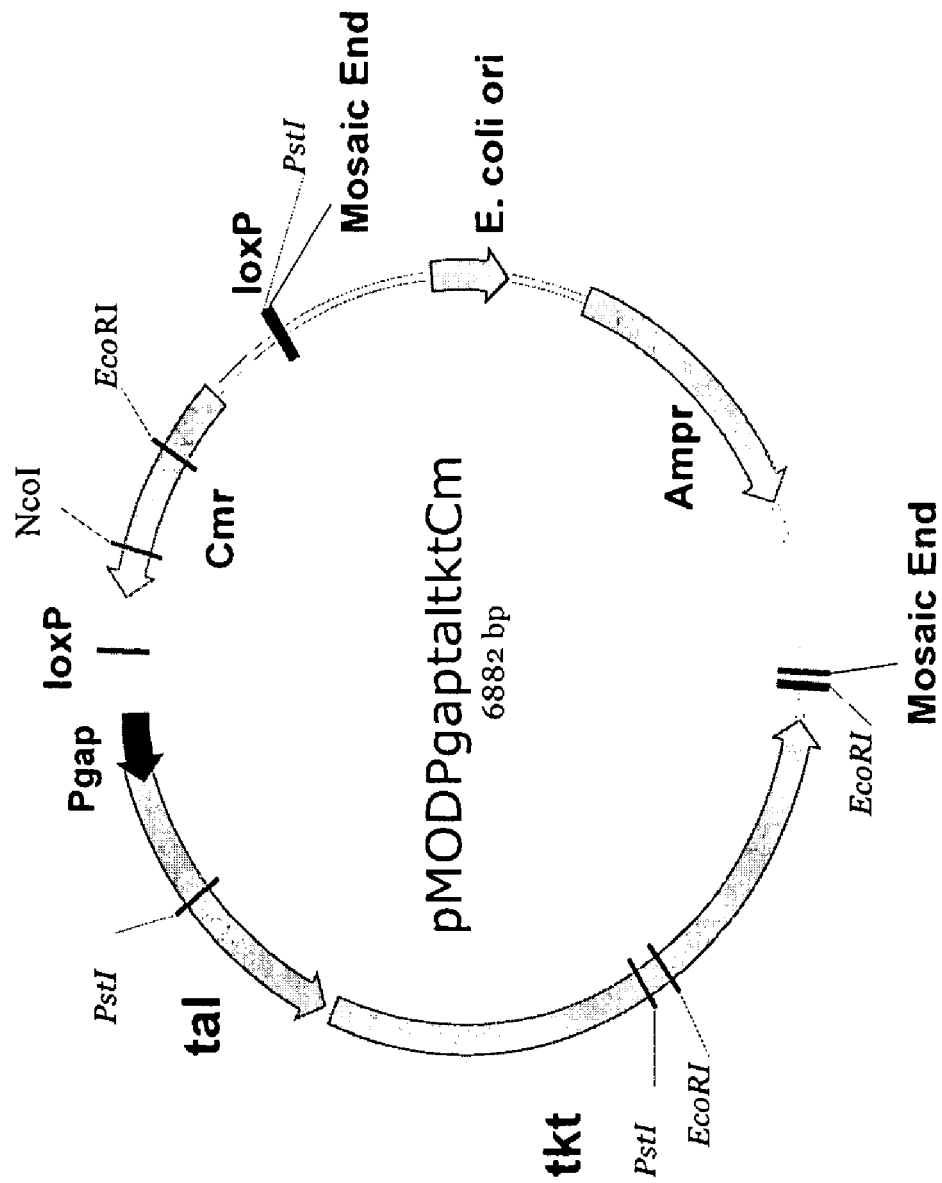
FIG. 2 shows a plasmid map of pMODPgaptaltktCm.

As described in the US Patent Application 20030162271 (Example 9 therein), a 2.2 kb DNA fragment containing the transketolase (tkt) coding region from *E. coli* was isolated from pUCtaltkt (US Patent Application 20030162271) by BglII/XbaI digestion and cloned in a PMOD (Epicentre Biotechnologies, Madison, Wis.) vector digested with BamHI/XbaI, resulting in pMODtkt. A PCR fragment named P$_{gap}$tal was generated by fusing the promoter region of the *Zymomonas mobilis* gap (P$_{gap}$; glyceraldehyde-3-phosphate dehydrogenase) gene to the coding region of *E. coli* transaldolase (tal) as follows. A P$_{gap}$ fragment was amplified from pZB4, the construction of which is described in U.S. Pat. No. 5,514,583 (Example 3), using primers with SEQ ID NOs:1 and 2. pZB4 contains a $P_{gap}$-xylA/xylB operon and a $P_{ENO}$-tal/tkt operon. A tal coding region fragment was amplified from pZB4 using primers with SEQ ID NOs: 3 and 4. A $P_{gap}$tal fragment was amplified using the $P_{gap}$ and tal fragments as template using primers with SEQ ID NOs:5 and 6. This fragment was digested with XbaI and cloned into the plasmid pMODtkt, upstream of the tkt coding region. A loxP::Cm fragment was generated by PCR using Cmlox(F,sfi) and Cmlox(R,sfi) primers (SEQ ID NOs:7 and 8) and pZB186 as the template. pZB186 is a combination of a native Z. mobilis plasmid and pACYC184, described in U.S. Pat. No. 514,583 (Example 3) and Zhang et al. ((1995) Science 267:240-243). Finally, the loxP::Cm PCR fragment was inserted in the SfiI site of the plasmid containing $P_{gap}$taltkt to form the integrative plasmid pMODP$_{gap}$taltktCm (FIG. 2). In this plasmid, the $P_{gap}$taltkt loxP::Cm fragment was inserted between two mosaic ends (transposase binding sites) in the pMOD vector. The complete nucleotide sequence for the pMODPgaptaltktCm plasmid is given as SEQ ID NO:9.

Transposition and Transformation of pMODP$_{gap}$taltktCm in ZW1

Plasmid pMOD is a pUC-based vector, and therefore is a non-replicative vector in Zymomonas. Plasmid pMODPgaptaltktCm was treated with transposase in the presence of $Mg^{2+}$ at room temperature for one hour and used to transform ZW1 cells by electroporation (using a BioRad Gene Pulser set at 200 ohms, 25 µF and 16 kV/cm). Electroporated cells were incubated in a mating medium (MM), which consists of 10 g/L yeast extract, 5 g/L tryptone, 2.5 g/L $(NH_4)_2SO_4$, 0.2 g/L $KH_2PO_4$) supplemented with 50 g/L glucose and 1 mM $MgSO_4$ for 6 hours at 30° C. The transformation mixture was plated on agar plates containing 15 g/L Bacto agar in MM supplemented with 50 g/L glucose and 120 µg/mL chloramphenicol and incubated anaerobically at 30° C. The transformants were visible after about 2 days. The transformation/transposition frequency was approx. $3\times10^1$/µg DNA.

A total of 39 $Cm^r$ transformant colonies was obtained. Twenty-one colonies were picked and further analyzed by PCR and enzymatic activity assays. PCR using primers SEQ ID NOs:10 and 11 confirmed the presence of a 3 kb DNA fragment containing tal and tkt coding regions in the transformants. Back transformation with plasmid DNA from the 21 integrant colonies generated no back transformants in E. coli suggesting the tal and tkt were integrated in the genome of ZW1. These integrants were tested for transaldolase and transketolase activities using protocols modified for microplates (General Methods). The Pierce BCA protein assay was used for the determination of protein concentrations. The transformants were grown up in RM containing 2% (w/v) glucose supplemented with 120 µg/ml chloramphenicol in 50 ml conical centrifuge tubes at 30° C. The control strains 8b and ZW1 were grown up as well (RM+2% glucose was used for ZW1) for enzymatic assays. Cells were harvested when the $OD_{600}$ reached 1.0. Cells were washed once and resuspended in sonication buffer (10 mM Tris-HCl, pH 7.6 and 10 mM $MgCl_2$). Enzymatic assays were conducted as described in US Patent Application, 20030162271. Units are given as µmole/min-mg. All samples had transaldolase and transketolase activities except for one.

Southern hybridization was performed on genomic and plasmid DNA of selected integrants digested with PstI using a tkt probe. ZW1 DNA did not hybridize with the tkt probe. A common 1.5 kb band was visible in all integrant genomic DNA samples, which is the expected DNA fragment between a PstI site in tkt and a PstI site in tal. A second visible high molecular weight (6 kb or greater) band was unique between independent lines T2, T3, T4 and T5 indicating a separate genomic integration site in each line. Interestingly, both plasmid and genomic DNA of T5 hybridized with the tkt probe indicating it was likely that $P_{gap}$taltkt was also integrated in T5 on the native plasmid. These four strains (T2, T3, T4 and T5) were selected for further Cre treatment to remove the $Cm^r$ marker.

Cre Treatment to Remove $Cm^r$ Marker from taltkt Integrants

To remove the $Cm^r$ marker, T2, T3, T4 and T5 were transformed with a derivative of the Zymomonas-E. coli shuttle vector pZB188 [Zhang et al. (1995) Science 267:240-243; U.S. Pat. No. 5,514,583] carrying a Cre expression cassette with a spectinomycin resistance marker (pZB188aadACreF). The transformants were selected on MM agar plates supplemented with 2% glucose and 200 µg/ml spectinomycin). $Sp^r$ resistant colonies were picked onto RM agar plates supplemented with 2% glucose and 200 µg/ml spectinomycin and RM agar plates supplemented with 2% glucose and 120 µg/mL Cm. One hundred percent of the colonies picked were $Cm^s$ indicating the high efficiency excision of $Cm^r$ by Cre. $Sp^rCm^s$ transformants were cultured in RM+2% glucose at 37° C. for 2 to 5 daily transfers to cure pZB188aadACreF. At each transfer, cells were diluted and plated on RM+2% glucose agar plates for picking onto additional plates of the same medium with or without 200 µg/mL Sp. $Sp^s$ colonies were analyzed by PCR to confirm the loss of pZB188aadACreF. The plasmid-cured descendents of the integrants were named T2C, T3C, T4C and T5C. To examine whether these transposition integrants were stable, these 4 strains were grown in RM+2% glucose and then transferred to 10 ml of the same medium and grown at 37° C. in duplicate test tubes. Cells were transferred daily for ten days, or approximately 100 generations. Colonies were diluted and plated onto RMG plates for colony isolation after the 1st and 10th transfers. Twelve colonies from each transfer of each strain tested positive for the presence of $P_{gap}$taltkt by colony PCR using 5'$P_{gap}$ and 3' tkt primers (SEQ ID NOs 1 and 11). Transaldolase and transketolase activities were also measured for isolates after the 1st and 10th transfers (as described in General Methods). All 4 integrants had similar levels of both TAL and TKT activities after 100 generations on the non-selective medium, suggesting these integrants were genetically stable.

Construction of pMODP$_{gap}$xylABCm for Transposition

Figure 3:
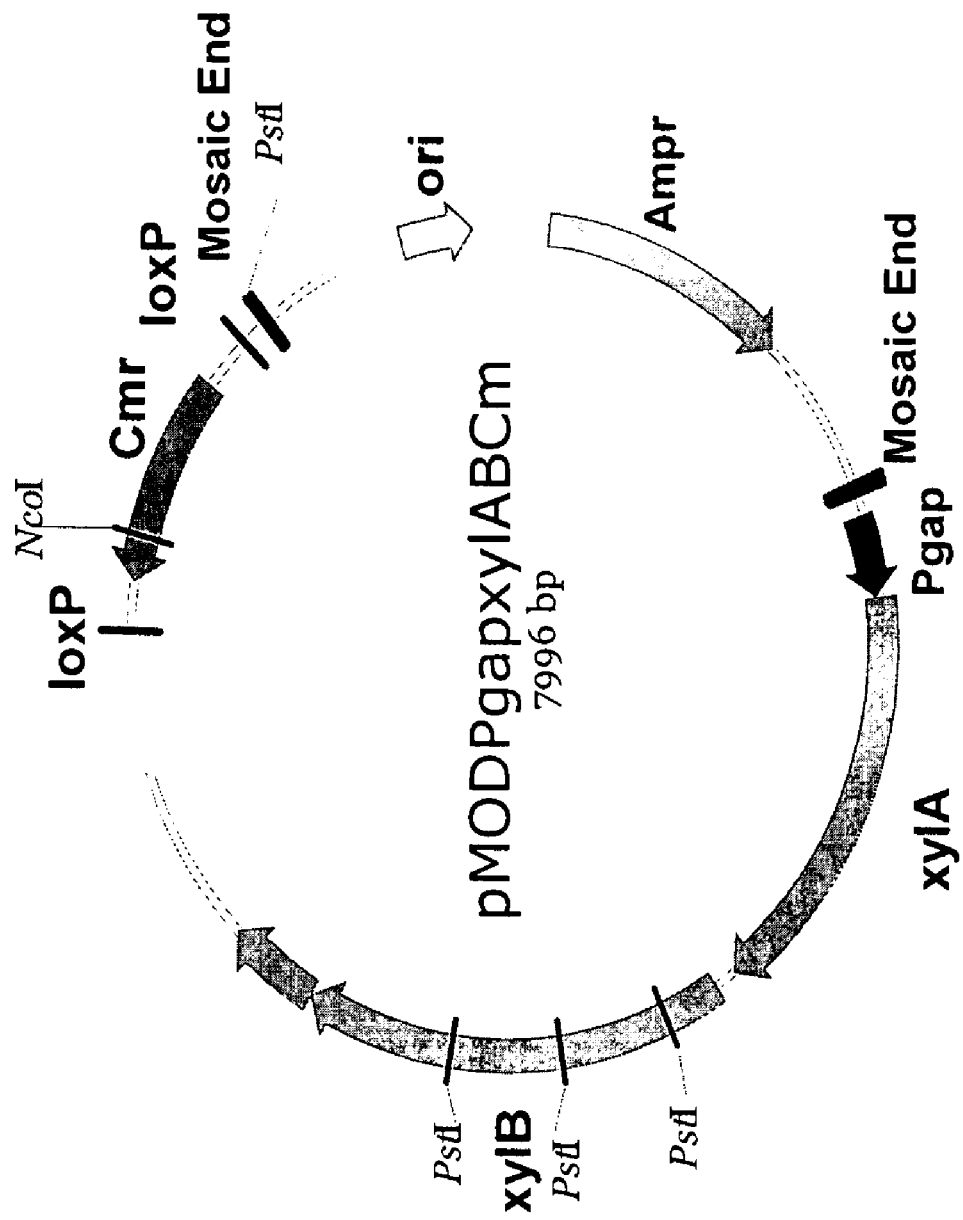
FIG. 3 shows a plasmid map of pMODPgapxylABCm.

The next step was to further integrate the P$_{gap}$xylAB loxP::Cm operon into the ZW1::P$_{gap}$taltkt integrants (T2C, T3C, T4C and T5C). The integrative plasmid pMODP$_{gap}$xylABCm (FIG. 3) was constructed based on the plasmid pMODP$_{gap}$taltktCm (FIG. 2). The P$_{gap}$taltkt DNA fragment was removed by SacI/SfiI digestion. An adaptor fragment containing SacI, NotI, and SfiI restriction sites was introduced by ligation. A NotI fragment of P$_{gap}$xylAB, that was isolated from pZB4 (U.S. Pat. No. 5,514,583), was then cloned in the NotI site of the adaptor. Xylose isomerase (XI) is encoded by xylA and xylulokinase (XK) is encoded by xylB. The complete nucleotide sequence for the pMODP$_{gap}$xylABCm plasmid is given as SEQ ID NO: 12.

Transposition and Transformation of pMOD$_{gap}$xylABCm in T2C, T3C, T4C and T5C Using a similar approach to the integration of P$_{gap}$taltktCm, T2C, T3C, T4C and T5C were transformed/transposed with pMODP$_{gap}$xylABCm (described above) treated with transposase. Six integrants (T3CCmX1, T3CCmX2, T3CCmX3, T4CCmX1, T5CCmX1, T5CCmX2) were obtained in 2 transformation/transposition experiments following Cm selection. All were confirmed for the presence of xylAB by PCR using two sets of primers: SEQ ID NOs:13, and 14, and SEQ ID NOs:15 and 16 except for T2CcmX1 and T2CcmX6 from which no PCR fragment was detected using the primers SEQ ID NOs:13 and 14.

Figure 4:
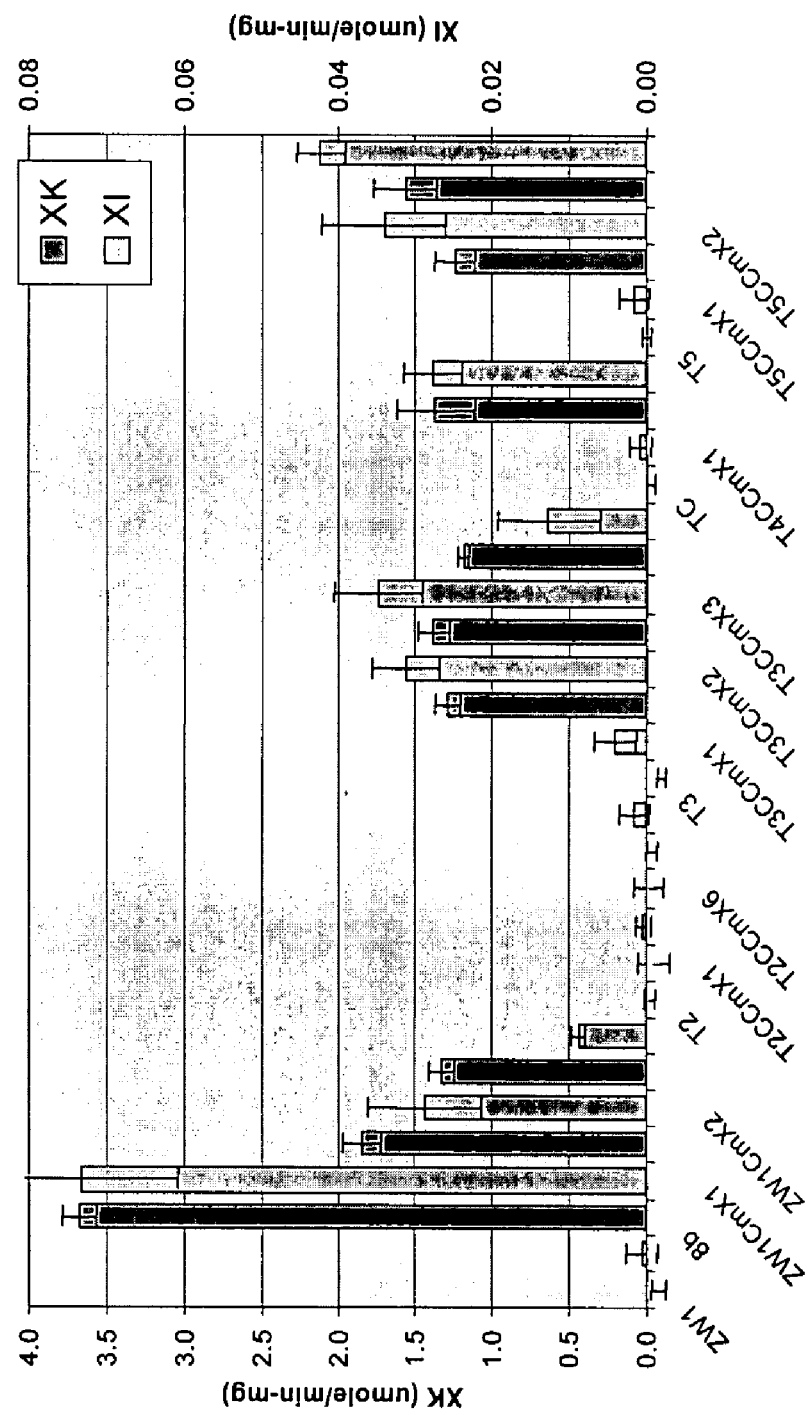
FIG. 4 shows a graph of xylose isomerase (XI) and xylulokinase (XK) activities in T2C, T3C, T4C, and T5C lines transformed with PgapxylAB.
Figure 5:
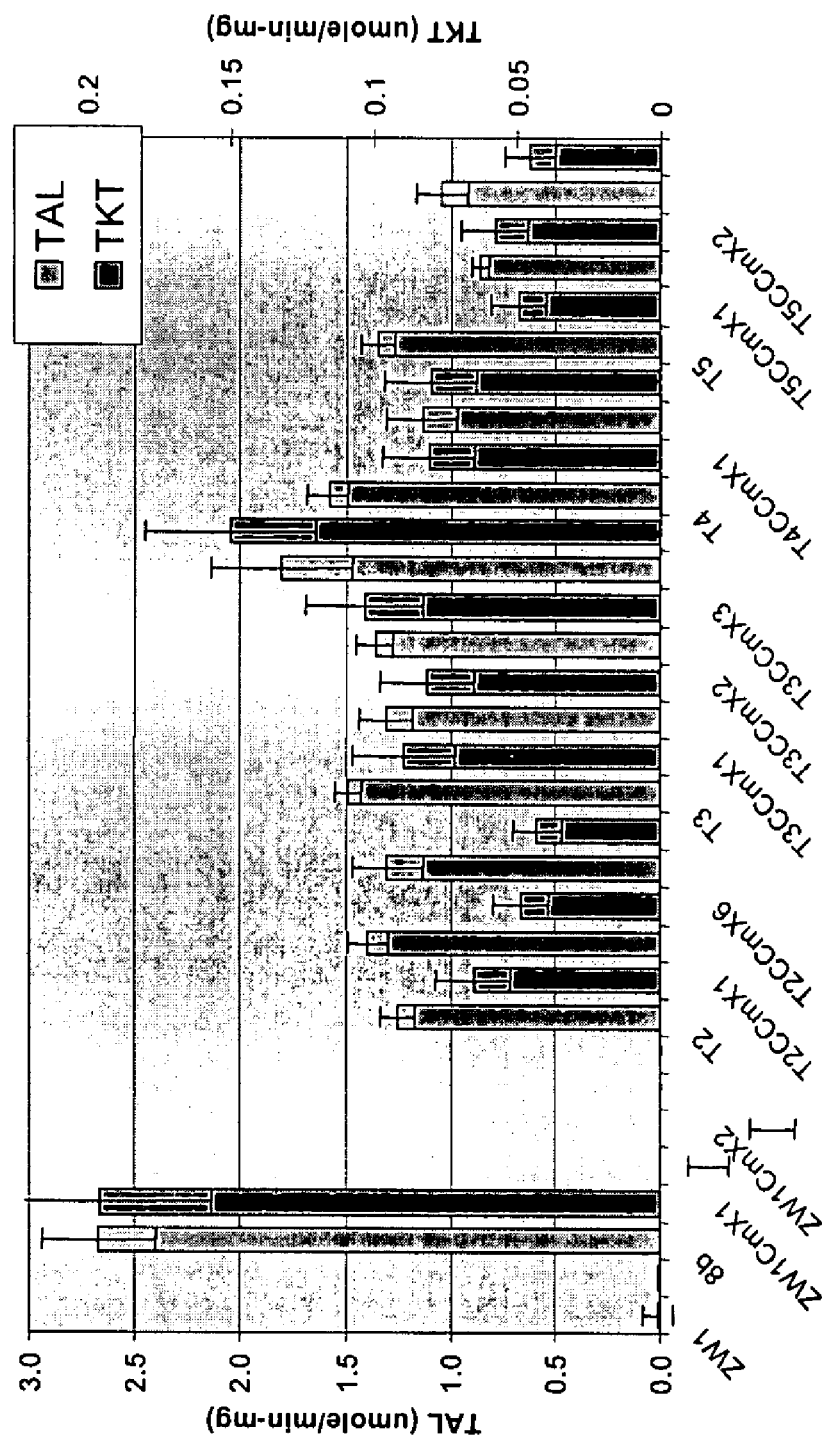
FIG. 5 shows a graph of transaldolse (TAL) and transketolase (TKT) activities in T2C, T3C, T4C, and T5C lines transformed with PgapxylAB.

The integrants, including the 2 PCR negative lines, were assayed for XI, XK, TAL and TKT activities (General Methods). The results shown in FIGS. 4 and 5 indicated that the six xylAB integrants T3CCmX1, T3CCmX2, T3CCmX3, T4CCmX1, T5CCmX1, and T5CCmX2 all had XI, XK, TAL and TKT activities. XI and XK activities were newly acquired as compared to the negative parental controls (FIG. 4). TAL and TKT activities were maintained as in the parental controls. All results indicated that the proteins were made and functional. Enzyme activity levels varied, with TI and XK activities similar to those of ZW1 integrants transformed/transposed with the same plasmid. The levels of activities of XI, XK, TAL and TKT were lower than those in strain 8b.

The integration of the xylAB operon was confirmed by Southern hybridization. Both genomic and plasmid DNA of the 6 lines were digested with SphI and hybridized to a digoxenin labeled xylB probe. A common band of about 3 kb, which is generated from an SphI site in xylB and another SphI site in the adjacent cloning sites on the pMOD vector, was present in all genomic DNA samples, and in addition, higher molecular weight hybridizing bands in the genomic DNA samples indicated that there were four sites of integration for the $P_{gap}$xylAB operon in the chromosome. T3CCmX1 and T3CCmX2 appear to have the same integration site, T3CCmX3 and T4CCmX1 may have the same integration site, and T5CCmX1 and T5CCmX2 each have a separate integration site. Digestion of the same DNA with PstI followed by Southern hybridization with the tkt probe demonstrated that each integrant had the same hybridization pattern as its respective parental strain.

Adaptation of the ZW1::$P_{gap}$taltkt $P_{gap}$xylAB Cm Integrants on xylose Media Despite the presence of all four enzymatic activities for xylose utilization, our previous observations (US Patent Application 20030162271) indicated that the integrants may not grow on xylose immediately. Growth on xylose may occur after prolonged incubation on xylose medium (either in test tubes or on plates), a process called adaptation.

The strains were adapted as follows. ZW1::$P_{gap}$taltkt $P_{gap}$xylABCm integrant strains were inoculated into test tubes and plates containing RMX (containing 10 g/l yeast extract, 2 g/l KH$_2$PO$_4$, 20 g/l or 2% (w/v) xylose as well as RMGX (RM with 0.025% (w/v) glucose, 4% (w/v) xylose). The low level of glucose was used to support initial growth to increase the chance of mutation during adaptation. One of at least five attempts at adaptation on xylose in both cultures and plates was successful. After 10 days of anaerobic incubation at 30° C., 17 and 19 colonies were visible on MMGX plated with T3CCmX1 and T3CCmX2 cells, respectively. The colonies were small and looked unhealthy (transparent) on the plates. Twelve colonies (four from T3CCmX1 plating: T3CCmX11, T3CCmX12, T3CCmX13 and T3CCmX110; eight from T3CCmX2 plating: T3CCmX24, T3CCmX25, T3CCmX26, T3CCmX27, T3CCmX28, T3CCmX29, T3CCmX211 and T3CCmX212) were inoculated in RMGCm120 and transferred into 3 ml RMX for further adaptation to obtain lines that were able to grow faster on xylose.

Adaptation of integrants in test tubes containing 3 ml RMX was conducted at 30° C. OD$_{600}$ was constantly monitored in a Spectronic 601 spectrophotometer. When the growth reached mid-log phase, the cultures were transferred into fresh tubes of RMX. This process was continued for 7 transfers. The growth rates and final ODs (non-linear readings) were improved over the transfers.

Figure 6:
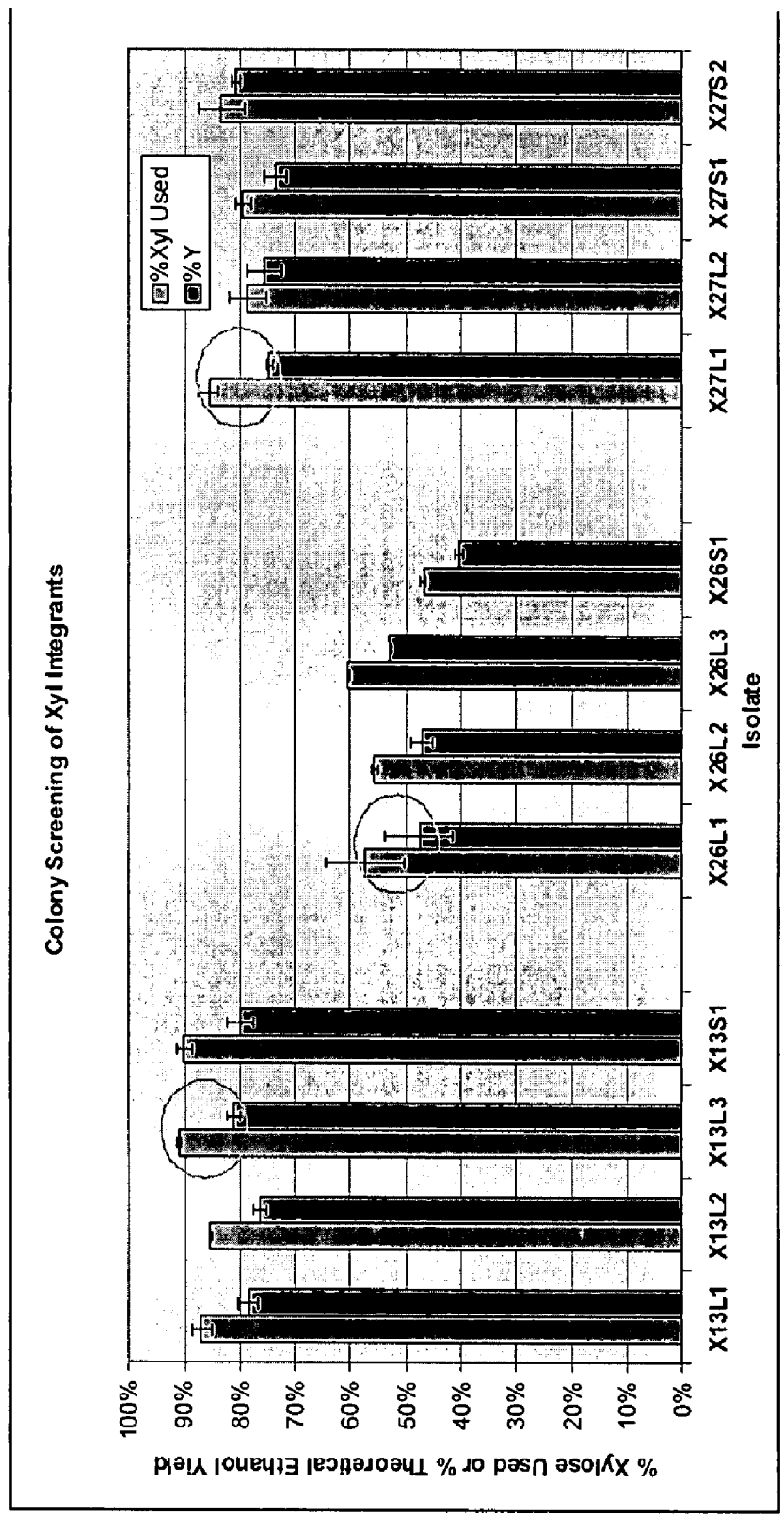
FIG. 6 shows a graph of % theoretical ethanol yield and % xylose utilization of selected adapted xylose-utilizing strain colonies.

At the 6$^{th}$ transfer, the cultures were streaked out on RMX plates to isolate single colonies. Three integrants grew faster than others on RMX streaked plates: T3CCmX13, T3CCmX26 and T3CCmX27, which are referred to as X13, X26 and X27 in the tables and discussion below. To screen for the best xylose growers, we selected four large (L1-4) and four small (S1-4) colonies each for TX13, X26 and X27 and grew these in RMX test tubes so we could monitor growth, sugar utilization, and ethanol production. Colonies were grown overnight at 30° C. followed by inoculation of OD$_{600}$=0.05 into 3 ml of RMX in test tubes in duplicates. X27 grew more slowly in RMG than the other cultures and was inoculated again 6.5 hrs later. After 69 hrs (62.5 hrs for X27), samples were taken for HPLC analysis (General Methods). FIG. 6 charts the average ethanol yield (% of theoretical yield) and xylose utilization (%) for cultures at 69 hours (62.5 hr for all X27 cultures). There was no significant difference between the large and small colonies. Although the performance of X27 was better as compared to X26 on xylose, it showed slower growth on glucose. Therefore, the top performers, large colonies of X13 (X13L3) and X26 (X26L1), were chosen for further evaluation in pH-controlled fermentations. The fermentations were conducted in RMG (6% glucose), RMX (6% xylose) and RMGX (8%:4%; glucose:xylose) at 37° C. for strains X13L3 and X26L1, as well as the control strain 8b. Fermentation of glucose by X13L3 and X26L1 grown in RMG (6%) and RMGX (8%:4%) proceeded rather quickly. The fermentation of xylose in the RMGX (8%:4%) was slower for both X13L3 and X26L1 as compared to that of strain 8b. In addition, growth on RMX (6%) at 37° C. occurred after a long lag for both X13L3 and X26L1. Several isolates, X13b, X13c and X13FL, were recovered from RMX (6%) fermentations. These isolates along with the original strains X13a (an isolate of X13L3) and X26 were subjected to Cre treatment, as described previously in this Example, to remove the Cm$^r$ marker from ZW1::$P_{gap}$taltkt $P_{gap}$xylABCm strains. The resulting Cre treated, Cm$^r$-free integrants were named: X13aC, X13bC, X13cC, X13FLC and X26C.

Adaptation of Integrants in xylose Medium by Serial Transfers in RMX (5%) at 37° C.

As described earlier, adaptation of the initial ZW1::$P_{gap}$-taltktP$_{gap}$xylABCm strains on RMX at 30° C. greatly improved the growth of strains in these conditions. However, the adapted strains suffered a long lag during growth and fermentation in RMX (6%) at 37° C. To further improve the integrants for xylose fermentation at preferred process conditions including higher sugar concentration and temperature, the evolutionary or adaptation process was continued in RMX (5%) at 37° C. Serial transfers were conducted and the best growers were selected. Integrants used in this process included X13aC, X13bC, X13cC, X26C and X13FLC. These 5 strains were grown in RMX at 30° C. for 6 transfers before being transferred to RMX (5%) at 37° C. for another 5 to 16 transfers. During and after all the transfers cultures were streaked on RMX plates and incubated at 37° C. to isolate single colonies. Large colonies were further streaked on RMX plates and incubated at 37° C. for 3 to 4 times to purify the colonies. Final large colonies were selected for growth testing in RMX (5%) at 37° C.

Evaluation of Strains from Adaptation in RMX (5%) Medium at 37° C.

Eighteen colonies isolated after adaptation with serial transfers were tested in RMX (5%) test tubes at 37° C. initially. Twelve strains were selected for a 2nd test tube evaluation. Strain 8b was included in all the evaluations for comparison. The 18 colonies were grown up in RMG at 37° C. overnight, centrifuged and the cells were inoculated into 4 ml of RMX (5%) at 37° C., statically in test tubes for the $1^{st}$ evaluation. Based on the growth ($OD_{600}$, non-linear) and end point HPLC results (low residual xylose and high ethanol), 12 strains were selected for the $2^{nd}$ evaluation.

One of the purposes of the $2^{nd}$ evaluation was to test the stability of improved growth on xylose and xylose utilization capability of the strains. All 12 strains were subjected to a stability study to see whether the adapted strains were stable after being exposed to a non-selective medium in which they were serially transferred in at 37° C. for 50 generations. Cultures before and after RMG (5%) transfers were inoculated in RMX (5%) test tubes and grown at 37° C. for evaluation. The non-linear ODs were monitored by direct reading of test tubes in a Spectronic 601 spectrophotometer. The ODs at the $70^{th}$ hour of growth in RMX (5%) before and after 50 generations of growth in RMG are plotted in FIG. 7. The results indicated that most strains were stable after 50 generations in RMG at 37° C. The endpoint (at stationary phase) supernatants were also analyzed by HPLC as described in General Methods for xylose and ethanol concentrations. The low residual xylose and high ethanol concentrations in these cultures supported the fact that the strain grew and fermented xylose well.

Based on the results from the above test tube evaluation (low residual xylose, high ethanol concentration and higher OD) and a subsequent microtiter plate growth screening with high concentrations of glucose and/or xylose (up to 20%) and mixtures of glucose and xylose with acetate to select better growers in high sugars and in the presence of acetate, focus was directed to strain #26, designated as ZW658, which exhibited the best overall performance.

Example 2

Fermentation Evaluation of Top Improved Xylose-utilization Strains at 37° C

The following example illustrates the fermentation performance of the improved xylose-utilizing *Zymomonas* strain ZW658 under fermentation conditions that mimic the sugar concentrations and the acetic acid level expected in a biomass hydrolysate. Strain ZW658 was inoculated into fermentors containing RM medium supplemented with 10% glucose (RMG10%), 8% xylose (RMX8%), 10% glucose+8% xylose (RMGX10%8%) and 10% glucose+8% xylose+0.6% acetic acid (RMGXAc10%8%0.6%), respectively. All fermentations were conducted in Sixfors with 300 ml media at 150 rpm, pH5.5 and 37° C. Nitrogen was purged through the media in the fermentors overnight and stopped right before inoculation. No nitrogen was purged during the fermentation. Inocula for the fermentation were prepared with RMGX (10%,4%) at 37° C. in shake flasks (150 rpm) after reviving of the working stocks in RMG5%. Strain 8b was used as a control under the same conditions. Samples were taken periodically for $OD_{600}$ measurement, as well as for HPLC analysis (a described in General Methods) for glucose, xylose, xylitol, and ethanol. As shown in FIG. 8, ZW658 grew more slowly on RMG10% as compared to 8b (A and B), and grew at a similar rate to 8b on RMX8% (C and D). Despite the slower growth rate, FIG. 8 shows that the ethanol yield of ZW658 (93%) was similar to that of 8b at the end of fermentation in glucose medium. In RMX8% medium, the ethanol yield was higher for ZW658 (0.46 g ethanol/g sugar) as compared to 8b (0.44 g ethanol/g sugar). ZW658 produced about 4 g/l more ethanol as compared to 8b in RMX8%. Interestingly, ZW658 did not produce any xylitol while 8b produced a low level of xylitol (0.7 g/l) at the end of the fermentation in RMX8%. Data shown in FIG. 9 shows that ZW658 performed better as compared to 8b in fermenting 10% glucose+8% xylose with (C, D) or without (A, B) acetate, indicated by more glucose and xylose consumption, less xylitol production, and more ethanol production. Most of the glucose was used and substantial residual xylose remained at the end of the fermentation for both strains in RMG10% X8%, at 37° C. and pH5.5, although ZW658 used about 8 g/l more xylose than 8b. Xylitol production (4.9 g/l) in ZW658 in RMG10% X8% at 37° C. and pH5.5 at the end of the fermentation was significantly lower than that of 8b (8.2 g/l). In the presence of acetate (6 g/l), the cell growth of both strains was reduced significantly resulting in poor fermentation performance of both glucose and xylose, although ZW658 showed slightly better fermentation performance in terms of more glucose and xylose consumption, less xylitol production and more ethanol production. Unlike in the RMX8%, both strains produced the by-product xylitol in RMG10% X8% with or without acetate, although less xylitol was produced by ZW658 as compared to 8b. The fermentation performance of the two strains is summarized in Table 1. Overall, ZW658 performed better than 8b in pure sugar fermentations. As described in Example 1, ZW658 is free of antibiotic selection markers, which is a valuable property for fermentation organisms in commercial applications.

TABLE 1

Summary of fermentation performance of ZW658 and 8b for ethanol production.

|  | Ethanol Yield g ethanol/g sugar | Vol. Prod. g/l/h | Ethanol g/l | CPI g/g |
|---|---|---|---|---|
| 8b (Glu) | 0.47 | 5.15 | 52 | 21 |
| ZW658 (Glu) | 0.48 | 4.13 | 52 | 15 |
| 8b (Xyl) | 0.44 | 1.66 | 37 | 24 |
| ZW658 (Xyl) | 0.46 | 1.83 | 41 | 23 |
| 8b (Glu Xyl) | 0.43 | 1.80 | 58 | 52 |
| ZW658 (Glu Xyl) | 0.45 | 2.03 | 65 | 35 |
| 8b (Glu Xyl Ac) | 0.46 | 0.67 | 48 | 136 |
| ZW658 (Glu Xyl Ac) | 0.47 | 1.04 | 50 | 90 |

CPI is Cell Productivity Index: g ethanol/g dry cell weight

Example 3

Ethanol Production by Strain ZW658 Grown on High Concentration Glucose or Xylose in the Presence and Absence of Sorbitol In four sterilized 125 ml Erlenmeyer culture flasks (Cat. No. 30180-036, VWR International, USA), 10 ml of ZW658 strain seed culture at $OD_{600}$ of approximately 5 was inoculated into each flask with 100 ml of aqueous solution containing 10 g/L yeast extract (YE), 2 g/L $KH_2PO_4$, 4 g/L $KHCO_3$. Before inoculation, the first flask also contained 200 g/L glucose and 20 mM sorbitol, comparing to the second flask with 200 g/L glucose only. The third flask contained 200 g/L xylose and 20 mM sorbitol, comparing to the fourth flask with 200 g/L xylose only. After inoculation, sugar concentrations were diluted to about 180 g/L. Initial pH was adjusted to 5.5 with 4 NH$_3$PO$_4$ solution. Mixing speed was set at 150 rpm. Fermentation was conducted at 33° C. and pH was not controlled. Samples were taken periodically. Samples were filtered through 0.22 micron filters, and the filtrates were analyzed by HPLC as described in General Methods for compounds including glucose, xylose, ethanol, and xylitol. Samples were diluted with medium (as described in General Methods) and the OD$_{600}$ was measured to monitor cell growth. FIG. 10A shows the OD$_{600}$ at time points between 0 and 48 hr. After 48 hours, the OD$_{600}$ were 9.94, 6.46, 5.37 and 5.45, respectively, for the first, second, third, and fourth flask. These results show that sorbitol significantly stimulated growth in high concentration glucose culture, but showed almost no effect on growth in high concentration xylose culture.

Results in FIG. 10B show that ethanol production was more rapid in glucose with sorbitol, but ethanol in cultures with and without sorbitol reached the same level after about 20 hr. In the xylose only cultures, ethanol production was at the same rate with and without sorbitol, with the sorbitol sample producing less ethanol at 48 hr than the no sorbitol sample. No xylitol was produced in any of these cultures.

Example 4

Ethanol Production by Strain ZW658 Grown on High Concentration Glucose and Xylose in the Presence of Sorbitol In a sterilized 1-liter fermentor (BIOSTAT® B-DCU system, Sartorius BBI System Inc., Bethlehem, Pa., USA), 50 ml of ZW658 strain seed culture at Optical Density of approximately 5 (measured at 600 nm) was inoculated into 450 ml of aqueous solution containing sugars and medium. The final mixed broth contained 100 g/L glucose, 85.1 g/L xylose, 10 g/L yeast extract (YE), 2 g/L KH$_2$PO$_4$, and 10 mM sorbitol. pH was adjusted to 5.5 with 4 N KOH solution. Mixing speed was set at 150 rpm. Fermentation was conducted at 33° C. and pH 5.5. Samples were taken periodically. Samples were filtered through 0.22 micron filters, and the filtrates were analyzed by HPLC as described in General Methods for compounds including glucose, xylose, ethanol, and acetate. Samples were also diluted with medium (as described in General Methods) and the OD$_{600}$ was measured to monitor cell growth. FIG. 11 shows the amounts of glucose, xylose, xylitol, ethanol and acetic acid present, as well as the OD$_{600}$ at time points between 0 and 65 hr. After 29 hours, the glucose and xylose concentrations were 0 and 2.08 g/L, respectively, and the ethanol concentration reached 83.9 g/L. Cells grew to an OD$_{600}$ of 13. The by-product xylitol concentration was 0.67 g/L at 29 hr, and increased to 0.95 g/L at 64 hr.

Example 5

Ethanol Production by Strain ZW658 Grown on High Concentration Glucose and Xylose in the Absence of Sorbitol In a sterilized 1-liter fermentor (BIOSTAT® B-DCU system, Sartorius BBI System Inc., Bethlehem, Pa., USA), 50 ml of ZW658 strain seed culture at Optical Density of approximately 5 (measured at 600 nm) was inoculated into 450 ml of aqueous solution containing sugars and medium. The final mixed broth contained 103 g/L glucose, 85.0 g/L xylose, 10 g/L yeast extract (YE), 2 g/L KH$_2$PO$_4$. pH was adjusted to 5.5 with 4 N KOH solution. Mixing speed was set at 150 rpm. Fermentation was conducted at 33° C. and pH 5.5. Samples were taken periodically. Samples were filtered through 0.22 micron filters, and the filtrates were analyzed by HPLC as described in General Methods for compounds including glucose, xylose, ethanol, and acetate. Samples were also diluted with medium (as described in General Methods) and the OD$_{600}$ was measured to monitor cell growth. FIG. 12 shows the amounts of glucose, xylose, ethanol and acetic acid present, as well as the OD$_{600}$ at time points between 0 and 70 hr. The glucose concentration did not reach 0 until 40 hours and the xylose concentration never was reduced to 2 g/L, as it was when sorbitol was present in the Example 3 experiment. At the end of the run, after 67 hr, xylose was only reduced to 17.8 g/L. Xylitol production was about 0.21 g/L at 29 hr, and increased to 3.08 g/L after 64 hr, an over 3-fold higher amount than was produced in the Example 1 experiment. After 67 hours, the ethanol concentration reached 77.2 g/L, and cells grew to an OD$_{600}$ of 6.7.

Comparing Examples 3 and 4, the resulted showed that adding sorbitol significantly reduced the lag time and improved sugar utilization (or uptake) rates, final ethanol concentration (i.e. yield), and doubled the growth. Less xylitol was produced.

Example 6

Ethanol Production by Strain ZW658 Grown on High Concentration Glucose and Xylose in the Presence of Sorbitol and Acetate In a sterilized 1-liter fermentor (BIOSTAT® B-DCU system, Sartorius BBI System Inc., Bethlehem, Pa., USA), 50 ml of ZW658 strain seed culture at OD$_{600}$ of approximately 5 was inoculated into 450 ml of aqueous solution containing sugars and medium. The final mixed broth contained 99.0 g/L glucose, 82.7 g/L xylose, 5.8 g/L acetate (in the form of potassium acetate), 10 g/L yeast extract (YE), 2 g/L KH$_2$PO$_4$, and 10 mM sorbitol. pH was adjusted to 5.5 with 4 N KOH solution. Mixing speed was set at 150 rpm. Fermentation was conducted at 33° C. and pH 5.5. Samples were taken periodically. Samples were filtered through 0.22 micron filters, and the filtrates were analyzed by HPLC as described in General Methods for compounds including glucose, xylose, ethanol, and acetate. Samples were also diluted with medium (as described in General Methods) and the OD$_{600}$ was measured to monitor cell growth. FIG. 13 shows the amounts of glucose, xylose, xylitol, ethanol and acetic acid present, as well as the OD$_{600}$ at time points between 0 and 64 hr. After 63.75 hours, the glucose and xylose concentrations were 0 and 29.6 g/L, respectively, and the ethanol concentration reached 70.0 g/L; cells grew to an OD$_{600}$ of 6.4; by product xylitol concentration was 3.55 g/L.

Example 7

Ethanol Production by Strain ZW658 Grown on High Concentration Glucose and Xylose in the Presence of Acetate without Sorbitol In a sterilized 1-liter fermentor (BIOSTAT® B-DCU system, Sartorius BBI System Inc., Bethlehem, Pa., USA), 80 ml of ZW658 strain seed culture at OD$_{600}$ of approximately 5 was inoculated into 720 ml of aqueous solution containing sugars and medium. The final mixed broth contained 97.2 g/L glucose, 81.0 g/L xylose, 5.7 g/L acetate (in the form of potassium acetate), 5 g/L yeast extract (YE), 2 g/L KH$_2$PO$_4$, 2 g/L (NH$_4$)$_2$SO$_4$ and 1 g/L MgSO$_4$.7H$_2$O. pH was adjusted to 5.5 with 4 N KOH solution. Mixing speed was set at 150 rpm. Fermentation was conducted at 33° C. and pH 5.5. Samples were taken periodically. Samples were filtered through 0.22 micron filters, and the filtrates were analyzed by HPLC as described in General Methods for compounds including glucose, xylose, xylitol, ethanol, and acetic acid. Samples were also diluted with medium (as described in General Methods) and the $OD_{600}$ was measured to monitor cell growth. FIG. 14 shows the amounts of glucose, xylose, ethanol and acetic acid present, as well as the $OD_{600}$ at time points between 0 and 140 hr. After 63 hours, the glucose and xylose concentrations were 0 and 50 g/L, respectively, and the ethanol concentration reached 61.8 g/L. Cells grew to an $OD_{600}$ of 3.3. After 135 hours, the xylose concentration was reduced to 38 g/L, and the ethanol concentration reached 64.4 g/L. The by-product xylitol concentration was 1.3 g/L at 63 hr, and increased to 4.4 g/L after 135 hr. When the 4.4 g/L of xylitol produced at stationary phase of the fermentation culture with no sorbitol was compared to the 3.55 g/L of xyliitol produced at stationary phase of the fermentation culture with sorbitol (Example 6), the results showed that adding sorbitol reduced the amount of xylitol produced in the presence of acetate.

Example 8

Ethanol Production by Strain ZW658 Grown on High Concentration Glucose and Xylose in the Presence of Glutamate In a sterilized 1-liter fermentor (BIOSTAT® B-DCU system, Sartorius BBI System Inc., Bethlehem, Pa., USA), 50 ml of ZW658 strain seed culture at $OD_{600}$ of approximately 5 was inoculated into 450 ml of aqueous solution containing sugars and medium. The final mixed broth contained 98.0 g/L glucose, 81.2 g/L xylose, 10 g/L yeast extract (YE), 2 g/L $KH_2PO_4$, and 10 mM potassium glutamate. pH was adjusted to 5.5 with 4 N KOH solution. Mixing speed was set at 150 rpm. Fermentation was conducted at 33° C. and pH 5.5. Samples were taken periodically. Samples were filtered through 0.22 micron filters, and the filtrates were analyzed by HPLC as described in General Methods for compounds including glucose, xylose, xylitol, ethanol, and acetic acid. Samples were also diluted with medium (as described in General Methods) and the $OD_{600}$ was measured to monitor cell growth. FIG. 15 shows the amounts of glucose, xylose, ethanol and acetic acid present, as well as the $OD_{600}$ at time points between 0 and 63.75 hr. Glutamate reduced the lag period and the glucose concentration reached 0 at 24 hr. However, xylose was not well-utilized, cell growth and ethanol production were reduced as compared to that in the presence of sorbitol (Example 4), and xylitol production increased. After 63.75 hours, the glucose and xylose concentrations were 0 and 21.2 g/L, respectively, and the ethanol concentration reached 72.3 g/L; cells grew to an $OD_{600}$ of 6.9; by-product xylitol concentration was 4.38 g/L. The results indicated that glutamate reduced the lag time and improved glucose utilization (or uptake) rates, but had less beneficial effect than sorbitol on xylose usage, cell growth, and production of the xylitol by-product.

Example 9

Ethanol Production by Strain ZW658 Grown on High Concentration Glucose and Xylose in the Presence of Sorbitol at Various Concentrations In five sterilized 125 ml Erlenmeyer culture flasks (Cat. No. 30180-036, VWR International, USA), 10 ml of ZW658 strain seed culture at $OD_{600}$ of approximately 5 (measured at 600 nm) was inoculated into each flask with 100 ml of aqueous solution containing 100 g/L glucose, 80 g/L xylose, 10 g/L yeast extract (YE), 10 g/L $KH_2PO_4$, 2 g/L (NH4)2SO4, 1 g/L MgSO4.7H2O, and various concentrations of sorbitol (0, 0.5, 1, 2, and 10 mM). After inoculation, the total sugar concentration was about 160 g/L due to dilution by the seed culture. Initial pH was adjusted to 5.5 with 4 N KOH solution. Mixing speed was set at 150 rpm. Fermentation was conducted at 33° C. and pH was not controlled. Samples were taken periodically. Samples were diluted with medium (as described in General Methods) and the $OD_{600}$ was measured to monitor cell growth. FIG. 16 shows the $OD_{600}$ at time points between 0 and 28 hr. Cultures with higher concentration of sorbitol, in this range, grew faster and better. After 14.25 hours, the $OD_{600}$ were 4.19, 7.10, 8.08, 8.62, and 10.1, respectively, for sorbitol concentrations of 0, 0.5, 1, 2, and 10 mM.

Example 10

Ethanol Production by Strain ZW658 Grown on High Concentration Glucose and Xylose in the Presence of Sorbitol at Various Concentrations up to 200 mM In five sterilized 125 ml Erlenmeyer culture flasks (Cat. No. 30180-036, VWR International, USA), 10 ml of ZW658 strain seed culture at Optical Density of approximately 5 (measured at 600 nm; $OD_{600}$) was inoculated into each flask with 100 ml of aqueous solution containing 110 g/L glucose, 90 g/L xylose, 10 g/L yeast extract (YE), 2 g/L $KH_2PO_4$, 4 g/L $KHCO_3$, and various concentrations of sorbitol (10, 20, 50, 100, and 200 mM). Initial pH was adjusted to 5.5 with 4 $NH_3PO_4$ solution. Mixing speed was set at 150 rpm. Fermentation was conducted at 33° C. and pH was not controlled. Samples were taken periodically. Samples were filtered through 0.22 micron filters, and the filtrates were analyzed by HPLC as described in General Methods for ethanol. Samples were diluted with medium (as described in General Methods) and the $OD_{600}$ was measured to monitor cell growth. FIG. 17 shows the $OD_{600}$ (A) and ethanol (B) produced at time points between 0 and 48 hr. After 24 hours, the $OD_{600}$ were 7.74, 7.86, 8.04, 7.82, and 7.12, respectively, for sorbitol concentrations of 10, 20, 50, 100, and 200 mM. After 48 hours, the $OD_{600}$ were 8.30, 8.26, 8.84, 8.12, and 7.72, respectively, for sorbitol concentrations of 10, 20, 50, 100, and 200 mM. These results showed that cultures with 10-100 mM sorbitol grew similarly, while the culture with 200 mM sorbitol grew slightly slower. Ethanol production was slightly slower with 100 or 200 mM sorbitol than with 10, 20, or 50 mM sorbitol, although all cultures reached about the same final amount of ethanol produced. No xylitol was detected in any of the samples. Thus 10 mM sorbitol is adequate to provide maximal ethanol production under these conditions.

Example 11

Ethanol Production by Strain ZW658 Grown on High Concentration Glucose and Xylose in the Presence of Various Polyols In five sterilized 125 ml Erlenmeyer culture flasks (Cat. No. 30180-036, VWR International, USA), 10 ml of ZW658 strain seed culture at $OD_{600}$ of approximately 5 was inoculated into each flask with 100 ml of aqueous solution containing 100 g/L glucose, 80 g/L xylose, 10 g/L yeast extract (YE), 2 g/L KH$_2$PO$_4$, 1 g/L MgSO$_4$.7H$_2$O, and 4 g/L KHCO$_3$, and 10 mM of one of the following polyols: erythritol, sorbitol, mannitol, maltitol, or lactitol. After inoculation, the total sugar concentration was about 160 g/L due to dilution by the seed culture. Initial pH was adjusted to 5.5 with 4 N H$_3$PO$_4$ solution. Mixing speed was set at 150 rpm. Fermentation was conducted at 33° C. and pH was not controlled. Samples were taken periodically. Samples were filtered through 0.22 micron filters, and the filtrates were analyzed by HPLC as described in General Methods for compounds including glucose, xylose, ethanol, xylitol, and acetic acid. Samples were diluted with medium (as described in General Methods) and the OD$_{600}$ was measured to monitor cell growth. FIG. 18 shows the OD$_{600}$ (A), xylose utilization (B), and ethanol production (C) at time points between 0 and 32 hr. Cultures with sorbitol or mannitol grew faster and better. After 32 hours, the OD$_{600}$ were 13.94 and 13.92, respectively, for cultures supplemented with sorbitol or mannitol; meanwhile, the OD$_{600}$ were 9.48, 9.02, and 9.24, respectively, for cultures supplemented with erythritol, maltitol, or lactitol. More xylose was utilized, and ethanol production was also better with sorbitol or mannitol in the medium. No xylitol was detected in any of the cultures. The presence of sorbitol or mannitol allowed more xylose utilization, without production of xylitol.

This example shows that mannitol is as effective on improving cell growth, xylose utilization, reducing xylitol, and increasing ethanol production as sorbitol at the same concentration in high concentration sugars.

Example 12

Ethanol Production by Strain ZW658 Grown on High Concentration Glucose and Xylose in the Presence of Acetate and Various Polyols In five sterilized 125 ml Erlenmeyer culture flasks (Cat. No. 30180-036, VWR International, USA), 10 ml of ZW658 strain seed culture at OD$_{600}$ of approximately 5 was inoculated into each flask with 100 ml of aqueous solution containing 100 g/L glucose, 80 g/L xylose, 3 g/L acetate, 10 g/L yeast extract (YE), 2 g/L KH$_2$PO$_4$, 1 g/L MgSO$_4$.7H$_2$O, and 4 g/L KHCO$_3$, and 10 mM of the following polyols: erythritol, sorbitol, mannitol, maltitol, or lactitol; or 5 mM sorbitol plus 5 mM maltitol, or 5 mM sorbitol plus 5 mM lactitol. After inoculation, the total sugar concentration was about 160 g/L due to dilution by the seed culture. Initial pH was adjusted to 5.5 with 4 N H$_3$PO$_4$ solution. Mixing speed was set at 150 rpm. Fermentation was conducted at 33° C. and pH was not controlled. Samples were taken periodically. Samples were filtered through 0.22 micron filters, and the filtrates were analyzed by HPLC as described in General Methods for compounds including glucose, xylose, ethanol, and acetate. Samples were diluted with medium (as described in General Methods) and the OD$_{600}$ was measured to monitor cell growth. FIG. 19 shows the OD$_{600}$ (A), xylose utilization (B), and ethanol production (C) at time points between 0 and 32 hr. Cultures with sorbitol or mannitol grew faster and better than cultures without either of these components. After 32 hours, the OD$_{600}$ were 7.88, 7.40, 7.62 and 7.78, respectively, for cultures supplemented with 10 mM sorbitol, 10 mM mannitol, 5 mM sorbitol plus 5 mM maltitol, and 5 mM sorbitol plus 5 mM lactitol; meanwhile, the OD$_{600}$ were 5.20, 5.20, and 5.30, respectively, for cultures supplemented with erythritol, maltitol, or lactitol. More xylose was utilized, and ethanol production was also better with sorbitol or mannitol in the medium. No xylitol was detected in any of the cultures. The presence of sorbitol or mannitol allowed more xylose utilization, without production of xylitol.

This example shows that mannitol is as effective in improving cell growth, xylose utilization, reducing xylitol, and increasing ethanol production as sorbitol at the same concentration in high concentration sugars with acetate. Combining sorbitol with polyols of higher molecular weight (maltitol or lactitol) did not show synergistic improvement on fermentation.

Example 13

Ethanol Production by Strain ZW658 Grown on High Concentration Glucose and Xylose in the Presence of Various Sugar Alcohols In eight sterilized 50 ml screw-cap centrifuge tubes (Cat. No. 21008-178, VWR International, USA), 200 μl of ZW658 strain glycerol stock at OD$_{600}$ of approximately 10 was inoculated into each flask with 25 ml of aqueous solution containing 92 g/L glucose, 82 g/L xylose, 10 g/L yeast extract (YE), 2 g/L KH$_2$PO$_4$, 1 g/L MgSO$_4$.7H$_2$O, and either 10 mM of sorbitol, arabitol, adonitol (also called ribitol), or galactitol; or 50 mM of arabitol, adonitol, or galactitol. The control had no sugar alcohol added. Initial pH was adjusted to 5.5 with 4 N H$_3$PO$_4$ solution. Fermentation was conducted at 33° C. and pH was not controlled. Samples were taken periodically between 0 and 40 hr. Samples were filtered through 0.22 micron filters, and the filtrates were analyzed by HPLC as described in General Methods for glucose, xylose, xylitol, and ethanol. Samples were diluted with medium (as described in General Methods) and the OD$_{600}$ was measured to monitor cell growth. Results of growth and glucose utilization are given in FIGS. 20A and 20B, respectively. Results of xylose utilization and ethanol production are given in FIGS. 21A and 21B, respectively. Cultures with sorbitol or galactitol grew much faster and better than the control. Cultures with adonitol also grew better. After 40 hours, the OD$_{600}$ were 7 to 8, for cultures supplemented with sorbitol or galactitol; the OD$_{600}$ were about 5, for cultures supplemented with adonitol; while the OD$_{600}$ were less than 1 for other cultures. More xylose was utilized, and ethanol production was also better with sorbitol or galactitol or adonitol in the medium. No xylitol was detected in any of the cultures. The presence of sorbitol, galactitol, or adonitol allowed more xylose utilization, without production of xylitol.

This example shows that galactitol is as effective on improving cell growth, xylose utilization, reducing xylitol, and increasing ethanol production as sorbitol at the same concentration in high concentration sugars. Adonitol is less effective than sorbitol.

Example 14

Ethanol Production by Strain ZW658 Grown on High Concentration Glucose and Xylose in the Presence of Various Sugar Alcohols In six sterilized 50 ml screw-cap centrifuge tubes (Cat. No. 21008-178, VWR International, USA), 200 μl of ZW658 strain glycerol stock at OD$_{600}$ of approximately 10 was inoculated into each flask with 25 ml of aqueous solution containing 92 g/L glucose, 82 g/L xylose, 10 g/L yeast extract (YE), 2 g/L KH$_2$PO$_4$, 1 g/L MgSO$_4$.7H$_2$O, and 10 mM of D-sorbitol, L-sorbitol, D-threitol, myo-inositol, or xylitol. The control had no addition of sugar alcohol. Initial pH was adjusted to 5.5 with 4 N H$_3$PO$_4$ solution. Fermentation was conducted at 33° C. and pH was not controlled. Samples were taken periodically between 0 and 48 hr. Samples were filtered through 0.22 micron filters, and the filtrates were analyzed by HPLC as described in General Methods for glucose, xylose, xylitol, and ethanol. Samples were diluted with medium (as described in General Methods) and the $OD_{600}$ was measured to monitor cell growth. Results of growth and glucose utilization are given in FIGS. 22A and 22B, respectively. Results of xylose utilization and ethanol production are given in FIGS. 23A and 23B, respectively. Cultures with D-sorbitol or L-sorbitol grew faster and better than the control. After 48 hours, the $OD_{600}$ were 6.2 and 5.2, respectively, for cultures supplemented with D-sorbitol or L-sorbitol; while the $OD_{600}$ were less than 1 for other cultures. More xylose was utilized, and ethanol production was also better with D-sorbitol or L-sorbitol in the medium. No xylitol was detected in any of the cultures. The presence of D-sorbitol or L-sorbitol allowed more xylose utilization, without production of xylitol. D-sorbitol was more effective than L-sorbitol.

What is claimed is:

1. A method for improving ethanol production comprising:
   (a) providing recombinant *Zymomonas* cells capable of converting xylose to ethanol;
   (b) providing a suitable medium comprising (i) a mixed sugar composition comprising xylose and glucose at a concentration not exceeding 15 wt % in the medium, and (ii) at least one sugar alcohol selected from the group consisting of sorbitol, mannitol, galactitol, and ribitol; and
   (c) contacting (a) with (b) whereby the *Zymomonas* cells produce ethanol.

2. The method of claim 1, wherein performance of the recombinant *Zymomonas* in converting xylose to ethanol is improved by the presence of the sugar alcohol of (b).

3. The method of claim 2, whereby a greater amount of xylose in the mixed sugar composition is converted to ethanol.

4. The method of claim 2 whereby less xylitol is produced in the presence of the sugar alcohol of claim 1(b).

5. The method of claim 1 wherein the sugar alcohol of claim 1(b) is present in the medium in an amount selected from the group consisting of about 0.5 mM to about 200 mM, about 2 mM to about 100 mM, and about 5mM to about 20 mM.

6. The method of claim 1, wherein the recombinant *Zymomonas* cells are cells from any one of the following strains, ATCC31821/pZB5, *Z. mobilis* 8b, ZW658, ZW800, ZW801-4, ZW801-6, ZM4(pZB5) or *Z. mobilis* CP4:pZB5.

7. The xylose-utilizing *Z. mobilis* strain ZW658.

8. The method of claim 1 wherein the mixed sugar composition comprises one or more additional sugar.

* * * * *